(12) United States Patent
Martin et al.

(10) Patent No.: US 10,288,545 B2
(45) Date of Patent: May 14, 2019

(54) FLUIDICS SYSTEM FOR FLOW CYTOMETER

(71) Applicant: BECKMAN COULTER, INC., Brea, CA (US)

(72) Inventors: Richard R. Martin, Fort Collins, CO (US); Todd Halvorson, Fort Collins, CO (US); Jeffrey J. Corpstein, Noblesville, IN (US)

(73) Assignee: Beckman Coulter, Inc., Brea, CA (US)

( * ) Notice: Subject to any disclaimer, the term of this patent is extended or adjusted under 35 U.S.C. 154(b) by 164 days.

(21) Appl. No.: 15/039,790

(22) PCT Filed: Nov. 26, 2014

(86) PCT No.: PCT/US2014/067685
§ 371 (c)(1),
(2) Date: May 26, 2016

(87) PCT Pub. No.: WO2015/081242
PCT Pub. Date: Jun. 4, 2015

(65) Prior Publication Data
US 2016/0377524 A1 Dec. 29, 2016

Related U.S. Application Data

(60) Provisional application No. 61/909,796, filed on Nov. 27, 2013.

(51) Int. Cl.
G01N 15/14 (2006.01)
G01N 35/10 (2006.01)

(52) U.S. Cl.
CPC ..... *G01N 15/1404* (2013.01); *G01N 15/1436* (2013.01); *G01N 35/1097* (2013.01); *G01N 2015/1409* (2013.01)

(58) Field of Classification Search
CPC ........... G01N 15/1404; G01N 15/1409; G01N 35/1097; G01N 35/10; G01N 35/1004; G01N 35/1095; G01N 15/1436
USPC ............... 356/436, 437, 438, 440, 441, 442; 324/71.4; 73/864.81, 28.01, 865.5
See application file for complete search history.

(56) References Cited

U.S. PATENT DOCUMENTS

| 5,182,617 A | 1/1993 | Yoneyama et al. |
| 2002/0015664 A1 | 2/2002 | Sklar et al. |
| 2002/0192113 A1 | 12/2002 | Uffenheimer et al. |
| 2012/0063971 A1 | 3/2012 | Carlo et al. |

OTHER PUBLICATIONS

International Search Report for International Application No. PCT/US2014/067685 dated Feb. 17, 2015.

*Primary Examiner* — Robert R Raevis
(74) *Attorney, Agent, or Firm* — Merchant & Gould P.C.

(57) ABSTRACT

A fluidics system for a flow cytometer is disclosed. In some examples, the system includes a junction disposed between a pump and a sample probe. In some examples, the pump is a peristaltic pump. A pulse-attenuation system is also disclosed. A method for removing gaps caused by pulsations in output data is also disclosed. A fluidics system and method for processing samples in parallel is also disclosed. A fluidic system for a flow cytometer that includes an agitator for agitating a sample is also disclosed. A sheath fluid transfer system of a fluidic system for a flow cytometer is also disclosed.

19 Claims, 38 Drawing Sheets

FLUIDICS SYSTEM FOR FLOW CYTOMETER

This application is a U.S. National Stage application of PCT/US2014/067685, filed Nov. 26, 2014, which claims benefit of U.S. Provisional Patent Application Ser. No. 61/909,796, filed Nov. 27, 2013 and which applications are hereby incorporated by reference in their entireties. To the extent appropriate, a claim of priority is made to each of the above disclosed applications.

BACKGROUND

A flow cytometer is useful for identifying particles and characteristics of particles contained within a fluid. The fluid is typically passed through a small nozzle that generates a narrow fluid stream. A light beam illuminates the particles in the fluid stream as they pass. Detectors are positioned to detect light transmission and scatter. This information is then used by the flow cytometer to identify the particles or characteristics of the particles in the fluid.

SUMMARY

In general terms, this disclosure is directed to a flow cytometer. In one possible configuration and by non-limiting example, the flow cytometer is configured to include a fluidics system. Various aspects are described in this disclosure, which include, but are not limited to, the following aspects.

One aspect is a flow cytometer comprising: a flow cell for passing particles in a sample; a sample probe in fluid communication with the flow cell; a pump disposed between the sample probe and the flow cell, the pump configured to provide a force to cause the displacement of the sample from the sample probe towards the flow cell; a junction disposed between the pump and the sample probe; and a first fluid-driving source in fluid communication with the junction, the first fluid-driving source configured to provide a flow of a system fluid from the junction to the sample probe while the sample is displaced from the pump to the flow cell.

Another aspect is a method of transporting particles of a sample to a flow cell in a flow cytometer comprising: aspirating a bolus of the sample into a sample probe of the flow cytometer; advancing a portion of the bolus past a connector, the connector being in fluid communication with the sample probe, the flow cell, and a valve, the valve being configured to control the flow of a system fluid into the connector; opening the valve, the valve allowing the flow of the system fluid to enter the connector; and continuing to advance the portion of the bolus to the flow cell while the flow of the system fluid enters the connector.

Another aspect is a flow cytometer comprising: a flow cell for passing particles in a sample; a sample probe to aspirate the sample; a switching valve connected to the flow cell, the sample probe, a first tube section, and a second tube section, the switching valve having a first and a second selectable position, wherein the switching valve forms a fluid connection between the sample probe and the first tube section and between the flow cell and the second tube section when the switching valve is in the first position, and wherein the switching valve forms a fluid connection between the sample probe and the second tube section and between the flow cell and the first tube section when the switching valve is in the second position; and a first pump connected to the first tube section, and a second pump connected to the second tube section, wherein the first pump is configured to cause a first sample to flow from the sample probe to the first tube section and the second pump is configured to cause a second sample to flow from the second tube section to the flow cell when the switching valve is in the first position.

Another aspect is a flow cytometer comprising: a flow cell for passing particles in a sample; a sample probe to aspirate the sample; a fluidic pathway connecting the sample probe and the flow cell; and an agitator connected to the fluidic pathway to agitate a segment of the fluidic pathway.

Another aspect is a method of processing a plurality of samples using a flow cytometer comprising: performing a first half-cycle on a first sample using a first side of the flow cytometer and simultaneously performing a second half-cycle on a second sample using a second side of the flow cytometer; switching a valve of the flow cytometer after the first half-cycle is complete and the second half-cycle is complete; and performing the second half-cycle on the first sample using the first side and simultaneously performing the first half-cycle using the second side on a third sample.

Another aspect is a particle analyzer comprising: a flow cell for passing particles in a sample; a sample probe in fluid communication with the flow cell; a sheath fluid source in fluid communication with the flow cell; a first peristaltic pump disposed between the sample probe and the flow cell, the first peristaltic pump configured to cause a sample to flow from the sample probe to the flow cell; and a second peristaltic pump disposed between the sheath fluid source and the flow cell, the second peristaltic pump configured to cause sheath fluid to flow from the sheath fluid source to the flow cell.

Another aspect is a method of displaying data from a flow cytometer, comprising: loading into memory data points, the data points representing a time interval and a number of events detected by the flow cytometer during the time interval; processing the data points to identify gap data points, the gap data points being data points representing time intervals with reduced sample flow due to pulsations; and displaying a plot of the data points with the gap data points removed.

Another aspect is a flow cytometer comprising: a flow cell for passing particles in a sample; a sample probe to aspirate a sample, the sample probe in fluid communication with the flow cell; a peristaltic pump disposed between the sample probe and the flow cell, the pump configured to advance the sample from the sample probe towards the flow cell; a display screen; and a processor configured to: collect data representing the number of events detected by the flow cytometer as a function of time; calculate smoothed data, wherein the smoothed data is a running average of the data; and generate a plot on the display screen representing the smoothed data.

Another aspect is a flow cytometer comprising: a flow cell for passing particles in a sample; a sample probe to aspirate the sample; a first fluidic pathway, the first fluidic pathway connecting a source of sheath fluid to the flow cell, the first fluidic pathway including a first peristaltic pump, the first peristaltic pump being configured to provide the sheath fluid to the flow cell at a first flow rate; a second fluidic pathway, the second fluidic pathway connecting the flow cell to a receptacle, the second fluidic pathway including a second peristaltic pump, the second peristaltic pump being configured to transport a fluid out of the flow cell at a second flow rate; a third fluidic pathway, the third fluidic pathway connecting the sample probe and the flow cell; a pressure sensor, the pressure sensor configured to sense a pressure corresponding to a pressure in the flow cell; and a processor configured to: receive data representing the pressure sensed by the pressure sensor; and adjust at least one of the first flow rate and the second flow rate.

Another aspect is a flow cytometer comprising: a flow cell for passing particles in a sample; a fluid-driving source in fluid communication with the flow cell, wherein the fluid-driving source is configured to cause a flow of sheath fluid to the flow cell; a pulse attenuation system in fluid communication with the fluid-driving source and the flow cell, wherein the pulse attenuation system is disposed between the fluid-driving source and the flow cell; and a fluidic pathway connects the fluid-driving source and the flow cell, wherein the fluidic pathway bypasses the pulse attenuation system.

Another aspect is a flow cytometer comprising: a flow cell for passing particles in a sample; a fluid-driving source in fluid communication with the flow cell, wherein the fluid-driving source is configured to cause a flow of sheath fluid to the flow cell; a pulse attenuation system in fluid communication with the fluid-driving source and the flow cell, wherein the pulse attenuation system is disposed between the fluid-driving source and the flow cell; and a valve disposed between the flow cell and the pulse attenuation system.

Another aspect is a flow cytometer comprising: a flow cell for passing particles in a sample; a sheath fluid source in fluid communication with the flow cell; a pump disposed between the sheath fluid source and the flow cell, the pump being configured to cause a flow of sheath fluid to the flow cell; a pulse attenuation system in fluid communication with the pump and the flow cell, wherein the pulse attenuation system is disposed between the fluid-driving source and the flow cell; a junction disposed between the sheath fluid source and the pump; a valve disposed between the pulse attenuation system and the flow cell; and a recirculation pathway connecting the junction to the three-way valve, the recirculation pathway including a flow restriction member, wherein the flow restriction member is configured to provide a resistance to flow that corresponds to a resistance to flow of the flow cell.

Another aspect is a particle analyzer comprising: a flow cell for passing particles in a sample; a sample probe in fluid communication with the flow cell; a receptacle in fluid communication with the flow cell; a first peristaltic pump disposed between the sample probe and the flow cell, the first peristaltic pump configured to cause a sample to flow from the sample probe to the flow cell; and a second peristaltic pump disposed between the flow cell and the receptacle, the second peristaltic pump configured to cause fluid to flow from the flow cell to the receptacle.

Another aspect is a flow cytometer comprising: a flow cell for passing particles in a sample; a sample probe in fluid communication with the flow cell; a pump disposed between the sample probe and the flow cell, the pump configured to provide a force to cause the displacement of the sample from the sample probe towards the flow cell; a junction disposed between the pump and the sample probe; and a first fluid-driving source in fluid communication with the junction, the first fluid-driving source configured to provide a flow of a system fluid from the junction to the direction of the sample probe and to the direction of the flow cell.

Another aspect is a method of transporting particles of a sample to a flow cell in a flow cytometer comprising: aspirating a bolus of the sample using a sample probe of the flow cytometer; advancing a portion of the bolus past a connector, the connector in fluid communication with the sample probe, the flow cell, and a reservoir of system fluid; and causing the system fluid to flow from the connector to the direction of the sample probe and to the direction of the flow cell.

Another aspect is a flow cytometer comprising: a flow cell for passing particles in a sample; a sample probe in fluid communication with the flow cell; a pump disposed between the sample probe and the flow cell, the pump configured to provide a force to cause the displacement of the sample from the sample probe towards the flow cell; a junction disposed between the pump and the sample probe; and a first fluid-driving source in fluid communication with the junction, the first fluid-driving source configured to provide a flow of a system fluid from the junction to the direction of the sample probe and to the direction of the flow cell.

DETAILED DESCRIPTION

Figure 1:
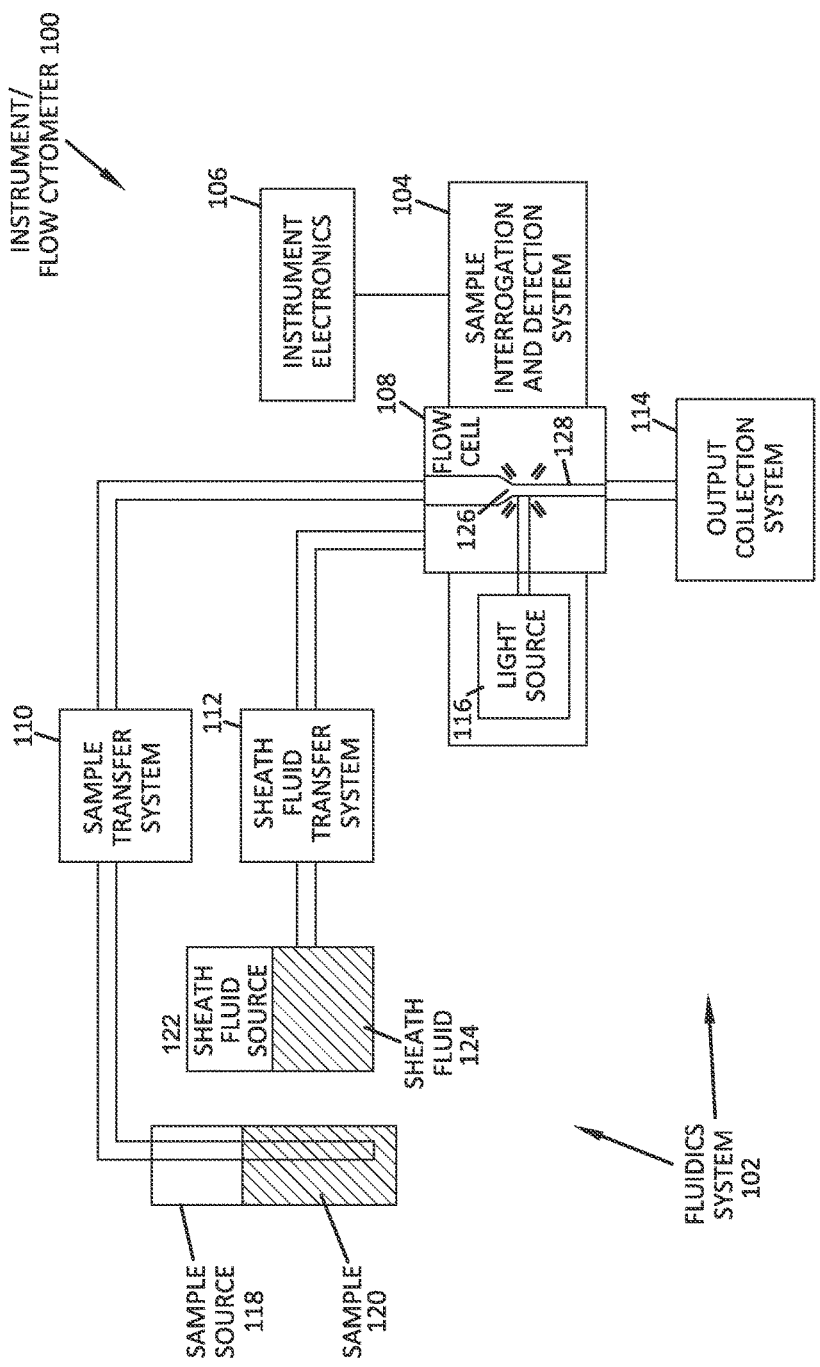
FIG. 1 is a schematic block diagram of an example flow cytometer.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a schematic block diagram of an example instrument 100. In this example, the instrument is a flow cytometer 100 including a fluidics system 102, a sample interrogation and detection system 104, and instrument electronics 106. In some embodiments the fluidics system 102 includes a flow cell 108, a sample transfer system 110, a sheath fluid transfer system 112, and an output collection system 114. The sample interrogation and detection system 104 includes a light source 116. Also shown are the sample source 118 including the sample 120 and the sheath fluid source 122 including the sheath fluid 124. The sheath fluid 124 is an example of a system fluid.

The sample interrogation and detection system 104 is a system configured to interrogate the sample 120 and includes a light source 116 and acquisition electronics. An example of the light source 116 is a laser. Other embodiments of light source 116 are possible as well. The light source 116 illuminates the sample 120. The acquisition electronics detect at least some of the light transmitted, scattered, and/or fluoresced by the sample 120. The light detected by the acquisition electronics can be used to identify the sample 120 or to evaluate properties of the sample 120, including the identity or properties of individual particles in the sample 120.

The instrument electronics 106 operate to control the operation of the flow cytometer 100 and to analyze the content of the sample 120. In some embodiments the instrument electronics 106 is a computing device. A computing device is a physical, tangible device that processes data. Example types of computing devices include personal computers, standalone server computers, blade server computers, mainframe computers, handheld computers, smart phones, special purpose computing devices, and other types of devices that process data.

Computing devices can include at least one central processing unit ("CPU"), a system memory, and a system bus that couples the system memory to the CPU. The system memory includes a random access memory ("RAM") and a read-only memory ("ROM"). A basic input/output system containing the basic routines that help to transfer information between elements within the device, such as during startup, is stored in the ROM. The device further includes a mass storage device. The mass storage device is able to store software instructions and data.

The mass storage device and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device. In some embodiments, the computer-readable data storage media includes non-transitory media.

The computing device can also include an input/output controller for receiving and processing input from a number of other devices, including a keyboard, a mouse, a touch user interface display screen, or another type of input device. Similarly, the input/output controller provides output to a touch user interface display screen, a printer, or other type of output device.

The flow cell 108 includes a stream narrowing device 126 and is configured to prepare a fluid containing the sample 120 for interrogation. The flow cell 108 directs the fluid containing the sample 120 into the stream narrowing device 126, creating an interrogation stream 128. In some embodiments, the interrogation stream 128 also includes sheath fluid 124 surrounding the sample 120.

The light source 116 of the sample interrogation and detection system 104 illuminates the interrogation stream 128. The sample interrogation and detection system 104 detects light transmitted, scattered, and/or fluoresced by the sample to identify the sample and determine its properties. In some embodiments, the sample interrogation and detection system 104 is controlled by the instrument electronics 106. Further, in some embodiments, the sample interrogation and detection system 104 communicates electrical signals corresponding to the light transmitted, scattered, and/or fluoresced by the sample to the instrument electronics 106.

The sample transfer system 110 is a system configured to move the sample 120 from the sample source 118 to the flow cell 108. An example of the sample source 118 is a test tube containing the sample 120. In other embodiments, the sample source 118 is a microplate containing one or more samples. In some embodiments, the sample transfer system 110 is controlled by the instrument electronics 106. Various embodiments of the sample transfer system 110 are described in more detail herein and specifically with reference to FIGS. 3-4, 9-10, and 18.

In some embodiments, the fluidics system 102 includes a sheath fluid transfer system 112. The sheath fluid transfer system 112 is a system configured to deliver sheath fluid 124 from the sheath fluid source 122 to the flow cell 108. In some embodiments, the sheath fluid transfer system 112 is controlled by the instrument electronics 106. As noted above, in some embodiments, the sheath fluid transfer system 112 supplies the sheath fluid 124 to the flow cell 108 where the sheath fluid 124 is incorporated into the interrogation stream 128. Other embodiments do not include a sheath fluid transfer system 112.

The output collection system 114 receives fluid, including the sample 120 and sheath fluid 124, from the flow cell 108 after the sample 120 has been interrogated by the sample interrogation and detection system 104. In some embodiments, the output collection system 114 stores samples for subsequent use or disposal. In some embodiments, the output collection system 114 stores the sample 120 in different locations based on properties of the sample 120 determined by the sample interrogation and detection system 104. In some embodiments, the output collection system 114 is a passive receptacle of fluid that passes through the flow cell 108. In other embodiments, the output collection system 114 actively aspirates fluid from the flow cell 108.

The principles described herein can be implemented in various types of flow cytometers 100 in various possible embodiments. For example, some embodiments involve a sorting flow cytometer, while other embodiments involve a non-sorting flow cytometer. When implemented as a sorting flow cytometer, the flow cytometer 100 typically includes sorting control electronics as part of the instrument electronics 106, a vibration generator coupled to the fluid nozzle (which may be part of or arranged after the flow cell 108, for example), and sorting plates electrically coupled to electrical charge generators, which generate an electric field therebetween to direct drops appropriately as they separate from the interrogation stream 128 into the output collection system 114. The flow cytometer 100 is an example of a particle analyzer.

Figure 2:
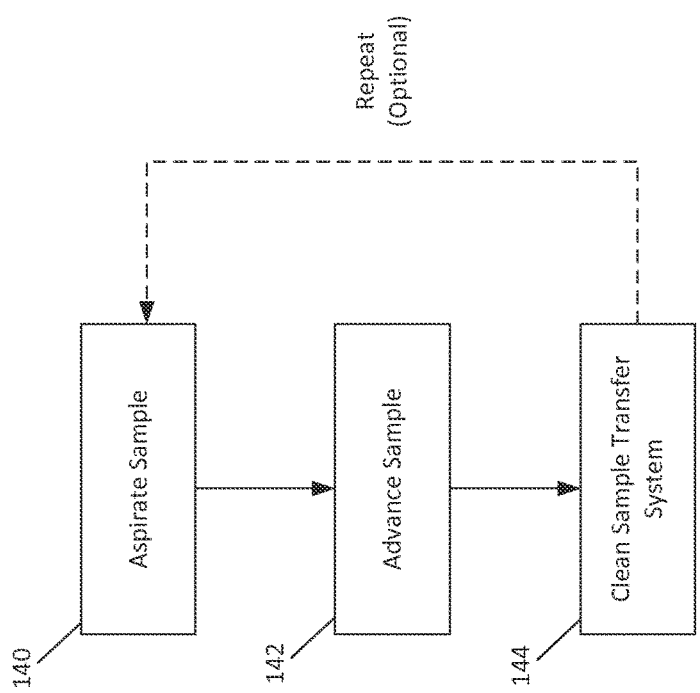
FIG. 2 is a flow chart of an example process for transferring a sample to a flow cell of the flow cytometer using an example fluidics system.

FIG. 2 is a flow chart of an example process for transferring a sample 120 to the flow cell 108 of flow cytometer 100 using an embodiment of the fluidics system 102.

Figure 3:
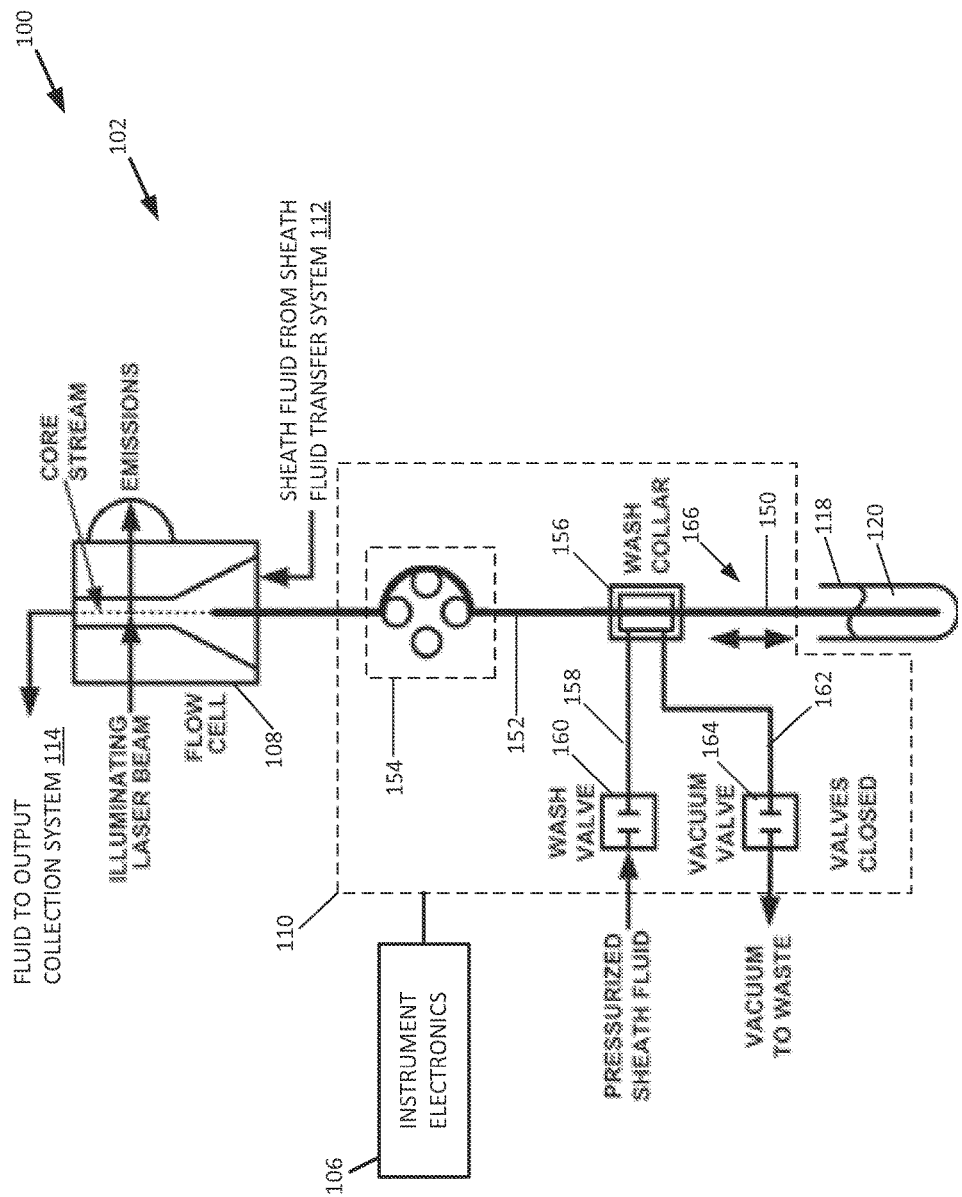
FIG. 3 is a schematic block diagram illustrating additional aspects of an exemplary fluidics system of the flow cytometer including a sample transfer system.
Figure 4:
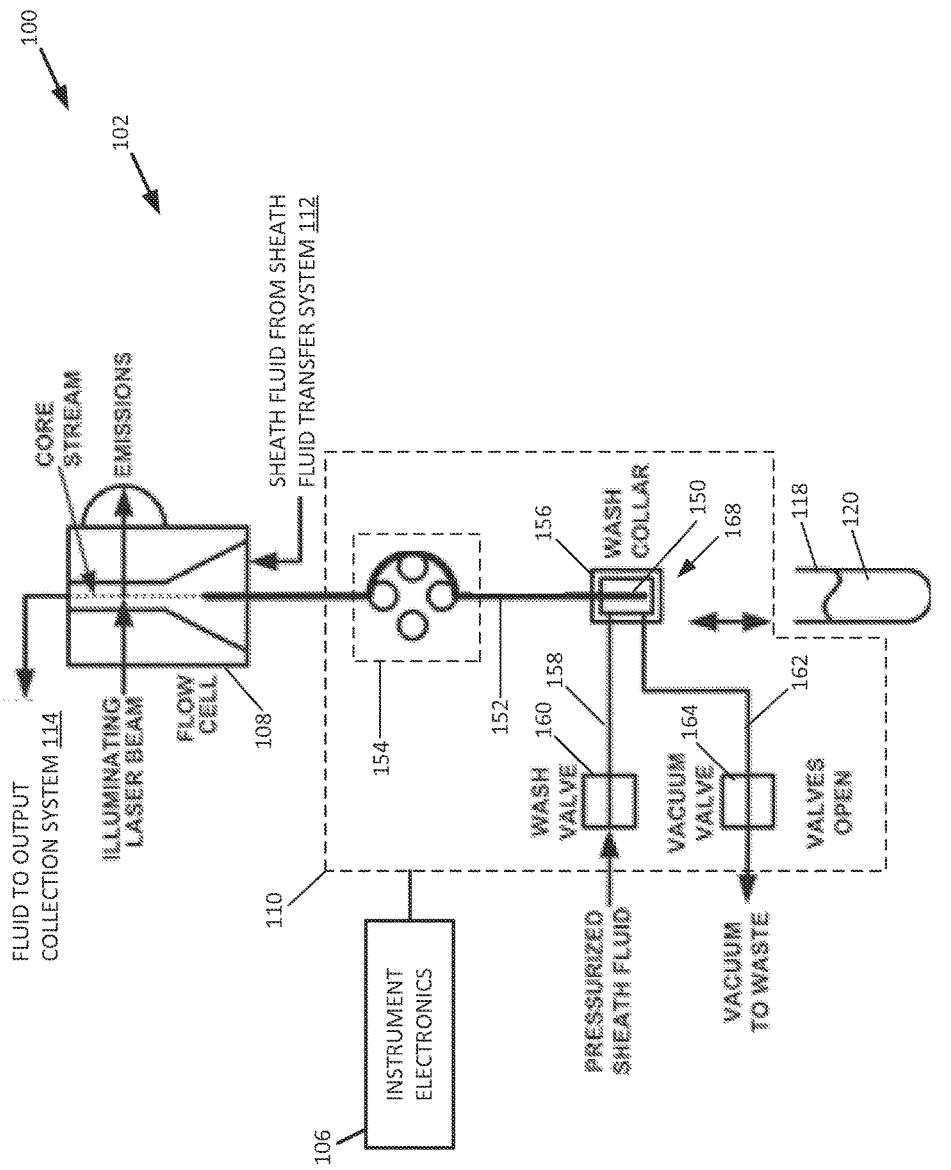
FIG. 4 is a schematic block diagram illustrating additional aspects of a sample transfer system shown in FIG. 3.
Figure 6:
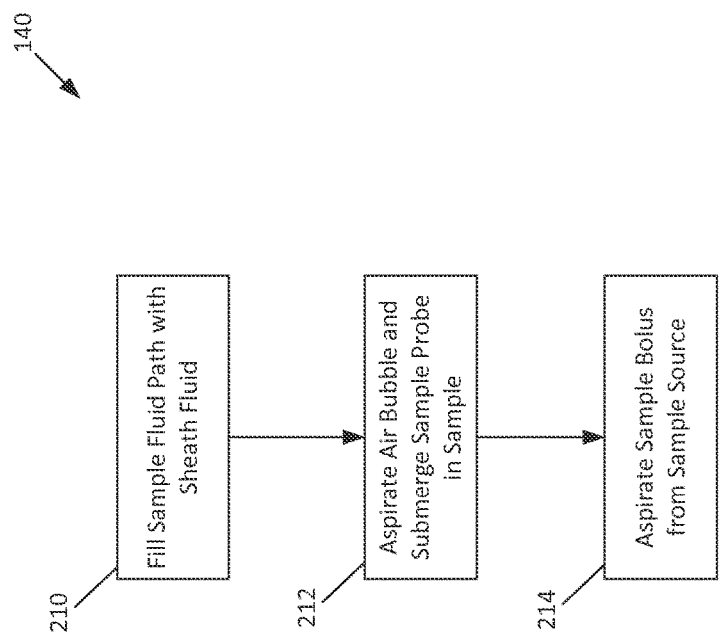
FIG. 6 is a flow chart of an example process of aspirating a sample using the embodiment of the sample transfer system described in FIGS. 3 and 4.

Initially, at step 140, the fluidics system aspirates the sample 120 from the sample source 118 (this step is described in more detail with respect to FIG. 6). FIG. 3 illustrates the sample transfer system 110 aspirating the sample 120. Next, at operation 142, the sample is advanced through the fluidics system and into the flow cell 108 (this step is described in more detail with respect to FIG. 7). FIG. 3 also illustrates the sample transfer system 110 advancing the sample 120. Next, at step 144, at least a portion of the sample transfer system 110 is cleaned by performing a wash process (this step is described in more detail with respect to FIG. 8). Step 144 helps to minimize cross-contamination among consecutive samples. FIG. 4 illustrates the sample transfer system 110 performing the wash process. Finally, the illustrated process can be repeated with a new sample.

FIG. 3 is a schematic block diagram illustrating additional aspects of an exemplary fluidics system 102 of the flow cytometer 100, including an example of the sample transfer system 110. FIG. 3 illustrates the sample transfer system 110 in a configuration to aspirate a sample 120.

As shown in FIG. 1, the example fluidics system 102 includes the flow cell 108, the sample transfer system 110, the sheath fluid transfer system 112, and the output collection system 114. In the example shown in FIG. 3, the sample transfer system 110 includes a sample probe 150, a sample fluid path 152, a sample aspiration pump 154, a wash collar 156, a wash fluid path 158, a wash valve 160, a vacuum path 162, and a vacuum valve 164.

The sample probe 150 is provided in some embodiments to extend into the sample source 118 to receive the sample 120 from the sample source 118. An example of the sample probe 150 is an aspiration needle. The sample probe 150 includes one or more apertures therein through which the sample 120 can be received from the sample source 118.

In some embodiments, the sample probe 150 reciprocates between a lowered position 166 and a raised position 168 (shown in FIG. 4). In the lowered position 166, the tip of the sample probe 150 is submerged in the sample 120 (e.g., a portion of the sample probe 150 is below the liquid level of the sample 120). In the raised position 168, the sample probe 150 is retracted into the wash collar 156, where it can be cleaned during the wash cycle. In some embodiments, the instrument electronics 106 control the selective reciprocation of the sample probe 150 between the lowered position 166 and the raised position 168.

The sample fluid path 152 is a path for conveying the sample 120 through the sample transfer system. An example of the sample fluid path 152 is a silicone tube. In some embodiments, the sample fluid path 152 is formed from multiple silicone tubes. In addition, in some embodiments, the sample fluid path 152 is formed from pressurized tubing (e.g., tubing pressurized to 4 psi). Other embodiments of the sample fluid path 152 are possible as well. The sample fluid path 152 is connected to the sample probe 150 and the flow cell 108. Additionally, in some embodiments, the sample fluid path 152 is connected to the sample aspiration pump 154.

The sample aspiration pump 154 is a device that is configured to move fluid through the sample transfer system 110. The sample aspiration pump 154 is one example of a pressure source. A pressure source is a device that can be configured to create a positive pressure or a negative pressure or both. In some embodiments, the sample aspiration pump 154 is configured to create a vacuum to aspirate the sample 120 from the sample source 118. The sample aspiration pump 154 also creates a positive pressure that pushes the sample 120 into the flow cell 108. An example of sample aspiration pump 154 is a peristaltic pump. An example peristaltic pump is illustrated and described in more detail with reference to FIG. 5. There are many other embodiments of sample aspiration pump 154 as well. Another non-limiting example of the sample aspiration pump 154 is a syringe pump.

The wash collar 156 is a device with an aperture through which the sample probe 150 reciprocates. When the sample probe 150 is in the raised position 168 (as shown in FIG. 4), the tip of the sample probe 150 is disposed in the wash collar 156. The wash collar 156 is in fluid communication with the wash fluid path 158 and the vacuum path 162. The wash collar 156 is an example of a washing member.

The wash fluid path 158 is a path for conveying a fluid from external to the sample transfer system 110 to the wash collar 156. An example of the wash fluid path 158 is a silicone tube. Other embodiments of the wash fluid path 158 are possible as well.

The wash valve 160 is a device that regulates the flow of wash fluid along the wash fluid path 158. The wash valve 160 may be actuated between an open position, which allows wash fluid to flow through the wash fluid path 158, and a closed position, which stops the flow of wash fluid through the wash fluid path 158. In some embodiments, the wash valve 160 is controlled by the instrument electronics 106.

The vacuum path 162 is a path for conveying fluid from the wash collar 156 to a vacuum external to the sample transfer system 110. An example of the vacuum path 162 is a silicone tube. Other embodiments of the vacuum path 162 are possible as well.

The vacuum valve 164 is a device that regulates the flow of fluid along the vacuum path 162. The vacuum valve 164 may be actuated between an open position, which allows fluid to flow through the vacuum path 162, and a closed position, which stops the flow of fluid through the vacuum path 162. In some embodiments, the vacuum valve 164 is controlled by the instrument electronics 106.

During aspiration of the sample 120, both the wash valve 160 and the vacuum valve 164 are closed. Additionally, the sample probe 150 is in the lowered position 166. The sample aspiration pump 154 then retrieves a volume of the sample 120 from the sample source 118 through the sample probe 150 by reducing the pressure in the sample probe 150. The reduced pressure in the sample probe 150 creates a vacuum that pulls sample into the sample probe 150.

During advancement of the sample 120, both the wash valve 160 and the vacuum valve 164 remain closed. Additionally, in some embodiments, the sample probe remains in the lowered position 166. In other embodiments, the sample probe 150 reciprocates to the raised position 168 before or during advancement of the sample 120. The sample aspiration pump 154 continues to create a negative pressure to pull the sample 120 through sample fluid path 152 until the sample 120 reaches the sample aspiration pump 154. After the sample 120 reaches the sample aspiration pump 154, the sample aspiration pump 154 then pushes the sample 120 through the remainder of the sample fluid path 152 and into the flow cell 108.

FIG. 4 is a schematic block diagram illustrating additional aspects of the sample transfer system 110 of FIG. 3. FIG. 4 illustrates the sample transfer system 110 in a configuration to clean the sample transfer system 110.

During cleaning of the sample transfer system 110, both the wash valve 160 and the vacuum valve 164 are opened. Additionally, the sample probe 150 is in the raised position 168. With the wash valve 160 open, a fluid (often sheath fluid) is able to flow through the wash fluid path 158 into the wash collar 156. The fluid contacts the exterior surface of the sample probe 150, washing particles of the sample 120 off of the sample probe 150. Similarly, with the vacuum valve 164 open, the external vacuum creates a vacuum force in the wash collar 156 through vacuum path 162. The fluid and any particles of sample 120 that were removed from the exterior of the sample probe 150 by the fluid are pulled out of the wash collar 156 along the vacuum path 162 by the vacuum.

In some embodiments, the exterior of the sample probe 150 is washed, as described above, while the sample 120 is being advanced into the flow cell 108 and interrogated. By simultaneously washing the exterior of the sample probe 150 and advancing the sample 120, the throughput of the system is increased and the amount of carryover between consecutive samples is decreased. In other embodiments, however, while the exterior of the sample probe 150 is washed, the sample aspiration pump 154 is run in reverse, pulling the sheath fluid 124 from the flow cell 108 through the sample fluid path 152 and the sample probe 150 and into the wash collar 156. This sheath fluid 124 is also removed by being drawn through the vacuum path 162.

The washing operation helps to ensure that samples are not contaminated by particles from previous samples left on the sample probe 150 prior to analysis. Because the fluid used during the wash operation is drawn through the vacuum path 162, it does not contaminate any sample 120 remaining in the sample source 118. Additionally, because the wash collar 156 is disposed along the vertical axis of the sample probe 150, the sample probe 150 does not need to move laterally to a wash station or waste receptacle. Accordingly, the sample transfer system 110 may have the benefits of being simpler and less expensive to build, being more reliable, and having higher throughput.

Figure 5:
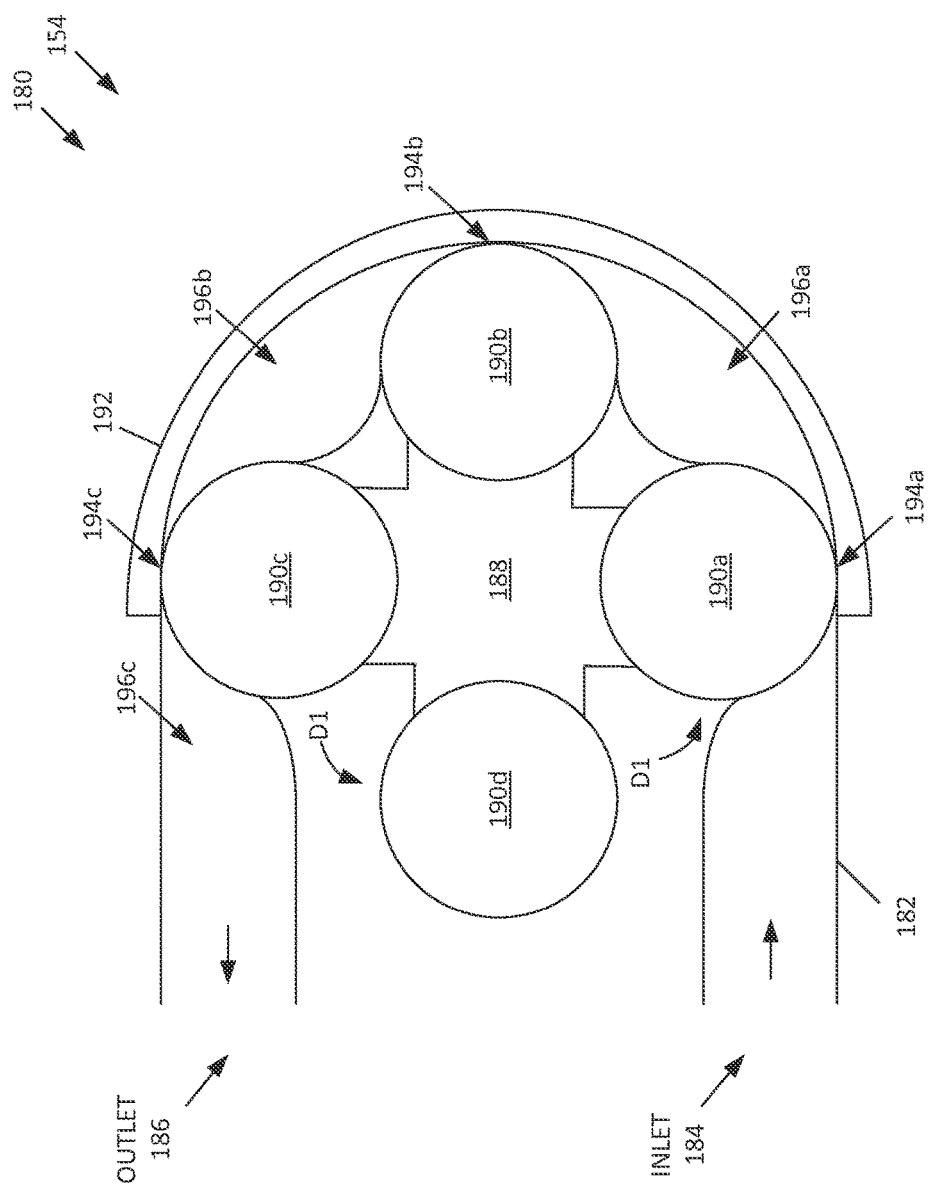
FIG. 5 illustrates an embodiment of a sample aspiration pump.

FIG. 5 is an embodiment of sample aspiration pump 154. In FIG. 5, sample aspiration pump 154 is a peristaltic pump 180. The peristaltic pump 180 includes a flexible tube 182, including an inlet 184 and an outlet 186, a rotational motor 188, one or more rollers 190*a-d* (collectively rollers 190), and a rigid surface 192.

The flexible tube 182 is configured to transport a fluid. In some embodiments, the flexible tube 182 has a cylindrical shape. An example of the flexible tube 182 is a silicone tube. The flexible tube 182 is connected at inlet 184 to a fluid path that is connected to a fluid source. In some embodiments, this fluid path is additional flexible tube that is integral with the flexible tube 182. In other embodiments, the flexible tube 182 is coupled to a separate fluid path. Similarly, the flexible tube 182 is connected at outlet 186 to a fluid path that is connected to a fluid destination. In some embodiments, this fluid path is also additional flexible tube that is integral with the flexible tube 182. In other embodiments, the flexible tube 182 is coupled to a separate fluid path. In some embodiments, the flexible tube 182 forms a U-shape between the inlet 184 and outlet 186, wrapping around the rotational motor 188 and the rollers 190. In some embodiments, a portion of the flexible tube 182 abuts the rigid surface 192.

The rotational motor 188 is a mechanical device that is configured to cause the rollers 190 to rotate around the rotational motor 188. In normal operation, the rotational motor 188 is configured to cause the rollers 190 to rotate in a direction D1. The rotational motor 188 can also be configured to cause the rollers 190 to rotate in a direction opposite to direction D1. In some embodiments, the rotational motor 188 is powered electrically and controlled by the instrument electronics 106.

The rollers 190 are round bodies that are coupled to the rotational motor 188. In some embodiments, the rollers 190 are fixedly coupled to the rotational motor 188. In other embodiments, the rollers 190 are pivotally coupled to the rotational motor 188. As the rotational motor 188 operates, the rollers 190 rotate in direction D1. The rollers 190 pinch the flexible tube 182 against the rigid surface 192 forming the pinch points 194*a-c*. Boluses 196*a-c* of the sample 120 are formed between the pinch points 194*a-c*. As the rollers 190 rotate about the rotational motor 188, the pinch points 194*a-c* move along the flexible tube 182 and in turn push the boluses 196*a-c* through the tube.

Additionally, as the rollers 190 rotate, a vacuum is created at the inlet 184 of the flexible tube 182 that pulls the sample 120 into the peristaltic pump 180. Conversely, as the rollers 190 rotate, a positive pressure is created at the outlet 186 of the flexible tube 182 that expels the sample 120 from the peristaltic pump 180. In this manner, the peristaltic pump 180 moves fluid through the flexible tube 182. When the rollers 190 are rotated in direction D1, this creates forward flow. When the rollers 190 are rotated in the direction opposite to D1, this creates reverse flow. Because the rollers 190 separate the sample 120 alternatingly into boluses 196*a-c* and pinch points 194*a-c*, the flow from the peristaltic pump 180 is pulsating.

There are many benefits to using the peristaltic pump 180 as the sample aspiration pump 154 in the sample transfer system 110. For example, the peristaltic pump 180 has few components and accordingly is inexpensive. Additionally, the peristaltic pump 180 supports the absolute counting of sample particles in a known volume of sample 120 without the use of counting beads because the peristaltic pump 180 is a metering pump that can deliver a known volumetric flow rate of the sample 120 to the flow cell 108.

FIG. 6 is a flow chart of an example process of aspirating a sample using the embodiment of the sample transfer system 110 described in FIGS. 3 and 4.

Initially, at step 210, the sample fluid path 152 is filled with sheath fluid. In some embodiments, the sheath fluid is pulled from the flow cell 108 into the sample transfer system 110 by the sample aspiration pump 154 operating in a direction opposite of D1. The sample probe 150 is positioned in the raised position 168. Both the wash valve 160 and vacuum valve 164 are closed.

Next, at step 212, the sample probe 150 begins to reciprocate to the lowered position 166. As the sample probe 150 reciprocates, the sample aspiration pump 154 is activated to create a vacuum in the sample probe 150. A controlled volume of air is aspirated into the sample fluid path 152 before the tip of the sample probe 150 is submerged in the sample 120.

Next, at step 214, a bolus of sample 120 is aspirated into the sample fluid path 152 by running the sample aspiration pump 154.

Figure 7:
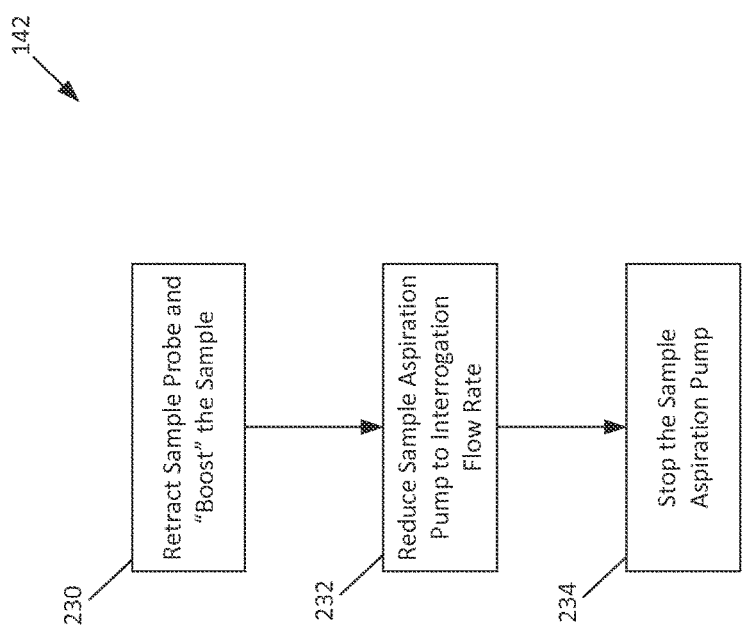
FIG. 7 is a flow chart of an example process of advancing a sample using the embodiment of the sample transfer system described in FIGS. 3 and 4.

FIG. 7 is a flow chart of an example process of advancing a sample using the embodiment of the sample transfer system 110 described in FIGS. 3 and 4.

Initially, at step 230, the sample probe 150 is reciprocated back to the raised position 168. Simultaneously, the sample 120 is boosted through the sample fluid path 152 by running the sample aspiration pump 154 at a higher flow rate. The boost of the sample 120 is ended when the sample 120 reaches the flow cell 108 and with a volume of the sample 120 remaining in the sample fluid path 152 prior to the sample aspiration pump 154 that is greater than or equal to the volume of sample 120 to be interrogated. This boost reduces the time required to transport the sample 120 to the flow cell 108 and so improves throughput.

Since the tip of the sample probe 150 is moving through air as the sample probe 150 reciprocates to the raised position 168, the sample 120 is followed by air as it is aspirated up the lower portion of the sample fluid path. This is advantageous because it reduces the total volume of sample 120 that must be consumed in order to interrogate a given volume of sample 120. The total volume of sample 120 aspirated should be greater than the sum of (1) the volume of sample 120 entering the flow cell 108 during the boost, (2) the volume of the sample 120 to be interrogated, (3) the volume of the sample fluid path 152 between the sample aspiration pump 154 and the flow cell 108, and (4) the volume of the tubing in the sample aspiration pump 154. If a smaller volume of sample 120 is used, the air following the sample 120 will reach the sample aspiration pump 154 before the sample 120 is completely interrogated. Because air is compressible, the air may interfere with the flow rate of the sample 120 and consequently interfere with the interrogation of the sample 120 as well.

Next, at step 232, the flow rate of the sample aspiration pump 154 is reduced to an interrogation flow rate (i.e., the rate at which the sample interrogation and detection system 104 is capable of interrogating the sample 120). Then after a delay to allow the flow rate to stabilize, the sample interrogation and detection system 104 interrogates the sample 120. The sample aspiration pump 154 continues to operate at the interrogation flow rate until interrogation is complete.

Next, at step 234, the sample aspiration pump 154 is stopped after sample interrogation is complete.

Figure 8:
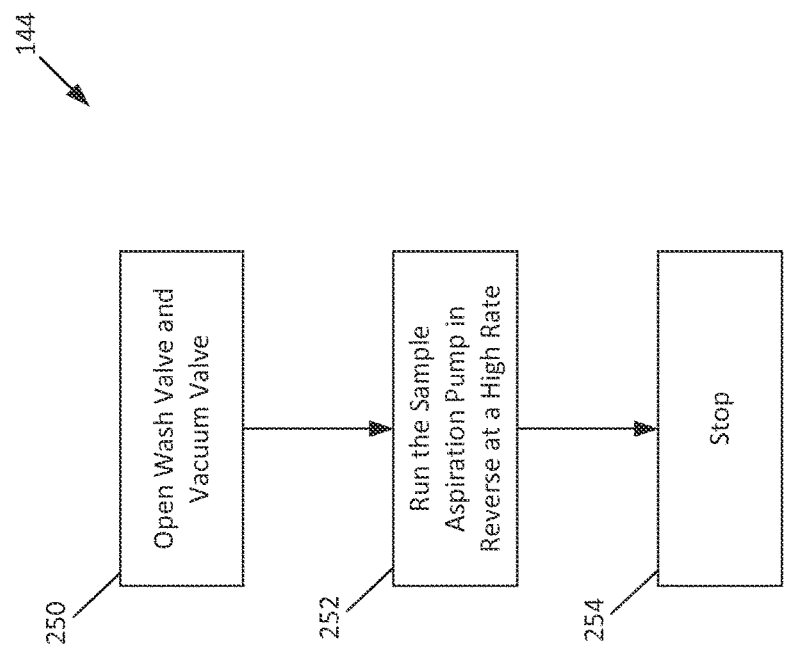
FIG. 8 is a flow chart of an example process of cleaning the sample transfer system using the embodiment of the sample transfer system described in FIGS. 3 and 4.

FIG. 8 is a flow chart of an example process of cleaning the sample transfer system 110 using the embodiment of the sample transfer system 110 described in FIGS. 3 and 4.

Initially, at step 250, the wash valve 160 and vacuum valve 164 are opened to initiate washing of the exterior of the sample probe 150. With the wash valve 160 open, a washing fluid (often sheath fluid) is able to flow through the wash fluid path 158 into the wash collar 156. The washing fluid contacts the exterior surface of the sample probe 150, washing particles of the sample 120 off of the sample probe 150. Similarly, with the vacuum valve 164 open, the external vacuum creates a vacuum force in the wash collar 156 through vacuum path 162. The washing fluid and any particles of sample 120 that were removed from the exterior of the sample probe 150 by the washing fluid are pulled out of the wash collar 156 along the vacuum path 162 by the vacuum.

Next, at step 252, the sample aspiration pump 154 is started in the reverse flow direction at a high flow rate. The sample aspiration pump 154 conveys sheath fluid from the flow cell 108, through the sample fluid path 152, out of the sample probe 150, and into the wash collar 156. This sheath fluid will then be pulled into the vacuum path 162 and evacuated to waste. This reverse pumping flushes the remaining sample 120 out of the sample fluid path 152 to minimize carryover between consecutive samples. In some embodiments, step 250 and 252 are performed simultaneously. Step 250 and step 252 continue for a sufficient time to ensure acceptable carryover of the previous sample into the next sample.

Next, at step 254 the washing operation is stopped. The wash valve 160 and vacuum valve 164 are closed. Additionally, the sample aspiration pump 154 is stopped. The sample transfer system 110 is now clean and ready to begin the process of interrogating the next sample.

Figure 9:
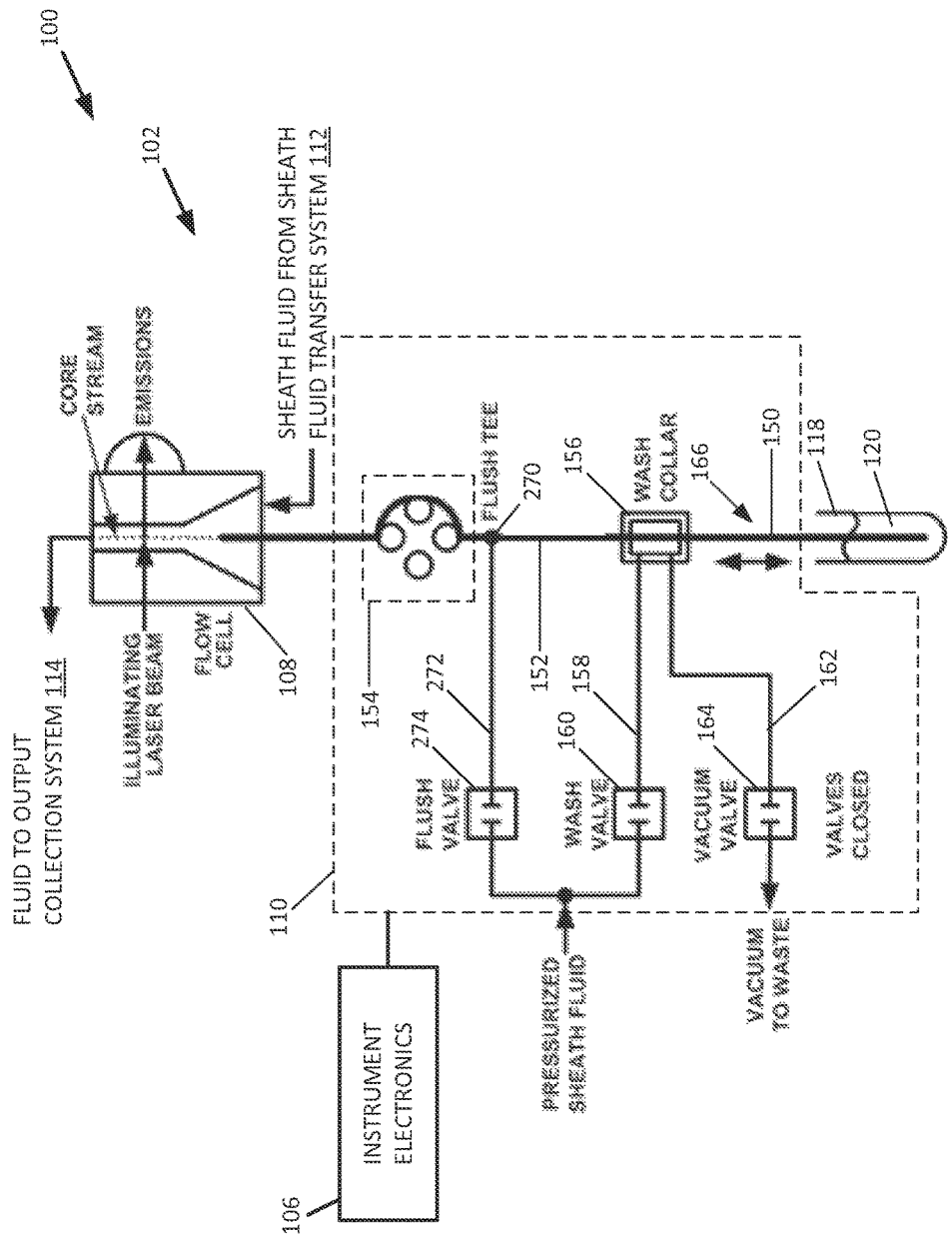
FIG. 9 is a schematic block diagram illustrating additional aspects of an exemplary fluidics system of the flow cytometer, including another example of the sample transfer system.

FIG. 9 is a schematic block diagram illustrating additional aspects of an exemplary fluidics system 102 of the flow cytometer 100, including another example of the sample transfer system 110. FIG. 9 illustrates the sample transfer system 110 in a configuration to aspirate a sample 120.

As shown in FIG. 1, the example fluidics system 102 includes the flow cell 108, the sample transfer system 110, the sheath fluid transfer system 112, and the output collection system 114. In the example shown in FIG. 9, the sample transfer system 110 includes a sample probe 150, a sample fluid path 152, a sample aspiration pump 154, a wash collar 156, a wash fluid path 158, a wash valve 160, a vacuum path 162, a vacuum valve 164, a flush tee 270, flush fluid path 272, and a flush valve 274.

The sample probe 150 is provided in some embodiments to extend into the sample source 118 to receive the sample 120 from the sample source 118. An example of the sample probe 150 is an aspiration needle. The sample probe 150 includes one or more apertures therein through which the sample 120 can be received from the sample source 118.

Figure 10:
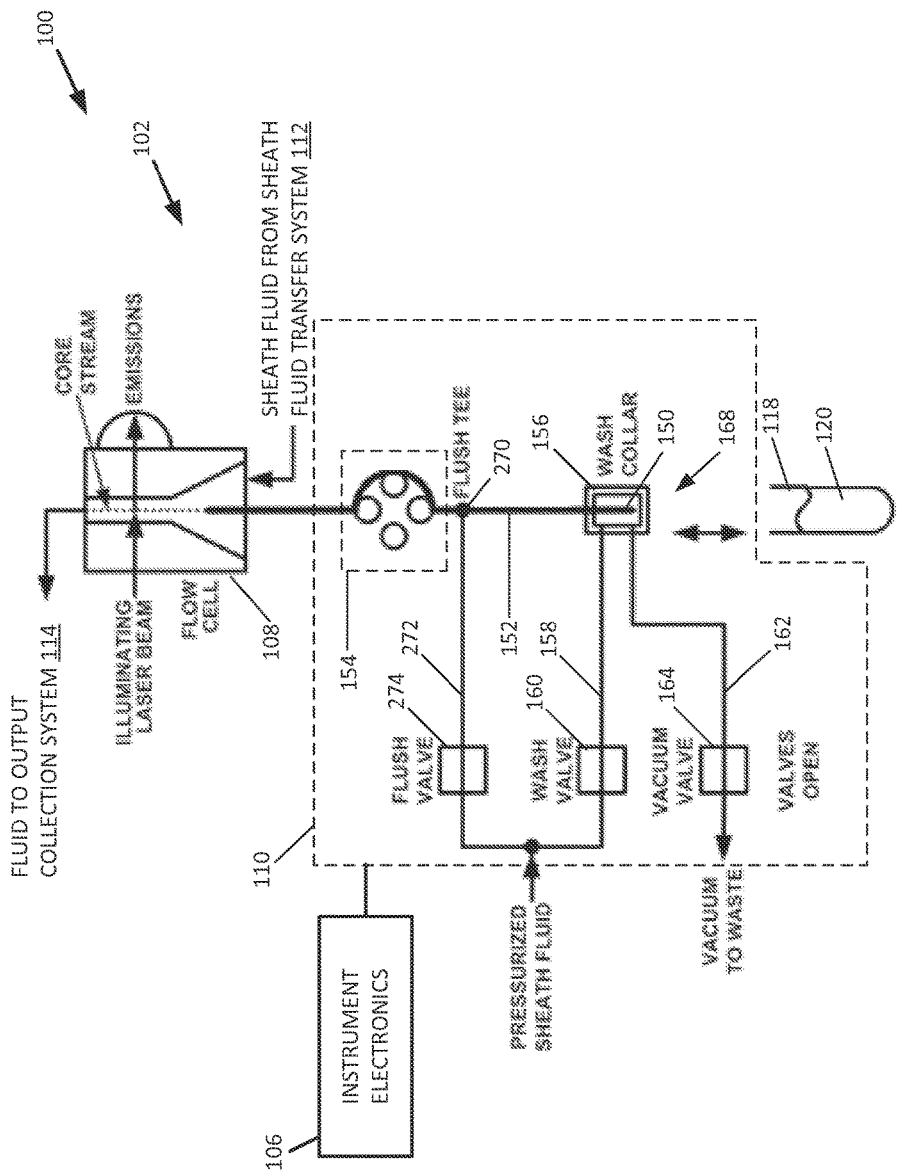
FIG. 10 is a schematic block diagram illustrating additional aspects of the sample transfer system of FIG. 9.

In some embodiments, the sample probe 150 reciprocates between a lowered position 166 and a raised position 168 (shown in FIG. 10). In the lowered position 166, the tip of the sample probe 150 is submerged in the sample 120. In the raised position 168, the sample probe 150 is retracted into the wash collar 156, where it can be cleaned during the wash cycle. In some embodiments, the instrument electronics 106 control the selective reciprocation of the sample probe 150 between the lowered position 166 and the raised position 168.

The sample fluid path 152 is a path for conveying the sample 120 through the sample transfer system 110. An example of the sample fluid path 152 is a silicone tube. In some embodiments, the sample fluid path 152 is formed from multiple silicone tubes. In addition, in some embodiments, the sample fluid path 152 is formed from pressurized tubing (e.g., tubing pressurized to 4 psi). Other embodiments of the sample fluid path 152 are possible as well. The sample fluid path 152 is connected to the sample probe 150 and the flow cell 108. Additionally, in some embodiments, the sample fluid path 152 is connected to the sample aspiration pump 154.

The sample aspiration pump 154 is a device that is configured to move fluid through the sample transfer system 110. In some embodiments, the sample aspiration pump 154 is configured to create a vacuum to aspirate the sample 120 from the sample source 118. The sample aspiration pump 154 also creates a positive pressure that pushes the sample 120 into the flow cell 108. An example of the sample aspiration pump 154 is a peristaltic pump. An example peristaltic pump is illustrated and described in more detail with reference to FIG. 5. There are many other embodiments of sample aspiration pump 154 as well. Another non-limiting example of the sample aspiration pump 154 is a syringe pump.

The wash collar 156 is a device with an aperture through which the sample probe 150 reciprocates. When the sample probe 150 is in the raised position 168 (as shown in FIG. 10), the tip of the sample probe 150 is disposed in the wash collar 156. The wash collar 156 is in fluid communication with the wash fluid path 158 and the vacuum path 162.

The wash fluid path 158 is a path for conveying a fluid from external to the sample transfer system 110 to the wash collar 156. An example of the wash fluid path 158 is a silicone tube. Other embodiments of the wash fluid path 158 are possible as well.

The wash valve 160 is a device that regulates the flow of wash fluid along the wash fluid path 158. The wash valve 160 may be actuated between an open position, which allows wash fluid to flow through the wash fluid path 158, and a closed position, which stops the flow of wash fluid through the wash fluid path 158. In some embodiments, the wash valve 160 is controlled by the instrument electronics 106.

The vacuum path 162 is a path for conveying fluid from the wash collar 156 to a vacuum external to the sample transfer system 110. An example of the vacuum path 162 is a silicone tube. Other embodiments of the vacuum path 162 are possible as well.

The vacuum valve 164 is a device that regulates the flow of fluid along the vacuum path 162. The vacuum valve 164 may be actuated between an open position, which allows fluid to flow through the vacuum path 162, and a closed position, which stops the flow of fluid through the vacuum path 162. In some embodiments, the vacuum valve 164 is controlled by the instrument electronics 106.

The flush tee 270 is a three-way connector with three interconnected internal flow paths. The flush tee 270 connects the flush fluid path 272 to the sample fluid path 152. The flush tee 270 is disposed along the sample fluid path 152 before the sample aspiration pump 154.

The flush fluid path 272 is a path for conveying a fluid from external to the sample transfer system 110 to the sample fluid path 152. An example of the flush fluid path 272 is a silicone tube. Other embodiments of the flush fluid path 272 are possible as well.

The flush valve 274 is a device that regulates the flow of fluid along the flush fluid path 272. The flush valve 274 may be actuated between an open position, which allows fluid to flow through the flush fluid path 272, and a closed position, which stops the flow of fluid through the flush fluid path 272. In some embodiments, the flush valve 274 is controlled by the instrument electronics 106.

During aspiration of the sample 120, the wash valve 160, the vacuum valve 164, and the flush valve 274 are closed. Additionally, the sample probe 150 is in the lowered position 166. The sample aspiration pump 154 then retrieves a volume of the sample 120 from the sample source 118 through the sample probe 150 by reducing the pressure in the sample probe 150. The reduced pressure in the sample probe 150 creates a vacuum that pulls sample into the sample probe 150.

During advancement of the sample 120, both the wash valve 160 and the vacuum valve 164 remain closed. The flush valve 274 initially also remains closed until a sufficient volume of sample 120 has been advanced past the flush tee 270. Then, the flush valve 274 is opened, allowing fluid to flow through the flush fluid path 272 and into the sample fluid path 152. This fluid follows the sample 120 through the sample fluid path 152 and into the sample aspiration pump 154. This fluid takes the place of the air bubble that would otherwise follow the sample 120 through the sample fluid path 152. Because the fluid is uncompressible, the sample aspiration pump 154 will continue to convey the sample 120 to the flow cell 108 without flow variability.

Additionally, during advancement of the sample 120, in some embodiments, the sample probe remains in the lowered position 166. In other embodiments, the sample probe 150 reciprocates to the raised position 168 before or during advancement of the sample 120. The sample aspiration pump 154 continues to create a negative pressure to pull the sample 120 through sample fluid path 152 until the sample 120 reaches the sample aspiration pump 154. After the sample 120 reaches the sample aspiration pump 154, the sample aspiration pump 154 then pushes the sample 120 through the remainder of the sample fluid path 152 and into the flow cell 108.

FIG. 10 is a schematic block diagram illustrating additional aspects of the sample transfer system 110 of FIG. 9. FIG. 10 illustrates the sample transfer system 110 in a configuration to clean the sample transfer system 110.

During cleaning of the sample transfer system 110, the wash valve 160, the vacuum valve 164, and the flush valve 274 are opened. Additionally, the sample probe 150 is in the raised position 168.

With the wash valve 160 open, a fluid (often sheath fluid) is able to flow through the wash fluid path 158 into the wash collar 156. The fluid contacts the exterior surface of the sample probe 150, washing particles of the sample 120 off of the sample probe 150. Similarly, with the vacuum valve 164 open, the external vacuum creates a vacuum force in the wash collar 156 through vacuum path 162. The fluid and any particles of sample 120 that were removed from the exterior of the sample probe 150 by the fluid are pulled out of the wash collar 156 along the vacuum path 162 by the vacuum. The washing operation helps ensure that the samples are not contaminated by particles from previous samples left on the sample probe 150 prior to analysis.

Similarly, with the flush valve 274 open, a fluid (often sheath fluid) is able to flow through the flush fluid path 272, through the flush tee 270, and into the sample fluid path 152. In the sample fluid path 152, part of the fluid flows through the sample aspiration pump 154, into the flow cell 108, and into the output collection system 114 for disposal. The remainder of the fluid in the sample fluid path 152 flows through the sample probe 150, into the wash collar, and through the vacuum path 162 to waste. This washing operation helps ensure that the samples are not contaminated by particles from previous samples left in the sample probe 150 or the sample fluid path 152.

Figure 11:
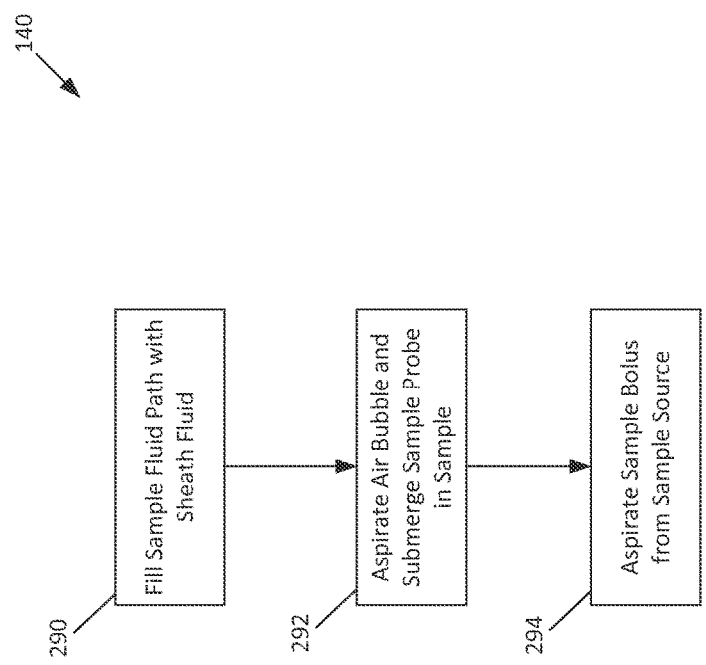
FIG. 11 is a flow chart of an example process of aspirating a sample using the embodiment of the sample transfer system described in FIGS. 9 and 10.

FIG. 11 is a flow chart of an example process of aspirating a sample using the embodiment of the sample transfer system 110 described in FIGS. 9 and 10.

Initially, at step 290, the sample fluid path 152 is filled with sheath fluid. In some embodiments, the sample probe 150 is positioned in the raised position 168 and the flush valve 274 is opened, allowing sheath fluid to flow from the flush fluid path 272 into the sample fluid path 152. A portion of this sheath fluid flows through the sample probe 150 and into the wash collar 156. The vacuum valve 164 is open, drawing the sheath fluid exiting the sample probe 150 through the wash collar 156 and into the vacuum path 162. The remaining sheath fluid from the flush fluid path 272 is aspirated through the sample fluid path 152 and pushed into the flow cell 108 by the sample aspiration pump 154. Once the sample fluid path 152 is filled with sheath fluid, the vacuum valve 164 and flush valve 274 are closed.

In other embodiments, the sample probe 150 is positioned in the raised position 168 and sheath fluid is pulled from the flow cell 108 into the sample fluid path 152 of the sample transfer system 110 by the sample aspiration pump 154 operating in the reverse flow direction. The sheath fluid flows through the entire sample fluid path 152 and exits the sample probe 150. The vacuum valve 164 is open, drawing the sheath fluid exiting the sample probe 150 through the wash collar 156 and into the vacuum path 162. Once the sample fluid path 152 is filled with sheath fluid, the vacuum valve 164 and flush valve 274 are closed.

Next, at step 292, the sample probe 150 begins to reciprocate to the lowered position 166. As the sample probe 150 reciprocates, the sample aspiration pump 154 is activated to create a vacuum in the sample probe 150. A pre-determined volume of air is aspirated into the sample fluid path 152 before the tip of the sample probe 150 is submerged in the sample 120.

Next, at step 294, a bolus of sample 120 is aspirated into the sample fluid path 152 by running the sample aspiration pump 154.

Figure 12:
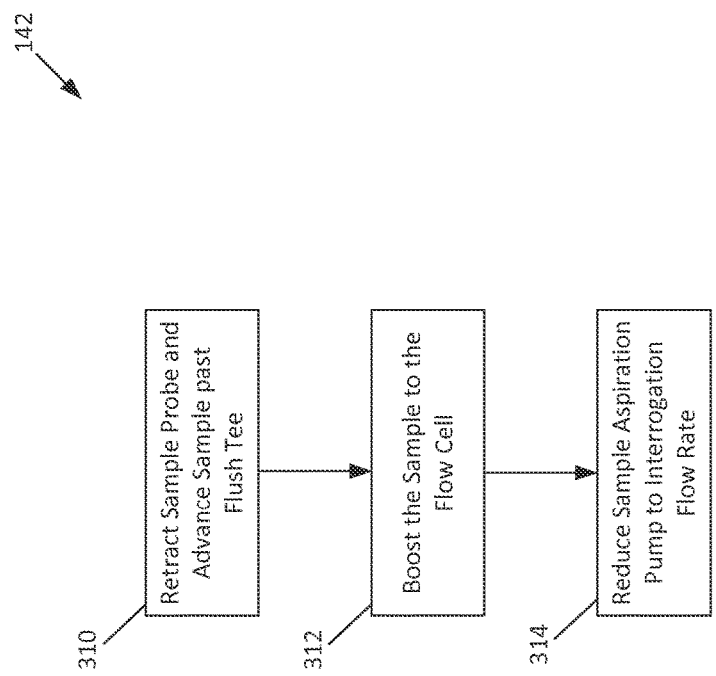
FIG. 12 is a flow chart of an example process of advancing a sample using the embodiment of the sample transfer system described in FIGS. 9 and 10.

FIG. 12 is a flow chart of an example process of advancing a sample using the embodiment of the sample transfer system 110 described in FIGS. 9 and 10.

Initially, at step 310, the sample probe 150 is reciprocated back to the raised position 168. Simultaneously, the sample 120 is advanced through the sample fluid path 152 by running the sample aspiration pump 154 until a portion of the sample 120 has passed the flush tee 270. The portion of the sample 120 that passes the flush tee 270 during this step will be interrogated. In some embodiments, the portion of the sample 120 that passes the flush tee 270 during this step is the entire sample 120 except approximately one microliter. In other embodiments, a larger or smaller portion of sample 120 passes the flush tee 270 during this step. Since the tip of the sample probe 150 is moving through air as the sample probe reciprocates to the raised position 168, the sample 120 is followed by air as it is aspirated up the lower portion of the sample fluid path. This reduces the total volume of sample 120 required. In some embodiments, the portion of sample 120 remaining in the sample fluid path 152 before the flush tee 270 may be detected using a sensor that detects the air in the sample fluid path 152.

Next, at step 312, the sample 120 is boosted through the sample fluid path 152 by running the sample aspiration pump 154 at a higher flow rate. This boost reduces the time required to transport the sample 120 to the flow cell 108 and so improves throughput.

Simultaneously, the wash valve 160, vacuum valve 164, and flush valve 274 are opened. The fluid entering the flush tee 270 from the flush fluid path 272 replaces the portion of the sample 120 that was below the flush tee 270 and the air following it and pushes these into the wash collar 156, thereby washing the portion of the sample fluid path 152 below the flush tee 270 and preventing the air following the sample 120 from entering the sample aspiration pump 154. The portion of the sample 120 that was above the flush tee 270 is followed by fluid into the sample aspiration pump 154. This allows the sample transfer system 110 to aspirate a smaller volume of sample 120 without introducing air into the sample aspiration pump 154 since fluid replaces the air at the flush tee 270.

Because the wash valve 160 and vacuum valve 164 are also open during this step, the exterior of the sample probe 150 is washed in the wash collar 156 while the sample 120 is still being advanced. Similarly, some of the fluid entering the flush tee 270 from the flush fluid path 272 flows down the sample fluid path 152 and into the sample probe 150, washing the portion of the sample fluid path 152 downstream of the flush tee 270 and the interior of the sample probe 150 while the sample 120 is still being advanced.

The boost of sample 120 ends when the sample 120 reaches the flow cell 108. Because the sample 120 is followed by fluid rather than air, the boost can continue even if the volume of sample 120 remaining in the sample fluid path 152 prior to the sample aspiration pump 154 is less than the volume of sample 120 to be interrogated. This reduces the minimum volume of sample 120 required by the sample transfer system 110.

Next, at step 314, the flow rate of the sample aspiration pump 154 is reduced to an interrogation flow rate (i.e., the sample flow rate at which the sample interrogation and detection system 104 is capable of interrogating the sample 120). Then after a delay to allow the flow rate to stabilize, the sample interrogation and detection system 104 interrogates the sample 120. The sample aspiration pump 154 continues to operate at the interrogation flow rate until interrogation is complete.

Figure 13:
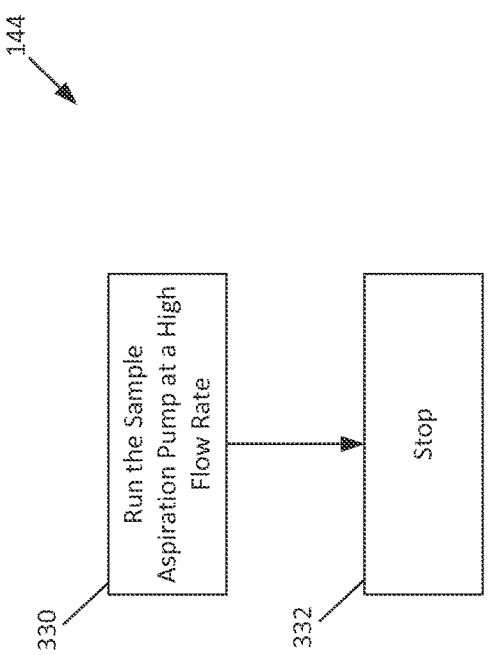
FIG. 13 is a flow chart of an example process of cleaning the sample transfer system using the embodiment of the sample transfer system described in FIGS. 9 and 10.

FIG. 13 is a flow chart of an example process of cleaning the sample transfer system 110 using the embodiment of the sample transfer system 110 described in FIGS. 9 and 10.

Next, at step 330, the sample aspiration pump 154 is run at a high flow rate while the wash valve 160, the vacuum valve 164, and the flush valve 274 remain open. This pulls fluid from the flush fluid path 272 through the flush tee 270 and the upper portion of the sample fluid path 152, including the sample aspiration pump 154. This fluid is then pushed out of the sample transfer system 110 and into the flow cell 108. This process flushes and cleans the sample fluid path 152 and flow cell 108 to minimize cross-contamination between consecutive volumes of sample 120. Step 330 is continued for a sufficient time to ensure acceptable carryover of the previous sample into the next sample.

Next, at step 332 the washing operation is stopped. The wash valve 160, vacuum valve 164, and flush valve 274 are closed. Additionally, the sample aspiration pump 154 is stopped. The sample transfer system 110 is now clean, filled with sheath fluid, and ready to begin the process of interrogating the next sample.

There are many benefits to the embodiment of the sample transfer system 110 described in FIGS. 9 and 10 and the process described in FIGS. 11-13. For example, because fluid replaces the aspirated air following the sample 120 through the flush tee 270, the sample transfer system 110 can aspirate a smaller volume of sample 120 without introducing air into the sample aspiration pump 154, thus reducing the amount of sample required for analysis. Moreover, washing the interior of the sample probe 150 and the portion of the sample fluid path 152 downstream of the flush tee 270 while the sample 120 is still being advanced allows more efficient washing of these components. In some embodiments, the sample transfer system 110 can aspirate a volume of sample 120 that is less than twenty-five microliters. The sample transfer system 110 has few components and, accordingly, is inexpensive. The washing cycle minimizes carryover of particles between samples. The sample transfer system 110 provides for high throughput due, in part, to the simultaneous washing and interrogation operations. The vacuum generated by the sample aspiration pump 154 at the tip of sample probe 150 enables sample 120 to be aspirated from a wide variety of sample source 118 vessels. Use of a bi-directional positive displacement pump, such as a peristaltic pump, for the sample aspiration pump 154 enables sample 120 to be resuspended by alternately aspirating and then dispensing a bolus of sample 120 in the sample source 118.

Figure 14:
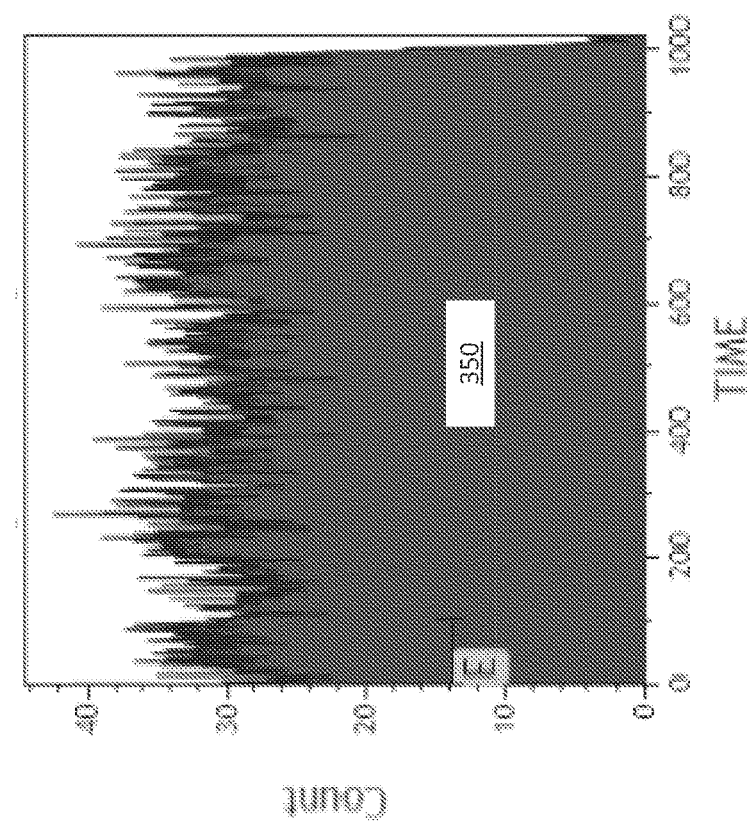
FIG. 14 shows a graph of an example output from an embodiment of flow cytometer including a fluid transport system.

FIG. 14 shows a graph of an example output from an embodiment of flow cytometer 100 including a sample transfer system 110. The output graph is generated from an embodiment of a sample transfer system 110 in which sample aspiration is performed using a conventional air-over-water pressurization system of sample transport.

In this graph, the x-axis corresponds to a time value and the y-axis corresponds to a count value. The graph includes a plurality of vertical bars. Generally, each bar represents a time interval (or bin), during which events (for example, detection of particles of sample 120 by the sample interrogation and detection system 104) are counted. Each bar is positioned along the x-axis at the location that corresponds to the time interval it represents. The height of each bar corresponds to the number of events counted during the time interval it represents. As can be seen in FIG. 14, the graph features a single continuous region 350 where the bars have a similar height, indicating that the number of particles of sample 120 detected during each time interval displayed in the graph is substantially stable and does not fluctuate significantly. In some embodiments of flow cytometer 100, this graph is displayed so that the operator can determine an average count rate being detected and adjust the flow rate to increase or decrease the count rate being detected to a desired count rate. Additionally, the graph can draw the operator's attention to potential flow disruptions or issues that may interfere with the interrogation of sample 120.

Figure 15:
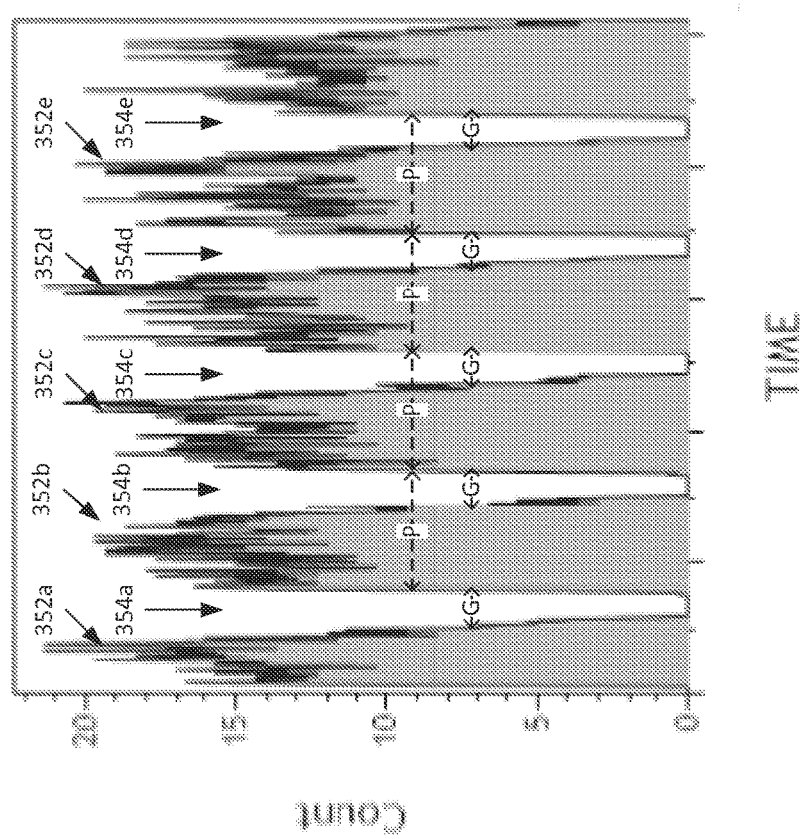
FIG. 15 shows a graph of an example output from an embodiment of flow cytometer including a fluid transport system.

FIG. 15 shows the same type of graph of an example output from an embodiment of flow cytometer 100 including a sample transfer system 110. The output graph is generated from an embodiment of a sample transfer system 110 in which the sample aspiration pump 154 is a peristaltic pump 180 (as shown in FIG. 5).

In this graph, the x-axis corresponds to a time value and the y-axis corresponds to a count value. The graph includes a plurality of vertical bars. Generally, each bar represents a time interval (or bin), during which events (for example, detection of particles of sample 120 by the sample interrogation and detection system 104) are counted. Each bar is positioned along the x-axis at the location that corresponds to the time interval it represents. The height of each bar corresponds to the number of events counted during the time interval it represents.

As described with respect to FIG. 5, the peristaltic pump 180 generates a pulsating output flow. Accordingly, the graph is cyclical and features a plurality of regions of data 352a-c, where particles of sample 120 were detected during the corresponding time intervals, separated by a plurality of gaps 354a-e (collectively gaps 354) where particles of sample 120 were not detected during the corresponding time intervals. As shown in FIG. 5, the graph has a period with duration P and each period includes a gap with duration G. Because the data output from a flow cytometer 100 in which the sample aspiration pump 154 is a peristaltic pump 180 includes gaps, it may be difficult for the operator to determine the average count rate and detect flow disruptions. In some embodiments, this is addressed using the process described in FIGS. 16 and 17.

Figure 16:
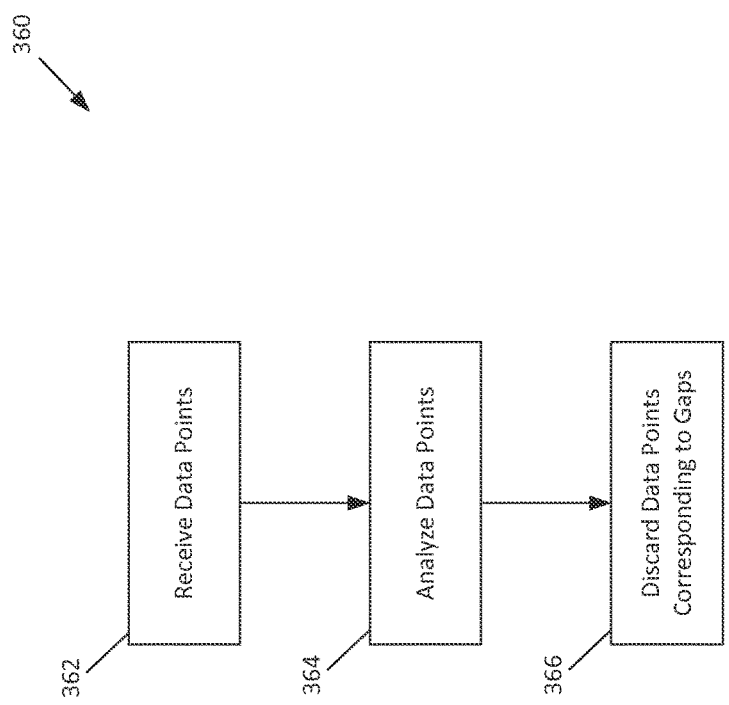
FIG. 16 is a flow chart of an example process of removing the gaps in the output from a flow cytometer using a peristaltic pump in a sample transfer system.

FIG. 16 is a flow chart of an example process 360 of removing the gaps 354 in the output from a flow cytometer 100 using a peristaltic pump 180 in a sample transfer system 110. In some embodiments, the output data of the flow cytometer 100 using a peristaltic pump 180 in a sample transfer system 110 is processed so that it is similar to the output of a flow cytometer that uses a conventional air-over-water pressurization system of sample transport. By processing the output data in this manner, an operator can determine the average count rate and detect flow disruptions in the same manner as with a conventional air-over-water pressurization system of sample transport. In some embodiments, process 360 is performed by the instrument electronics 106. In other embodiments, this process 360 is performed by the sample interrogation and detection system 104. Yet other embodiments of process 360 are possible as well.

Initially, at step 362, the data points representing the count values of the number of particles of sample 120 detected by the sample interrogation and detection system 104 during particular time intervals are received.

Next, at step 364, the data points are analyzed to identify gaps 354. In some embodiments, gaps 354 are identified as data points where zero particles of sample 120 were detected during the corresponding time interval. In other embodiments, gaps 354 are identified as data points where fewer than a threshold value of particles (for example, seven) were detected during the corresponding time interval. Further, in some embodiments, the gaps are analyzed to distinguish gaps due to pulsations from gaps due to other causes (e.g., flow blockage or instrument malfunction). In some embodiments, the duration of the gap is compared to an expected gap duration (e.g., a duration that would be typical for a gap produced by a pulsation) to distinguish gaps due to pulsations from gaps due to other causes. For example, in some embodiments, if the duration of the gap is less than 105-150% of the expected duration of a gap due to a pulsation, the gap is identified as a gap due to a pulsation. In other embodiments, a different threshold may be used. Additionally, in some embodiments, the location of the gap within the period of the graph is also used to distinguish gaps due to pulsations from gaps due to other causes.

Finally, at step 366, the data points corresponding to gaps 354 are discarded. In some embodiments, the data points are permanently deleted. In other embodiments, the data points are merely hidden during subsequent data output or graphing operations. Further, in some embodiments, the time coordinates of the data points that are not discarded are remapped so that it appears as though the gaps 354 never existed. In some embodiments, only the gaps 354 that are identified as being related to pulsations are removed. Other gaps, such as those related to flow blockage or instrument malfunction, are not discarded and are displayed. In this manner, the operator may be alerted to a potential system problem.

Figure 17:
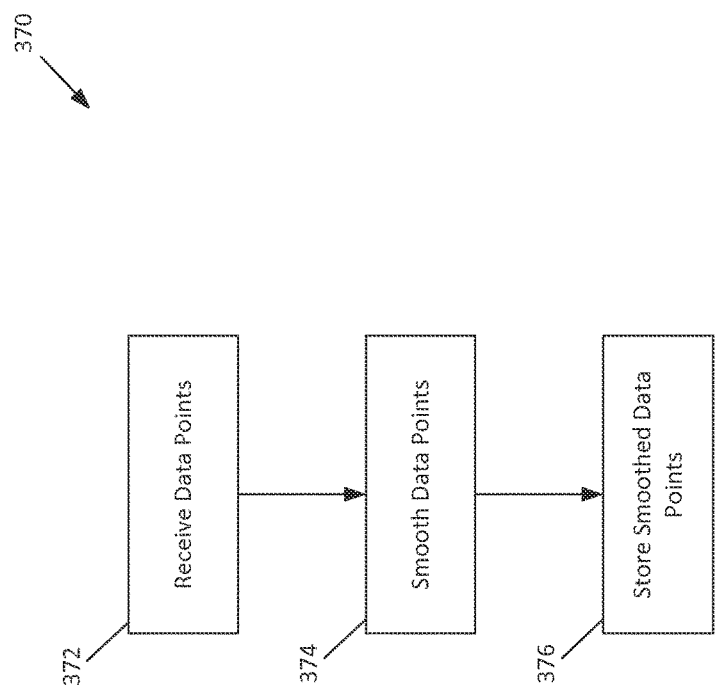
FIG. 17 is a flow chart of an example process of smoothing the output data from a flow cytometer using a peristaltic pump in a sample transfer system.

FIG. 17 is a flow chart of an example process 370 of smoothing the output data from a flow cytometer 100 using a peristaltic pump 180 in a sample transfer system 110. In this manner, the gaps 354 are filled, at least in part. In some embodiments, the output data of the flow cytometer 100 using a peristaltic pump 180 in a sample transfer system 110 is processed so that it is similar to the output of a flow cytometer that uses a conventional air-over-water pressurization system of sample transport. By processing the output data in this manner, an operator can determine the average count rate and detect flow disruptions in the same manner as with a conventional air-over-water pressurization system of sample transport. In some embodiments, process 370 is performed by the instrument electronics 106. In other embodiments, this process 370 is performed by the sample interrogation and detection system 104. Yet other embodiments of process 370 are possible as well.

Initially, at step 372, the data points representing the count values of the number of particles of sample 120 detected by the sample interrogation and detection system 104 during particular time intervals are received.

Next, at step 374, the count values of the data points are smoothed. In some embodiments, the data points are smoothed by calculating a moving average (or running average) of the count values of the previous data points. For example, in some embodiments, the moving average is calculated as the average of the count value in the previous ten data points. In other embodiments, the moving average is calculated using at least four consecutive time intervals. Other embodiments are possible as well.

Finally, at step 376, the smoothed data points are stored. In some embodiments, the original data points are replaced with the smoothed data points. In other embodiments, both the smoothed data points and the original data points are both stored.

Figure 18:
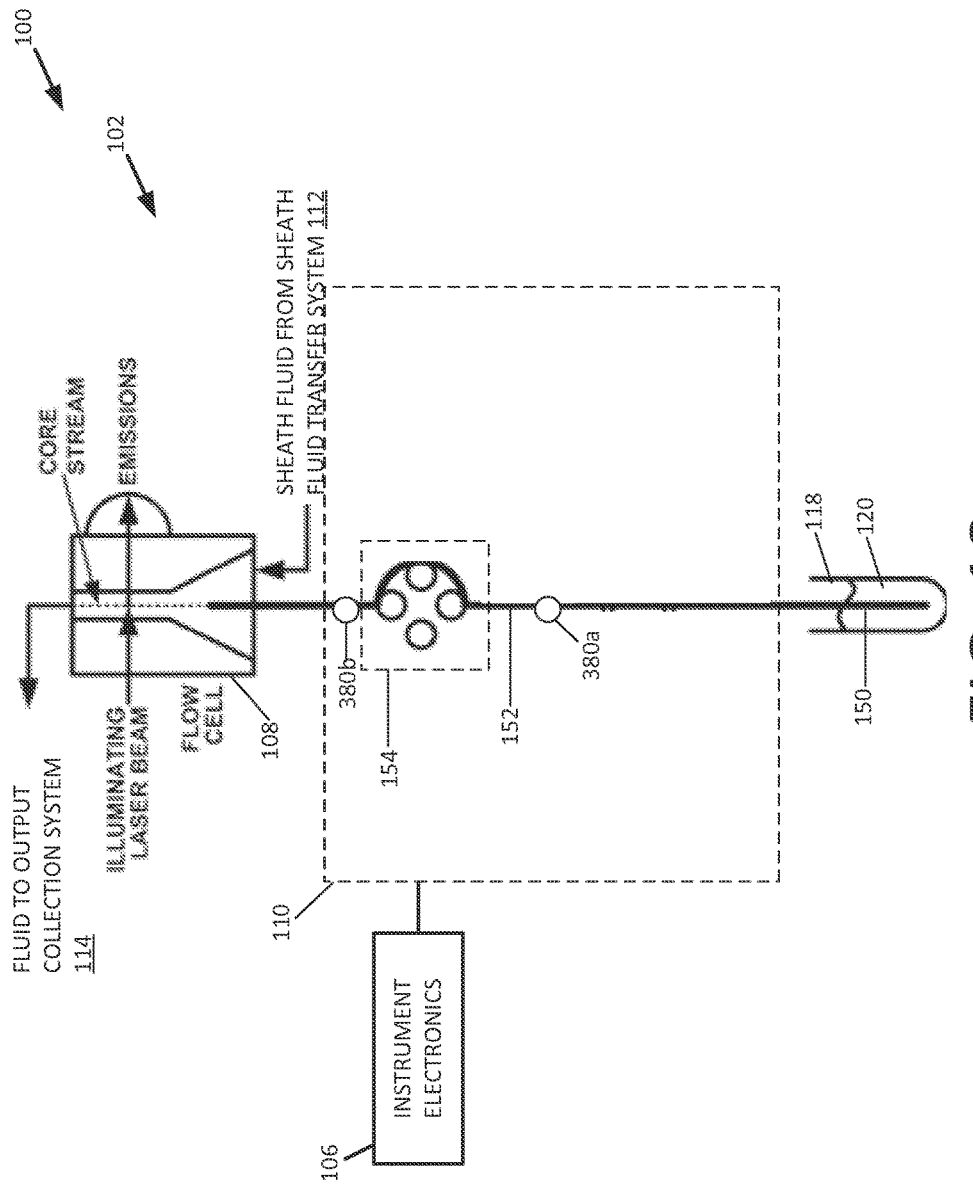
FIG. 18 is a schematic block diagram illustrating additional aspects of an exemplary fluidics system of the flow cytometer, including another example of the sample transfer system.

FIG. 18 is a schematic block diagram illustrating additional aspects of an exemplary fluidics system 102 of the flow cytometer 100, including another example of the sample transfer system 110. FIG. 18 illustrates the sample transfer system 110 in a configuration to aspirate a sample 120.

As shown in FIG. 1, the example fluidics system 102 includes the flow cell 108, the sample transfer system 110, the sheath fluid transfer system 112, and the output collection system 114. In the example shown in FIG. 18, the sample transfer system 110 includes a sample probe 150, a sample fluid path 152, a sample aspiration pump 154, and one or more vibration devices 380a-b. Although the embodiment shown in FIG. 18 includes two vibration devices 380a-b, other embodiments with more or fewer vibration devices are possible as well. The vibration devices 380a-b are examples of agitators.

The sample fluid path 152 is a path for conveying the sample 120 through the sample transfer system 110. An example of the sample fluid path 152 is a silicone tube. In some embodiments, the sample fluid path 152 is formed from multiple silicone tubes. In addition, in some embodiments, the sample fluid path 152 is formed from pressurized tubing (e.g., tubing pressurized to 4 psi). Other embodiments of the sample fluid path 152 are possible as well. The sample fluid path 152 is connected to the sample probe 150 and the flow cell 108. Additionally, in some embodiments, the sample fluid path 152 is connected to the sample aspiration pump 154. In the embodiment shown in FIG. 18, the sample fluid path is formed from a material that is flexible or semi-flexible.

The vibration devices 380a-b are devices configured to generate vibratory motion. For example, in one potential embodiment each vibration device 380a-b is a small electric motor with an eccentric weight fastened to a rotating shaft. In some embodiments of the vibration devices 380a-b, the small electric motors are direct current powered and operate at a voltage differential of 0.5-1.0 volts. As the motor in the vibration devices 380a-b turns, the eccentric weight imposes an unbalanced rotating centrifugal force on the motor shaft that excites a vibratory motion of the motor housing. Other embodiments of vibration devices 380a-b are possible as well.

In some embodiments, the vibration devices 380a-b include a motor shaft. In other embodiments, the vibration devices 380a-b are shaftless. Further, in some embodiments, the vibration devices 380a-b include piezoelectric crystals.

In some embodiments, the vibration devices 380a-b operate at a frequency range of 150-225 Hz. However, other embodiments of the vibration devices 380a-b that operate at a lower or higher frequency range are possible as well. In some embodiments, the vibration devices 380a-b have an amplitude in the range of 0.7-1.2 G. However, other embodiments of the vibration devices 380a-b that operate at higher or lower amplitude are possible as well.

In some embodiments, the sample 120 flows through the sample fluid path 152 in a laminar flow. A laminar flow is a flow in which a fluid flows in parallel, adjacent layers or stream lines. The individual layers of fluid move in parallel down the length of a flow path and do not intersect each other. Laminar flows often occur at low flow velocities. If a laminar flow occurs, the flow at the center of the sample fluid path 152 may have a higher velocity than the flow near the edges. And in some cases, the flow adjacent to the edge of the sample fluid path 152 does not move at all. When immersed in a laminar flow, particles of the sample 120 tend to migrate to the slower or nonmoving edge flows. Accordingly, if a laminar flow occurs, the particles of sample 120 may be delayed in the sample fluid path 152, and not reach the flow cell 108 during sample interrogation. Because some particles of sample 120 are delayed, the concentration of particles reaching the flow cell 108, and thus the concentration of particles interrogated, is less than that in the sample 120 in the sample source 118, thereby leading to erroneous readings. The laminar flow can cause a significantly lower concentration of particles to be detected when a large sample is being transferred at a low-velocity flow rate.

One or more vibration devices 380a-b are rigidly coupled to the sample fluid path 152. In some embodiments, the vibration device 380a is rigidly coupled to the sample fluid path 152 between the sample probe 150 and the sample aspiration pump 154 and the vibration device 380b is rigidly coupled to the sample fluid path 152 between the flow cell 108 and the sample aspiration pump 154. The vibratory motion generated by the vibration devices 380a-b is transferred to sample fluid path 152. In some embodiments, the vibration devices 380a-b are coupled to the sample fluid path 152 at other locations.

In some embodiments, the vibration devices 380a-b are configured to generate vibratory motion only during sample interrogation. By activating the vibration devices 380a-b, the laminar flow inside the sample fluid path 152 is disrupted and more particles of sample 120 are transferred through the sample fluid path 152. During interrogation, this means that more particles of sample 120 reach the flow cell 108. Therefore, in some embodiments, the flow cytometer 100 more accurately measures particle concentrations and has less loss of sample 120 during analysis.

Additionally, in some embodiments, the vibration devices 380a-b are configured to operate while the sample fluid path 152 is being washed or flushed. In this manner, the vibration devices 380a-b may help minimize carryover between samples. Further, in other embodiments, the vibration devices 380a-b are configured to generate vibratory motion any time a fluid is passing through the fluidics system.

Figure 19:
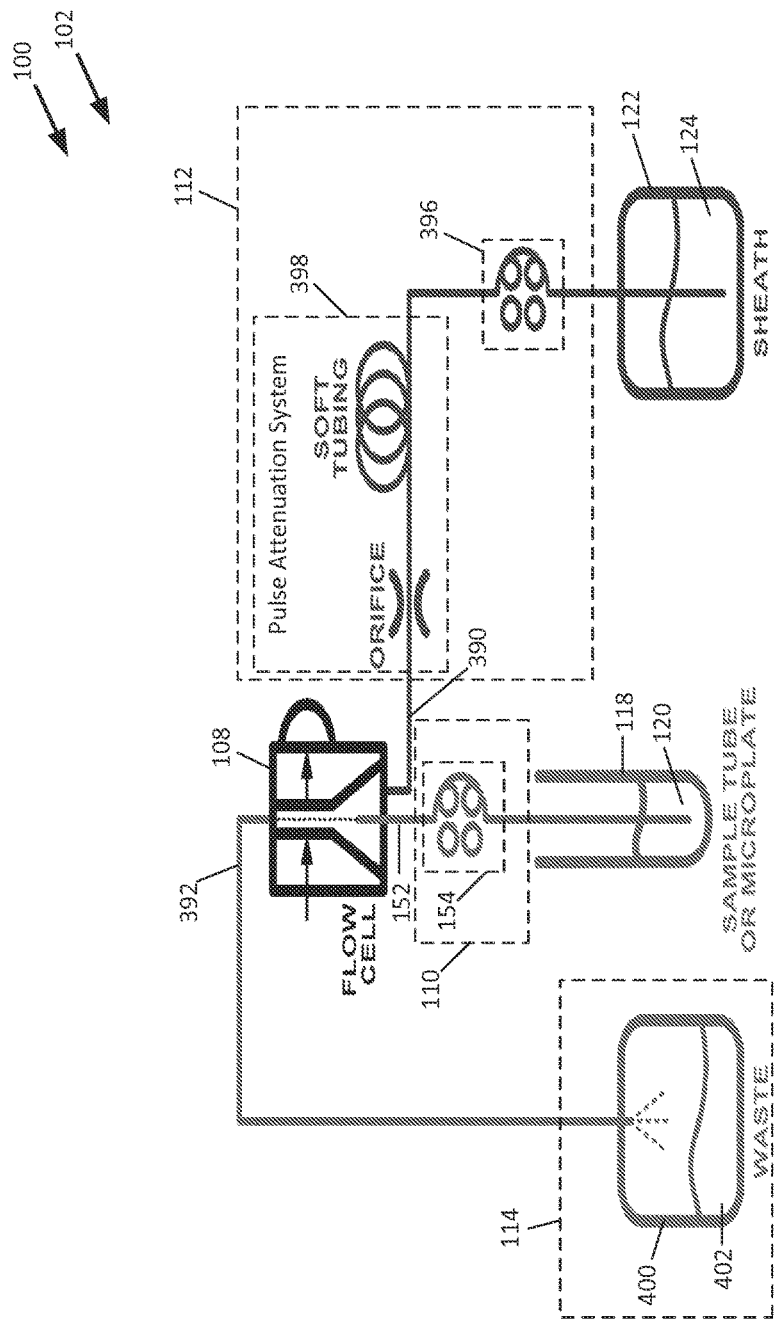
FIG. 19 illustrates another embodiment of the fluidics system of a flow cytometer.

FIG. 19 illustrates another embodiment of the fluidics system 102 of a flow cytometer 100. In this embodiment, the fluidics system 102 includes a flow cell 108, a sample transfer system 110, a sheath fluid transfer system 112, and an output collection system 114. Also shown are the sample source 118 including the sample 120 and the sheath fluid source 122 including the sheath fluid 124.

The flow cell 108 is a device that is configured to prepare a fluid containing the sample 120 for interrogation. In some embodiments, the flow cell 108 is a closed fluidic system and has three fluidic ports. The first fluidic port is connected to the sample fluid path 152, which in turn is connected to the sample transfer system 110. The second fluidic port is connected to the sheath fluid path 390, which in turn is connected to the sheath fluid transfer system 112. The third fluidic port is connected to the output fluid path 392, which in turn is connected to the output collection system 114. Because the flow cell 108 is a closed fluidics system and the fluids are incompressible, only two of the three fluidics ports need to be connected to a system to actively transfer fluid into or out of the port. The third port will passively transfer fluid into or out of the flow cell 108 to balance the other two ports.

In the embodiment shown in FIG. 19, the sample transfer system 110 includes the sample aspiration pump 154, the sheath fluid transfer system 112 includes a sheath aspiration pump 396, and the output collection system 114 does not include a pump for transferring fluid.

The sample transfer system 110 is a system configured to move the sample 120 from the sample source 118 to the flow cell 108. The sample transfer system includes the sample aspiration pump 154. In some embodiments, the sample aspiration pump 154 is a peristaltic pump. Some of the benefits of embodiments that include a peristaltic pump for the sample aspiration pump 154 are described with respect to FIG. 5. Additionally, embodiments that include a peristaltic pump for the sample aspiration pump 154 are capable of resuspending a sample 120 by alternately aspirating and then dispensing a bolus of sample 120 in the sample source 118. Further, because the sample probe 150 reciprocates, it can be lowered into a sample source 118 with an open top (such as a microplate) to aspirate a sample contained therein. In this manner, the sample transfer system 110 supports high-throughput processing of samples by, for example, placing multiple microplates containing samples on a conveyor belt and sequentially lowering the sample probe 150 into each of sample. The use of a peristaltic pump as the sample aspiration pump 154 also enables sample 120 to be aspirated from a wide variety of sample source 118 vessels due to the vacuum generated by peristaltic pump at the tip of the sample probe 150.

The sheath fluid transfer system 112 is a system configured to move the sheath fluid 124 from the sheath fluid source 122 to the flow cell 108. The sheath fluid transfer system 112 includes a sheath aspiration pump 396 and, in some embodiments, a pulse attenuation system 398. In some embodiments, the sheath aspiration pump 396 is a peristaltic pump, an example of which is shown in FIG. 5. The pulse attenuation system 398 is a system configured to dampen or attenuate pulses created by the sheath aspiration pump 396. Embodiments of the pulse attenuation system 398 are described in more detail with respect to FIGS. 22-28. In some embodiments, both the sample aspiration pump 154 and the sheath aspiration pump 396 are peristaltic pumps and the sheath fluid transfer system 112 includes a pulse attenuation system 398, while the sample transfer system 110 does not include a pulse attenuation system. In these embodiments, the flow cytometer 100 interrogates particles of the sample 120 even though the pulses created by the sample aspiration pump 154 are not attenuated by a pulse attenuation system because the pulses in the sample 120 have a negligible impact on the combined flow of sample 120 and sheath fluid 124 through the flow cell 108.

The use of a peristaltic pump to transport sheath decreases the formation of gas bubbles in the flow cell. Using a peristaltic pump to drive sheath fluid places the flow cell and most of the sheath fluid path under positive pressure. Since the sheath fluid in the sheath container is saturated with dissolved atmospheric gases, when it is placed under positive pressure, the dissolved gases become under-saturated and are unlikely to outgas. As a result, the formation of gas bubbles in the flow cell is inhibited.

In the embodiment shown in FIG. 19, the output collection system 114 is a passive system that receives output fluid 402, including the sample 120 and sheath fluid 124, that has been transferred into the flow cell 108 by the sample transfer system 110 and the sheath fluid transfer system 112. The output collection system 114 includes a collection receptacle 400 for containing the output fluid 402. In some embodiments, the output collection system 114 includes multiple receptacles.

Figure 20:
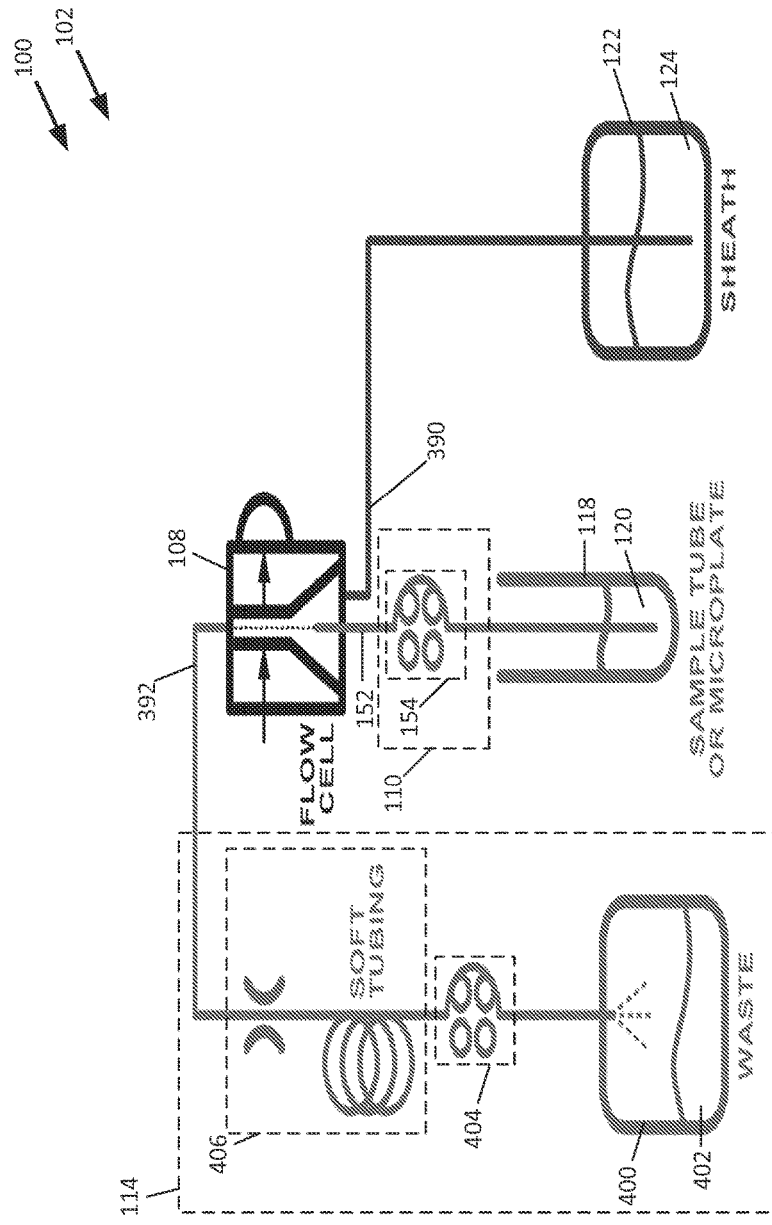
FIG. 20 illustrates another embodiment of the fluidics system of a flow cytometer.

FIG. 20 illustrates another embodiment of the fluidics system 102 of a flow cytometer 100. In this embodiment, the fluidics system 102 includes a flow cell 108, a sample transfer system 110, an output collection system 114, and a sheath fluid path 390. Also shown are the sample source 118 including the sample 120 and the sheath fluid source 122 including the sheath fluid 124.

The flow cell 108 is a device that is configured to prepare a fluid containing the sample 120 for interrogation. In some embodiments, the flow cell 108 is a closed fluidic system and has three fluidic ports. The first fluidic port is connected to the sample fluid path 152, which in turn is connected to the sample transfer system 110. The second fluidic port is connected to the sheath fluid path 390, which in turn is connected to the sheath fluid source 122. The third fluidic port is connected to the output fluid path 392, which in turn is connected to the output collection system 114. Because the flow cell 108 is a closed fluidics system and the fluids are incompressible, only two of the three fluidics ports need to be connected to a system to actively transfer fluid into or out of the port. The third port will passively transfer fluid into or out of the flow cell 108 to balance the other two ports.

In the embodiment shown in FIG. 20, the sample transfer system 110 includes the sample aspiration pump 154, the output collection system 114 includes an output aspiration pump 404, and the sheath fluid path 390 does not include a pump for transferring fluid.

The sample transfer system 110 is a system configured to move the sample 120 from the sample source 118 to the flow cell 108. The sample transfer system includes the sample aspiration pump 154. In some embodiments, the sample aspiration pump 154 is a peristaltic pump. Some of the benefits of embodiments that include a peristaltic pump for the sample aspiration pump 154 are described with respect to FIGS. 5 and 18.

In the embodiment shown in FIG. 20, the output collection system 114 is a system configured to transport output fluid 402 from the flow cell 108 to a collection receptacle 400. The output collection system 114 includes the output aspiration pump 404 and, in some embodiments, a pulse attenuation system 406. In some embodiments, the output aspiration pump 404 is a peristaltic pump, an example of which is shown in FIG. 5. The pulse attenuation system 406 is a system configured to dampen or attenuate pulses created by the output aspiration pump 404. Embodiments of the pulse attenuation system 406 are described in more detail with respect to FIGS. 22-28.

In the embodiment shown in FIG. 20, sheath fluid 124 is passively delivered to the flow cell 108 via the sheath fluid path 390. When the output aspiration pump 404 is active, a vacuum is created in the flow cell 108. The sample aspiration pump 154 occludes the sample fluid path 152, preventing the vacuum from reaching the sample 120. Instead, the vacuum is directed along sheath fluid path 390 and reaches the sheath fluid 124. In this manner, the sheath fluid 124 is provided to the flow cell 108 without an active transport mechanism on the sheath fluid path 390.

Figure 21:
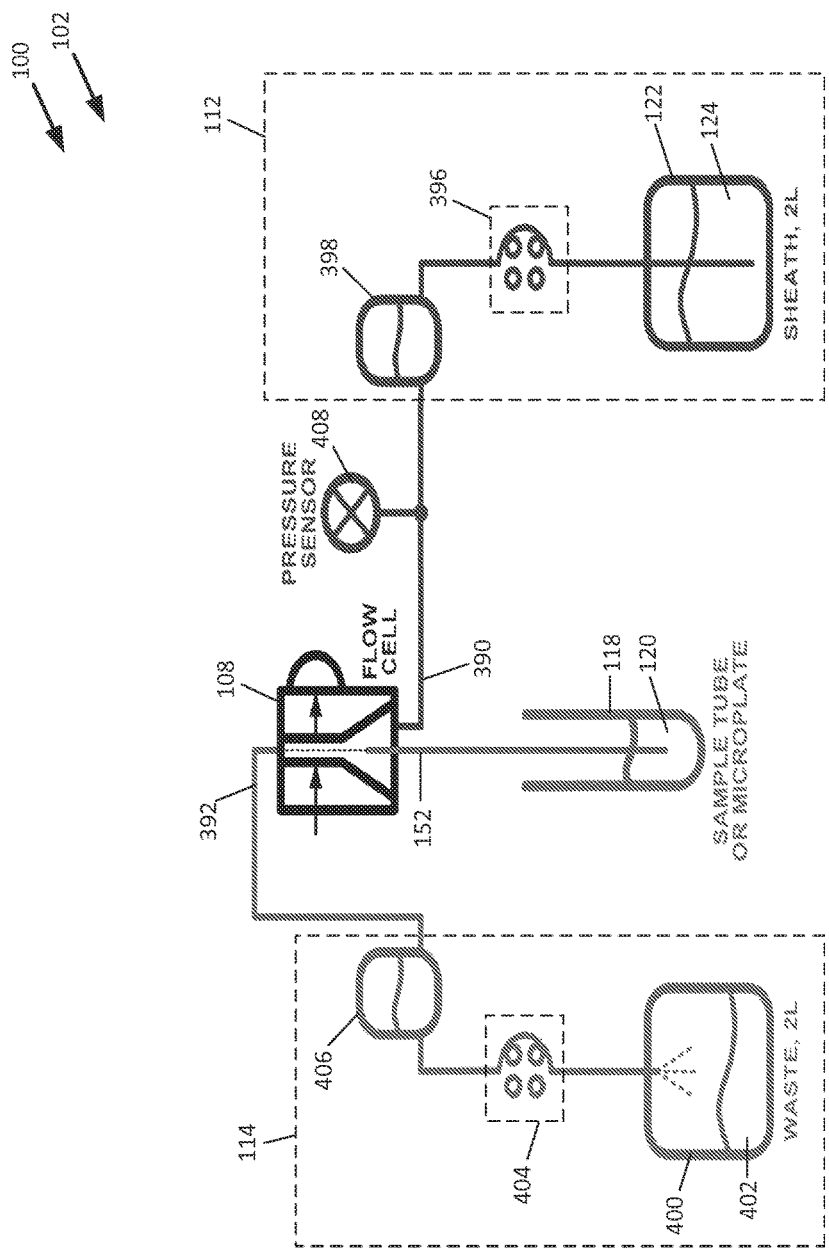
FIG. 21 illustrates another embodiment of the fluidics system of a flow cytometer.

FIG. 21 illustrates another embodiment of the fluidics system 102 of a flow cytometer 100. In this embodiment, the fluidics system 102 includes a flow cell 108, a sheath fluid transfer system 112, an output collection system 114, a sample fluid path 152, and a pressure sensor 408. Also shown are the sample source 118 including the sample 120, the sheath fluid source 122 including the sheath fluid 124, and the collection receptacle 400 including the output fluid 402.

The flow cell 108 is a device that is configured to prepare a fluid containing the sample 120 for interrogation. In some embodiments, the flow cell 108 is a closed fluidic system and has three fluidic ports. The first fluidic port is connected to the sample fluid path 152, which in turn is connected to the sample 120. The second fluidic port is connected to the sheath fluid path 390, which in turn is connected to the sheath fluid transfer system 112. The third fluidic port is connected to the output fluid path 392, which in turn is connected to the output collection system 114. Because the flow cell 108 is a closed fluidics system and the fluids are incompressible, only two of the three fluidics ports need to be connected to a system to actively transfer fluid into or out of the port. The third port will passively transfer fluid into or out of the flow cell 108 to balance the other two ports.

In the embodiment shown in FIG. 21, the sheath fluid transfer system 112 includes the sheath aspiration pump 396, the output collection system 114 includes an output aspiration pump 404, and the sample fluid path 152 does not include a pump for transferring fluid.

The sheath fluid transfer system 112 is a system configured to move the sheath fluid 124 from the sheath fluid source 122 to the flow cell 108. The sheath fluid transfer system 112 includes a sheath aspiration pump 396, and a pulse attenuation system 398. In some embodiments, the sheath aspiration pump 396 is a peristaltic pump, an example of which is shown in FIG. 5. The pulse attenuation system 398 is a system configured to dampen or attenuate pulses created by the sheath aspiration pump 396. Embodiments of the pulse attenuation system 398 are described in more detail with respect to FIGS. 22-28. The pressure sensor 408 senses pressure in the sheath fluid path 390 near the flow cell 108.

In the embodiment shown in FIG. 21, the output collection system 114 is a system configured to transport output fluid 402 from the flow cell 108 to a collection receptacle 400. The output collection system 114 includes the output aspiration pump 404 and, in some embodiments, a pulse attenuation system 406. In some embodiments, the output aspiration pump 404 is a peristaltic pump, an example of which is shown in FIG. 5. The pulse attenuation system 406 is a system configured to dampen or attenuate pulses created by the output aspiration pump 404. Embodiments of the pulse attenuation system 406 are described in more detail with respect to FIGS. 22-28.

In the embodiment shown in FIG. 21, the sample 120 is passively delivered to the flow cell 108 via the sample fluid path 152. When the sheath aspiration pump 396 and the output aspiration pump 404 are active, a vacuum or pressure is created in the flow cell 108 that is equal to the difference in flow rate between the sheath aspiration pump 396 and the output aspiration pump 404. For example, if the flow rate of the output aspiration pump 404 is greater than the flow rate of the sheath aspiration pump 396, a vacuum will be created in the flow cell 108, which will pull the sample 120 into the flow cell 108 through sample fluid path 152. Conversely, if the flow rate of the output aspiration pump 404 is less than the flow rate of the sheath aspiration pump 396, a positive pressure will be created in the flow cell 108, which will push the sheath fluid 124 out of the flow cell 108, through the sample fluid path, and into the sample source 118. In this manner, the sample 120 is provided to the flow cell 108 without an active transport mechanism on the sample fluid path 152.

Typically, the flow rate for sample 120 is 0.1% of the flow rate for the sheath fluid 124. Additionally, the precision of the flow rate of the sample 120 is required to be approximately ±5%. Accordingly, to achieve this flow rate for sample 120, the flow rate of the output aspiration pump 404 must be 100.1% of the flow rate of the sheath aspiration pump 396, which in turn is operating at the flow rate for the sheath fluid 124. Furthermore, the differential flow rate between the sheath aspiration pump 396 and output aspiration pump 404 must be controlled to a precision of approximately ±0.005% in order to achieve the required ±5% precision of the flow rate of the sample 120. It may be expensive or impossible to directly control this differential flow rate to the required degree of precision, so some embodiments include a real time control system to continuously sense the flow rate of sample 120, or a proxy for the flow rate of sample 120, using, for example, a pressure sensor 408, and adjust the flow rates of the sheath aspiration pump 396, the output aspiration pump 404, or both, accordingly.

The pressure sensor 408 is a device that is configured to sense a pressure in the fluidics system 102. In the embodiment shown in FIG. 21, the pressure sensor 408 is disposed on the sheath fluid path 390 near the flow cell 108. In this location, the pressure sensor 408 senses a pressure that approximates the pressure in the flow cell 108. The pressure in the flow cell 108 is related to the differential flow rates between the sheath aspiration pump 396 and the output aspiration pump 404, and controls the flow rate of fluid containing the sample 120 into or out of the flow cell 108. Based on the pressure sensed by the pressure sensor 408, the flow rate of the sheath aspiration pump 396, the output aspiration pump 404, or both are adjusted to achieve the desired flow rate of sample 120. In some embodiments, the pressure sensor 408 may be connected to the instrument electronics 106 to control the flow rates of the sheath aspiration pump 396 and the output aspiration pump 404.

Figure 22:
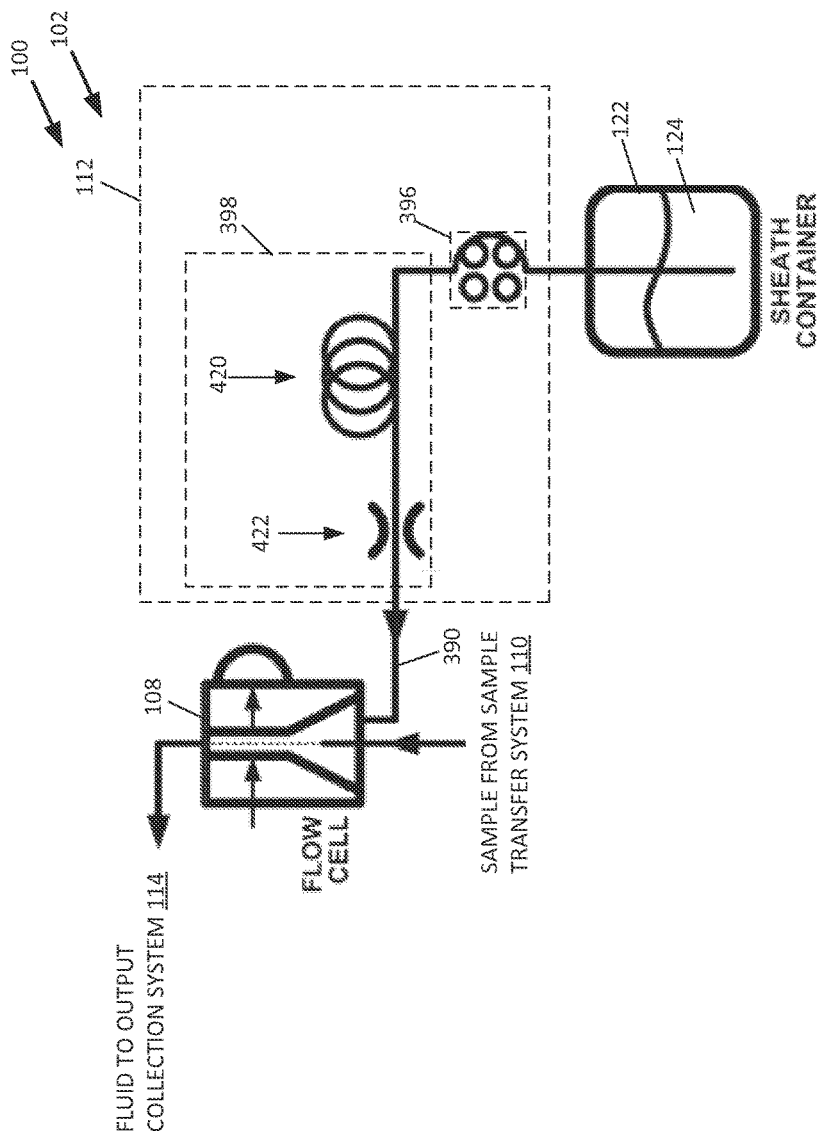
FIG. 22 is a schematic diagram of an embodiment of a pulse attenuation system of a sheath fluid transfer system of the fluidics system of a flow cytometer.

FIG. 22 is a schematic diagram of an embodiment of a pulse attenuation system 398 of a sheath fluid transfer system 112 of the fluidics system 102 of a flow cytometer 100. In this embodiment, the sheath fluid transfer system 112 includes a sheath aspiration pump 396 and a pulse attenuation system 398.

The pulse attenuation system 398 is a system configured to dampen or attenuate pulses created by the sheath aspiration pump 396. For example, in some embodiments, the sheath aspiration pump 396 is a peristaltic pump, the output of which is pulsatile. The pulse attenuation system 398 includes an elastic flow member 420 and a flow restriction member 422.

The elastic flow member 420 is a hollow conduit and is configured to transport sheath fluid 124. The elastic flow member 420 is formed from a material having elastic properties and is configured to expand in response to internal pressure and to contract in the absence of internal pressure. In some embodiments, the elastic flow member 420 is a tube made of a material having elastic properties, such as rubber, silicone, or latex. In some embodiments, the elastic flow member 420 is formed from an elastic tube surrounded by a confined quantity of compressible fluid. Other embodiments of elastic flow member 420 are possible as well.

The flow restriction member 422 is a member that is configured to increase resistance to the flow of a liquid by increasing the back pressure required to achieve a given volumetric flow rate through the flow restriction member 422. In some embodiments, the flow restriction member 422 is an orifice with a smaller inner diameter than the adjacent tubing of the elastic flow member 420 or sheath fluid path 390. In other embodiments, the flow restriction member 422 is a length of tubing with an inner diameter that is smaller than that of the elastic flow member 420. Yet other embodiments of flow restriction member 422 are possible as well.

The elastic flow member 420 and flow restriction member 422 are disposed along the sheath fluid path 390. The flow restriction member 422 is located downstream from the elastic flow member 420. Due to the presence of the flow restriction member 422 downstream, the elastic flow member 420 expands when a flow rate maxima enters it from the sheath aspiration pump 396, and then contracts when a following flow rate minima enters. In this manner, the amplitude of flow rate maxima through the flow restriction member 422 is reduced because some of the peak flow is diverted to expanding the elastic flow member 420. Likewise, the amplitude of the following flow rate minima are increased by the subsequent contraction of the elastic flow member 420, which provides additional flow to supplement the momentarily reduced flow from the sheath aspiration pump 396. In general, the pulse attenuation system 398 reduces the amplitude of flow rate pulsations created by the sheath aspiration pump 396.

Figure 23:
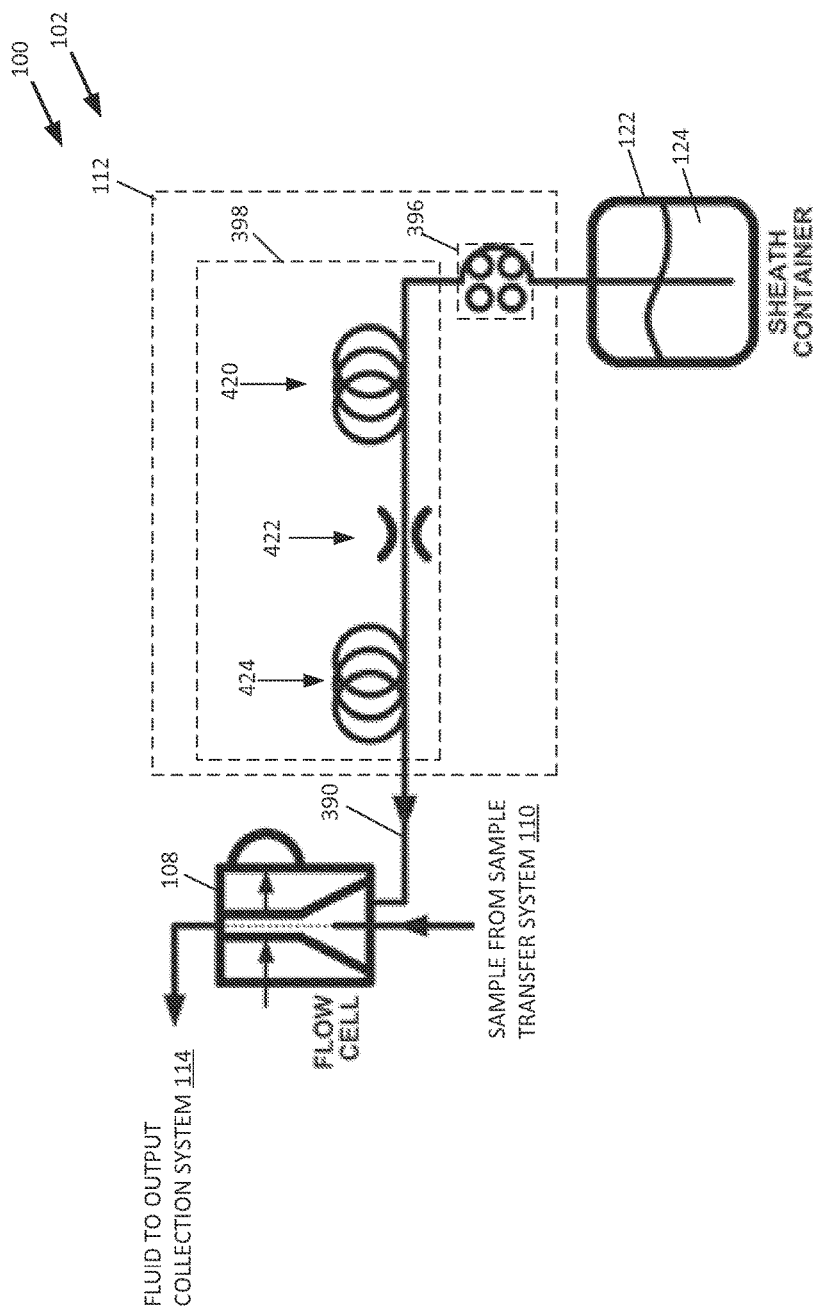
FIG. 23 is a schematic diagram of another embodiment of a pulse attenuation system of a sheath fluid transfer system of the fluidics system of a flow cytometer.

FIG. 23 is a schematic diagram of another embodiment of a pulse attenuation system 398 of a sheath fluid transfer system 112 of the fluidics system 102 of a flow cytometer 100. In this embodiment, the sheath fluid transfer system 112 includes a sheath aspiration pump 396 and a pulse attenuation system 398.

The pulse attenuation system 398 is a system configured to dampen or attenuate pulses created by the sheath aspiration pump 396. For example, in some embodiments, the sheath aspiration pump 396 is a peristaltic pump, the output of which is pulsatile. The pulse attenuation system 398 includes a first elastic flow member 420, a flow restriction member 422, and a second elastic flow member 424.

The embodiment of the pulse attenuation system 398 shown in FIG. 23 functions similarly to the embodiment of pulse attenuation system 398 described in FIG. 22, except that a second elastic flow member 424 is disposed downstream of the flow restriction member 422 to further attenuate pulses remaining in the flow of sheath fluid 124. The first elastic flow member 420 and the flow restriction member 422 are described in greater detail with respect to FIG. 22.

Figure 24:
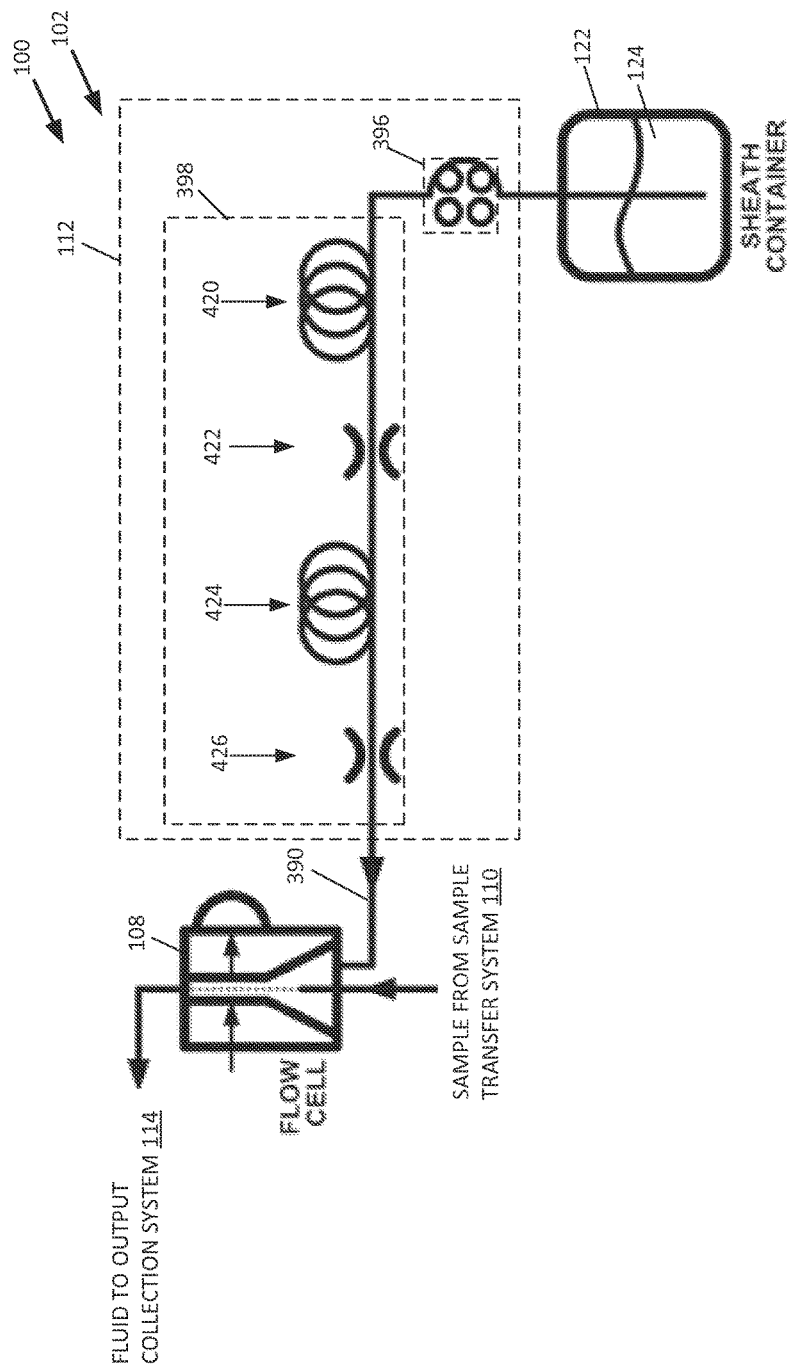
FIG. 24 is a schematic diagram of another embodiment of a pulse attenuation system of a sheath fluid transfer system of the fluidics system of a flow cytometer.

FIG. 24 is a schematic diagram of another embodiment of a pulse attenuation system 398 of a sheath fluid transfer system 112 of the fluidics system 102 of a flow cytometer 100. In this embodiment, the sheath fluid transfer system 112 includes a sheath aspiration pump 396 and a pulse attenuation system 398.

The pulse attenuation system 398 is a system configured to dampen or attenuate pulses created by the sheath aspiration pump 396. For example, in some embodiments, the sheath aspiration pump 396 is a peristaltic pump, the output of which is pulsatile. The pulse attenuation system 398 includes a first elastic flow member 420, a first flow restriction member 422, a second elastic flow member 424, and a second flow restriction member 426.

The embodiment of the pulse attenuation system 398 shown in FIG. 24 functions similarly to the embodiment of pulse attenuation system 398 described in FIG. 22, except that the second elastic flow member 424 and second flow restriction member 426 are disposed downstream of the first flow restriction member 422 to further attenuate pulses remaining in the flow of sheath fluid 124. The first elastic flow member 420 and the first flow restriction member 422 are described in greater detail with respect to FIG. 22. The second elastic flow member 424 and the second flow restriction member 426 operate on the flow of sheath fluid 124 identically to the first elastic flow member 420 and first flow restriction member 422.

Figure 25:
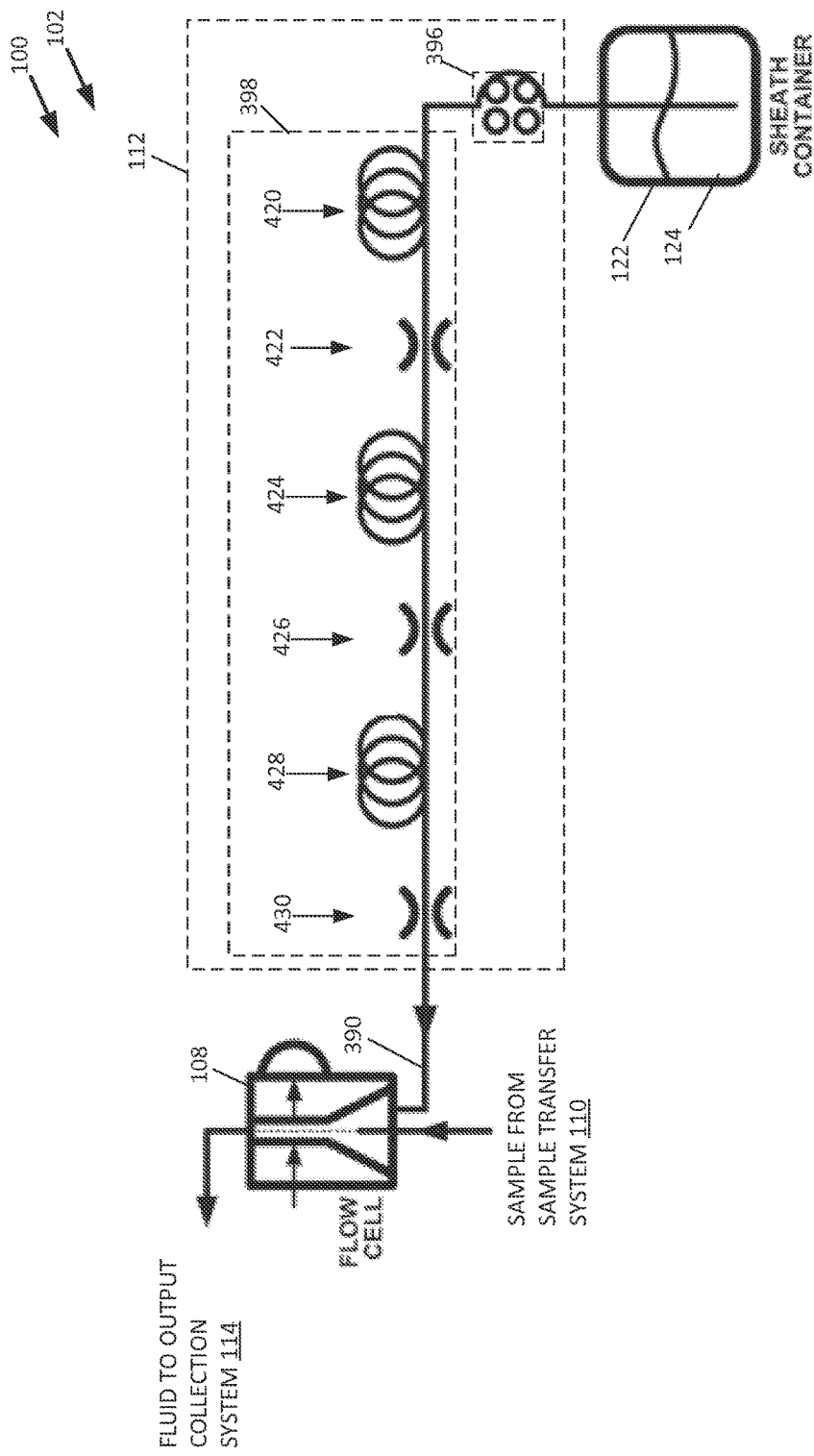
FIG. 25 is a schematic diagram of another embodiment of a pulse attenuation system of a sheath fluid transfer system of the fluidics system of a flow cytometer.

FIG. 25 is a schematic diagram of another embodiment of a pulse attenuation system 398 of a sheath fluid transfer system 112 of the fluidics system 102 of a flow cytometer 100. In this embodiment, the sheath fluid transfer system 112 includes a sheath aspiration pump 396 and a pulse attenuation system 398.

The pulse attenuation system 398 is a system configured to dampen or attenuate pulses created by the sheath aspiration pump 396. For example, in some embodiments, the sheath aspiration pump 396 is a peristaltic pump, the output of which is pulsatile. The pulse attenuation system 398 includes a first elastic flow member 420, a first flow restriction member 422, a second elastic flow member 424, a second flow restriction member 426, a third elastic flow member 428, and a third flow restriction member 430.

The embodiment of the pulse attenuation system 398 shown in FIG. 25 functions similarly to the embodiment of pulse attenuation system 398 described in FIG. 22, except that a second elastic flow member 424, a second flow restriction member 426, a third elastic flow member 428, and a third flow restriction member 430 are disposed downstream of the first flow restriction member 422 to further attenuate pulses remaining in the flow of sheath fluid 124. The first elastic flow member 420 and the first flow restriction member 422 are described in greater detail with respect to FIG. 22. The second elastic flow member 424, the second flow restriction member 426, the third elastic flow member 428, and the third flow restriction member 430 operate on the flow of sheath fluid 124 identically to the first elastic flow member 420 and first flow restriction member 422. In other embodiments, additional elastic flow members and flow restriction members are included in an alternating arrangement.

Figure 26:
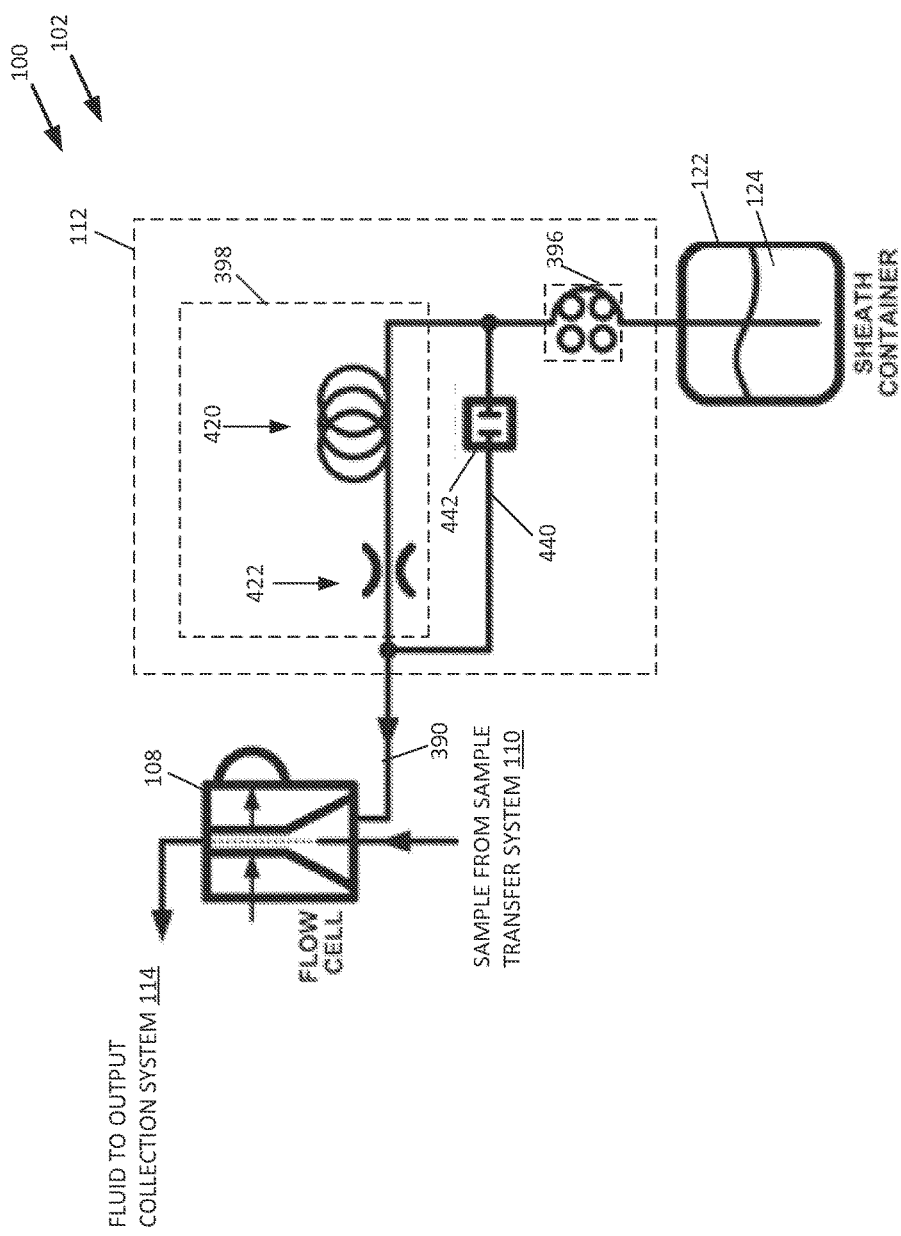
FIG. 26 is a schematic diagram of an embodiment of a sheath fluid transfer system, including a pulse attenuation system and a bypass fluid path, of the fluidics system of a flow cytometer.

FIG. 26 is a schematic diagram of an embodiment of a sheath fluid transfer system 112, including a pulse attenuation system 398 and a bypass fluid path 440, of the fluidics system 102 of a flow cytometer 100. In this embodiment, the sheath fluid transfer system 112 includes a sheath aspiration pump 396, a pulse attenuation system 398, a bypass fluid path 440, and a flush bypass valve 442.

The pulse attenuation system 398 is a system configured to dampen or attenuate pulses created by the sheath aspiration pump 396. For example, in some embodiments, the sheath aspiration pump 396 is a peristaltic pump, the output of which is pulsatile. The pulse attenuation system 398 includes an elastic flow member 420 and a flow restriction member 422. The elastic flow member 420 and the flow restriction member 422 are described in greater detail with respect to FIG. 22.

The bypass fluid path 440 is a path for conveying the sheath fluid 124 from the sheath fluid path 390 downstream of the sheath aspiration pump 396 to the sheath fluid path 390 downstream of the pulse attenuation system 398. The bypass fluid path 440 allows the sheath fluid 124 to bypass the pulse attenuation system 398. An example of the bypass fluid path 440 is a silicone tube. Other embodiments of the bypass fluid path 440 are possible as well.

The flush bypass valve 442 is a device that regulates the flow of sheath fluid 124 along the bypass fluid path 440. The flush bypass valve 442 may be actuated between an open position, which allows the sheath fluid 124 to flow through the bypass fluid path 440, and a closed position, which stops the flow of the sheath fluid 124 through the bypass fluid path 440. In some embodiments, the flush bypass valve 442 is controlled electronically.

In some embodiments, the sheath fluid transfer system 112 is configured to flush air bubbles out of the flow cell 108. In some embodiments, air bubbles are flushed from the flow cell 108 by substantially increasing the flow rate of the sheath aspiration pump 396 and rapidly reversing the direction of sheath aspiration pump 396 several times. The pulse attenuation system 398 interferes with this operation by limiting the maximum flow rate and the speed with which the flow direction can be reversed.

Accordingly, in some embodiments, the flush bypass valve 442 is opened during the process of flushing air bubbles out of the flow cell 108. With the flush bypass valve 442 open, the sheath fluid 124 can bypass the pulse attenuation system 398. Accordingly, with the flush bypass valve 442 open, a higher flow rate and a faster speed for reversing the flow of sheath fluid 124 is enabled. When the flush bypass valve 442 is open, the pulse attenuation system 398 and the bypass fluid path 440 are parallel open flow paths. Because the bypass fluid path 440 has lower flow resistance than the pulse attenuation system 398, the majority of sheath fluid 124 will pass through the bypass fluid path 440. In some embodiments, the bypass fluid path 440 is connected to a separate flush port on the flow cell 108 rather than connecting to the sheath fluid path 390 upstream of the flow cell 108.

During other operations, the flush bypass valve 442 is closed, and the only flow path available to sheath fluid 124 is through the pulse attenuation system 398.

Figure 27:
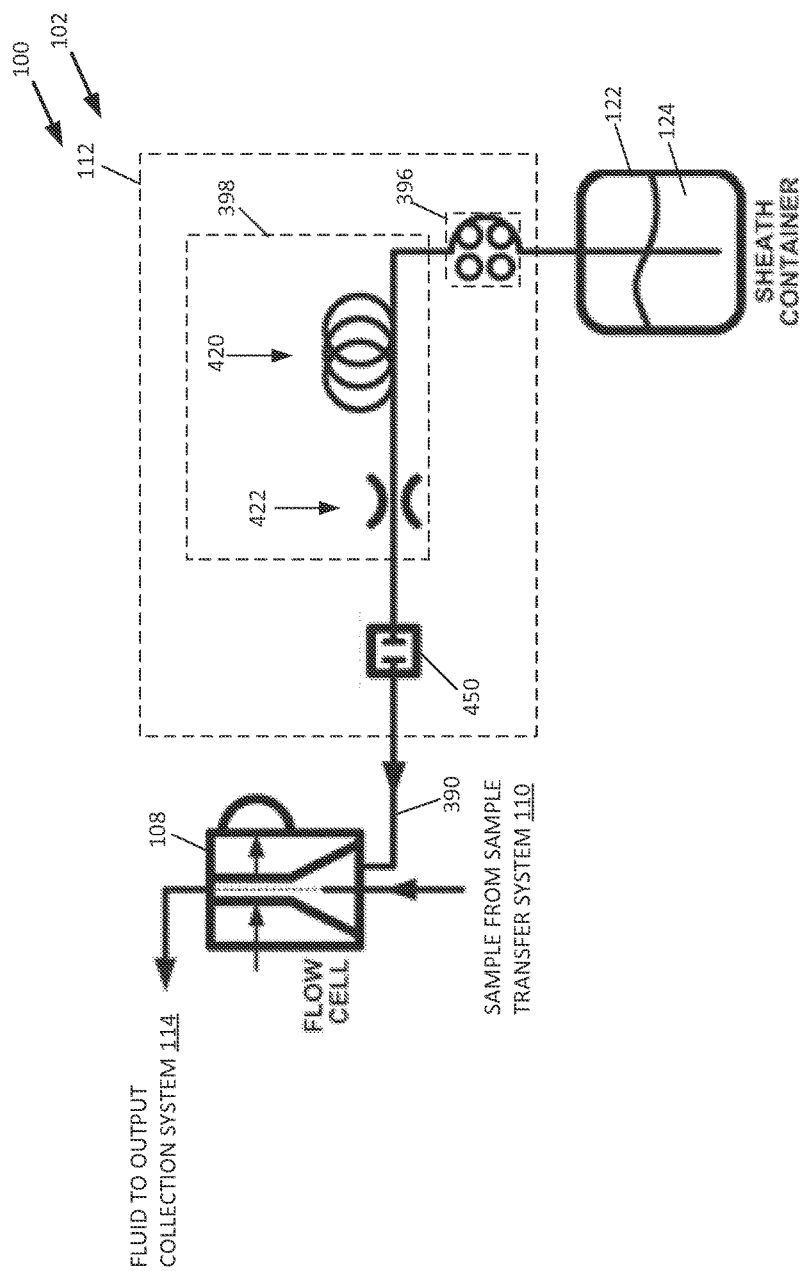
FIG. 27 is a schematic diagram of an embodiment of a sheath fluid transfer system, including a pulse attenuation system and a pressure retention valve, of the fluidics system of a flow cytometer.

FIG. 27 is a schematic diagram of an embodiment of a sheath fluid transfer system 112, including a pulse attenuation system 398 and a pressure retention valve 450, of the fluidics system 102 of a flow cytometer 100. In this embodiment, the sheath fluid transfer system 112 includes a sheath aspiration pump 396, a pulse attenuation system 398, and a pressure retention valve 450.

The pulse attenuation system 398 is a system configured to dampen or attenuate pulses created by the sheath aspiration pump 396. For example, in some embodiments, the sheath aspiration pump 396 is a peristaltic pump, the output of which is pulsatile. The pulse attenuation system 398 includes an elastic flow member 420 and a flow restriction member 422. The elastic flow member 420 and the flow restriction member 422 are described in greater detail with respect to FIG. 22.

The pressure retention valve 450 is a device that regulates the flow of sheath fluid 124 along the sheath fluid path 390. The pressure retention valve 450 may be actuated between an open position, which allows the sheath fluid 124 to flow through the sheath fluid path 390, and a closed position, which stops the flow of the sheath fluid 124 through the sheath fluid path 390. In some embodiments, the pressure retention valve 450 is controlled electronically.

In some embodiments, a delay is required to allow the flow rate of sheath fluid 124 through the pulse attenuation system 398 to stabilize after the sheath aspiration pump 396 is activated. The embodiment illustrated in FIG. 27 avoids or minimizes this delay in some circumstances as described below.

After the flow rate of sheath fluid 124 has stabilized after the sheath aspiration pump 396 is activated, the pressure retention valve 450 is closed and the sheath aspiration pump 396 is simultaneously stopped. The sheath fluid 124 trapped between the sheath aspiration pump 396, which is occlusive, and the pressure retention valve 450 retains substantially all of the stabilized sheath pressure.

During the subsequent aspiration of sheath fluid 124, the sheath aspiration pump 396 is started and the pressure retention valve 450 is opened simultaneously. Because the pulse attenuation system 398 has retained substantially all of the stabilized sheath pressure, the time required for the flow rate of sheath fluid 124 to stabilize is reduced.

Figure 28:
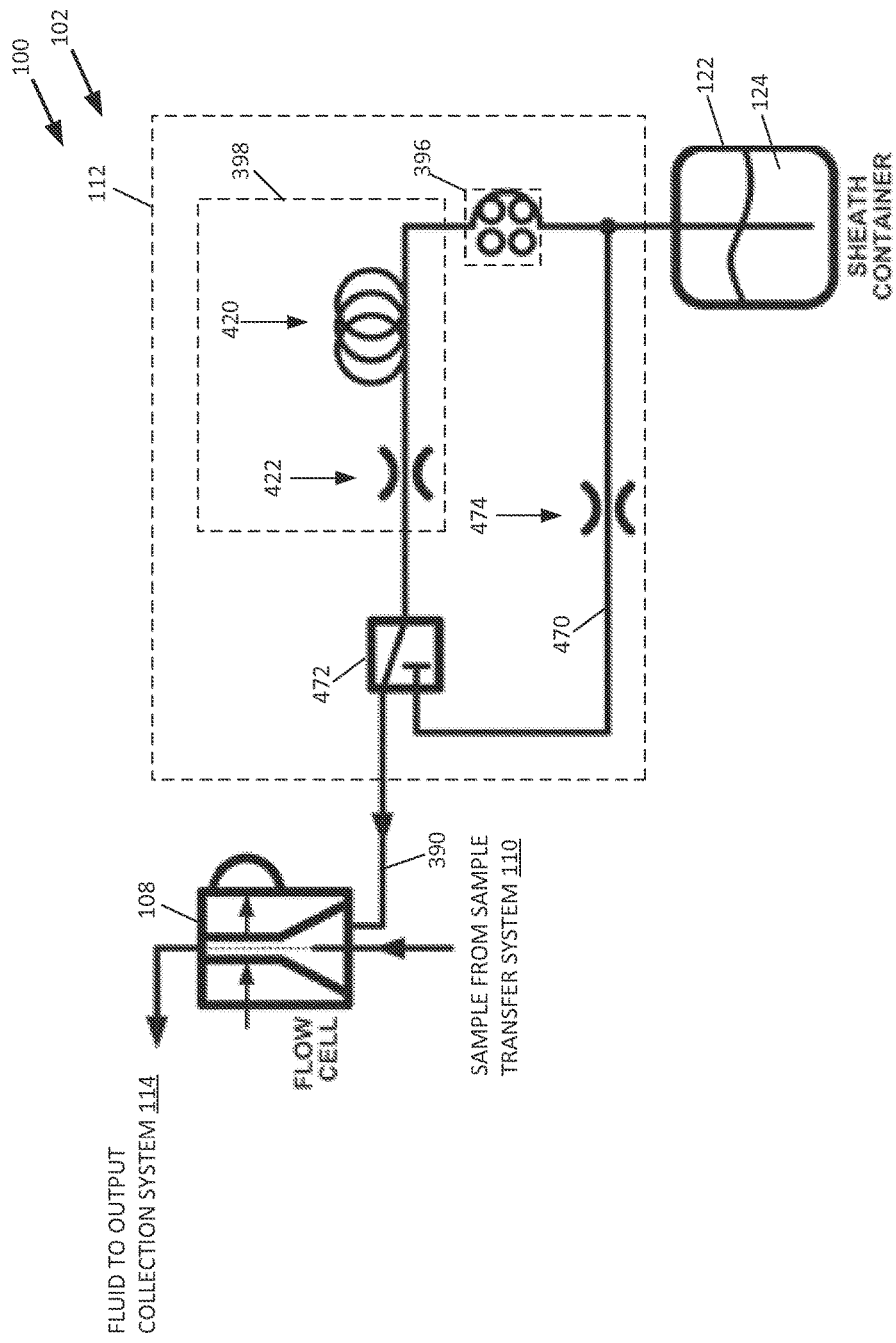
FIG. 28 is a schematic diagram of an embodiment of a sheath fluid transfer system, including a pulse attenuation system and a recirculation fluid path, of the fluidics system of a flow cytometer.

FIG. 28 is a schematic diagram of an embodiment of a sheath fluid transfer system 112, including a pulse attenuation system 398 and a recirculation fluid path 470, of the fluidics system 102 of a flow cytometer 100. In this embodiment, the sheath fluid transfer system 112 includes a sheath aspiration pump 396, a pulse attenuation system 398, a recirculation fluid path 470, a recirculation valve 472, and a recirculation flow restriction member 474.

The pulse attenuation system 398 is a system configured to dampen or attenuate pulses created by the sheath aspiration pump 396. For example, in some embodiments, the sheath aspiration pump 396 is a peristaltic pump, the output of which is pulsatile. The pulse attenuation system 398 includes an elastic flow member 420 and a flow restriction member 422. The elastic flow member 420 and the flow restriction member 422 are described in greater detail with respect to FIG. 22.

The recirculation fluid path 470 is a path for conveying the sheath fluid 124 from the sheath fluid path 390 downstream of the pulse attenuation system 398 to the sheath fluid path 390 upstream of the sheath aspiration pump 396. The recirculation fluid path 470 allows the sheath fluid 124 to recirculate through the sheath aspiration pump 396 and the pulse attenuation system 398. An example of the recirculation fluid path 470 is a silicone tube. Other embodiments of the recirculation fluid path 470 are possible as well.

The recirculation valve 472 is a device that regulates the flow of sheath fluid 124 along the sheath fluid path 390. The recirculation valve 472 may be actuated between a first position, which directs the sheath fluid 124 along the sheath fluid path 390 towards the flow cell 108, and a second position, which directs the sheath fluid 124 into the recirculation fluid path 470. In some embodiments, the recirculation valve 472 is controlled electronically.

The recirculation flow restriction member 474 is a member that is configured to provide flow resistance equal to that of the flow cell 108. In some embodiments, the recirculation flow restriction member 474 is an orifice. In other embodiments, the recirculation flow restriction member 474 is a length of tubing with an inner diameter that is smaller than that of the recirculation fluid path 470. Yet other embodiments of recirculation flow restriction member 474 are possible as well.

In some embodiments, a delay is required to allow the flow rate of sheath fluid 124 through the pulse attenuation system 398 to stabilize after the sheath aspiration pump 396 is activated. The embodiment illustrated in FIG. 28 avoids or minimizes this delay in some circumstances as described below.

With the recirculation valve 472 connecting the pulse attenuation system 398 to the recirculation fluid path 470, the sheath aspiration pump 396 is started. After a delay, a final stabilized pressure for the sheath fluid 124 is established in the pulse attenuation system 398 that is close to the final stabilized pressure for the sheath fluid 124 when the sheath fluid 124 is directed through the flow cell 108.

During subsequent aspiration of sheath fluid 124, the recirculation valve 472 is switched to connect the pulse attenuation system 398 to the flow cell 108. Because the pulse attenuation system 398 has retained substantially all of the stabilized sheath pressure, the time required for the flow rate of sheath fluid 124 to stabilize is reduced.

Figure 29:
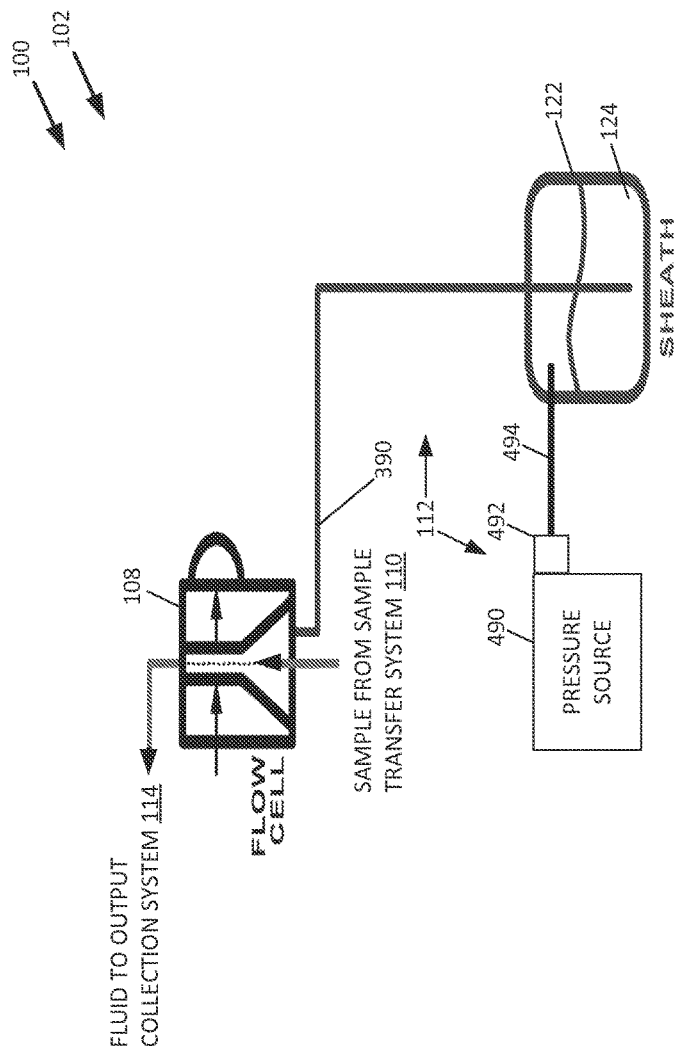
FIG. 29 is a schematic block diagram illustrating additional aspects of an exemplary fluidics system of the flow cytometer, including an example of the sheath fluid transfer system.

FIG. 29 is a schematic block diagram illustrating additional aspects of an exemplary fluidics system 102 of the flow cytometer 100, including an example of the sheath fluid transfer system 112. FIG. 29 illustrates the sheath fluid transfer system 112 configured to transfer the sheath fluid 124. Also shown is the sheath fluid source 122 including the sheath fluid 124.

As shown in FIG. 1, the example fluidics system 102 includes the flow cell 108, the sample transfer system 110, the sheath fluid transfer system 112, and the output collection system 114. In the example shown in FIG. 29, the sheath fluid transfer system 112 includes a sheath fluid path 390, a pressure source 490, a pressure regulator valve 492, and a pressure transfer member 494.

The sheath fluid path 390 is a path for conveying the sheath fluid 124 through the sheath fluid transfer system 112 to the flow cell 108. An example of the sheath fluid path 390 is a silicone tube. In some embodiments, the sheath fluid path 390 is formed from multiple silicone tubes. In addition, in some embodiments, the sheath fluid path 390 is formed from pressurized tubing (e.g., tubing pressurized to 4 psi). Other embodiments of the sheath fluid path 390 are possible as well. The sheath fluid path 390 is connected to the sheath fluid source 122 and the flow cell 108.

The pressure source 490 is a system configured to generate a substantially constant gas pressure. In some embodiments, the pressure source 490 is a pressurized vessel containing liquid carbon dioxide (CO2). Under sufficient pressure, CO2 will be in liquid at room temperature (e.g., approximately 70 degrees Fahrenheit). For example, CO2 will be in liquid and gas form at 70 degrees Fahrenheit at a pressure of approximately 835 psi. In normal operating conditions, the partial vapor pressure of CO2 remains constant at 835 psi. Accordingly, the vessel containing liquid CO2 will provide a source of constant pressure of 835 psi. Some of the benefits of using a vessel containing liquid CO2 as the pressure source 490 include that it is inexpensive, includes few mechanical parts, and the pressure is inherently constant, without the spikes or pulsations common in mechanical pressure/pumping devices. A vessel containing liquid CO2 is an example of a container of liquid CO2.

The pressure regulator valve 492 is a device that regulates the flow of pressure from the pressure source 490 to the pressure transfer member 494. In some embodiments, the pressure regulator valve 492 may be actuated between an open position, which allows pressure to enter the pressure transfer member 494, and a closed position, which prevents pressure from entering the pressure transfer member 494. In other embodiments, the pressure regulator valve 492 further increases or decreases the pressure before it allows the pressure to enter the pressure transfer member 494. In some embodiments, the pressure regulator valve 492 is not included.

The pressure transfer member 494 is a device for transferring pressure from the pressure source 490 to the sheath fluid source 122. An example of the pressure transfer member 494 is a tube. In some embodiments, the pressure transfer member 494 is a rigid tube. Other embodiments of the pressure transfer member 494 are possible as well. The pressure transfer member 494 is connected to the pressure regulator valve 492 or the pressure source 490 and the sheath fluid source 122. In some embodiments, the pressure is transferred through transferring CO2 vapor.

The CO2 vapor from the pressure source 490 exerts a pressure on the sheath fluid 124. In some embodiments, this pressure pushes the sheath fluid 124 into and through the sheath fluid path to the flow cell 108. In this manner, a constant flow of the sheath fluid 124 is delivered to the flow cell 108. Although the pressure source 490 has been described with respect to a vessel containing liquid CO2, other embodiments are possible in which other elements or chemical compounds are contained in a vessel such that the liquid phase of the compound is in equilibrium with the gas phase of the compound.

Figure 30:
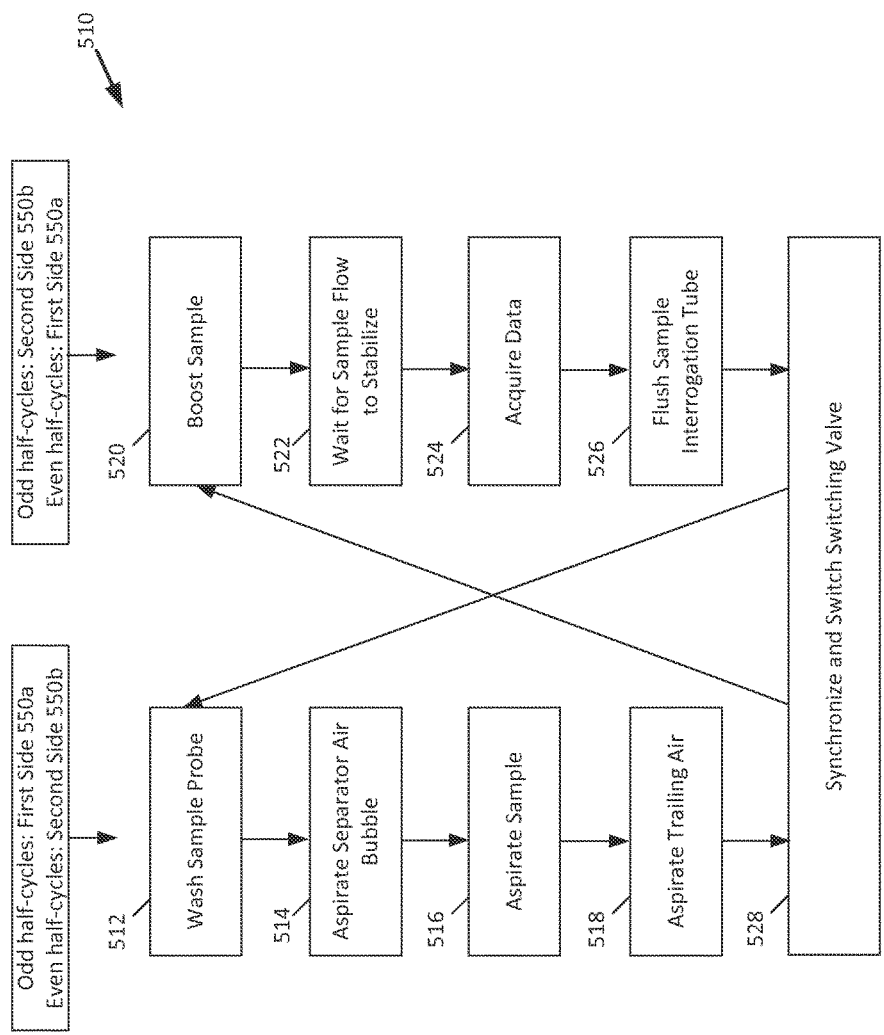
FIG. 30 is a flow chart of an example process for transferring a sample to the flow cell of flow cytometer using an embodiment of the fluidics system.

FIG. 30 is a flow chart of an example process 510 for transferring a sample 120 to the flow cell 108 of flow cytometer 100 using an embodiment of the fluidics system 102.

The process 510 allows two samples to be processed in parallel. The process 510 is described below with respect to a sample transfer system 110 that has a first side 550*a* and second side 550*b* to support parallel sample processing. Multiple samples are processed by repeating full cycles of operations by the sample transfer system 110. Each full cycle consists of a first half-cycle (comprising performing a first set of steps) followed by a second half-cycle (comprising performing a second set of steps). During the first half-cycle (and all odd-numbered half-cycles) the first side 550*a* performs the steps listed in the left column (steps 512-518) in series and the second side 550*b* performs the steps listed in the right column (steps 520-526) in series. During the second half-cycle (and all even-numbered half-cycles) the second side 550*b* performs the steps listed in the left column (steps 512-518) in series and the first side 550*a* performs the steps listed in the right column (steps 520-526) in series. The steps are described with reference to the parts of the first side 550*a*. The sample transfer system is illustrated and described in greater detail with respect to FIGS. 31-34.

Initially, step 512 is performed on the first side 550*a*. Step 512 is performed with the switching valve 552 in the first state 556. In the first state 556, switching valve 552 is configured to connect the first side 550*a* to the sample probe 150 via sample fluid path 152 and the second side 550*b* to the sample interrogation tube 554.

During step 512, the sample probe 150, the staging tube 562*a*, and the switching valve 552 are cleaned by performing a wash process. Step 520 (described below) is initiated on the second side 550*b* at the same time that step 512 is initiated on the first side 550*a*.

The exterior of the sample probe 150 is washed by opening the wash valve 160 and the vacuum valve 164. With the wash valve 160 open, a washing fluid (often sheath fluid) is able to flow through the wash fluid path 158 into the wash collar 156. The washing fluid contacts the exterior surface of the sample probe 150, washing particles of the sample 120 off of the sample probe 150. Similarly, with the vacuum valve 164 open, the external vacuum creates a vacuum force in the wash collar 156 through vacuum path 162. The washing fluid and any particles of sample 120 that were removed from the exterior of the sample probe 150 by the washing fluid are pulled out of the wash collar 156 along the vacuum path 162 by the vacuum.

Also during step 512, flush valve 566*a* is opened. This allows sheath fluid from the fluid-driving source 568*a* to flow through the staging tube 562*a*, the switching valve 552, the sample fluid path 152, and the sample probe 150. This sheath fluid exits the sample probe 150 in the wash collar 156 where it is pulled to waste through the vacuum path 162. This flow of sheath fluid washes the interior of each of the components it flows through. This wash process operates to minimize carryover between consecutive samples.

Next, step 514 is performed on the first side 550*a*. During step 514, a separator air bubble is aspirated into the sample probe 150 by creating a negative pressure by running the sample pump 560*a* while the tip of sample probe 150 is in the air. During aspiration of the separator air bubble, the sample probe 150 reciprocates down from the wash collar 156 until the tip of the sample probe 150 is immersed in sample 120. Aspiration of the separator air bubble is completed before the tip of the sample probe 150 becomes submerged in sample 120.

Next, step 516 is performed on the first side 550*a*. During step 516, the sample 120 is aspirated into the sample probe 150 by creating negative pressure by running the sample pump 560*a* while the tip of the sample probe 150 is submerged in the sample 120.

Next, step 518 is performed on the first side 550*a*. During step 518, the sample probe 150 reciprocates up until it reaches the wash collar 156. After a suitable delay to ensure that the tip of the sample probe 150 has moved above the surface of the sample 120 and is in air, trailing air is aspirated into the sample probe 150 by creating a negative pressure by running the sample pump 560*a*. The sample pump 560*a* stops aspirating trailing air once the aspirated bolus of sample 120 is positioned in the staging tube 562*a*.

Next, after waiting (if necessary) for step 526 to complete on the second side 550*b*, step 528 is performed. During step 528, switching valve 552 is switched to a second state 558. In the second state 558, switching valve 552 is configured to connect the first side 550*a* to the sample interrogation tube 554 and the second side 550*b* to the sample probe 150 via sample fluid path 152. After the switching valve 552 has completed switching from the first state 556 to the second state 558, the first or other odd numbered half-cycle is complete and the second or other even numbered half-cycle begins.

Next, step 520 is performed on the first side 550*a*. During step 520, the sample 120 resident in the staging tube 562*a* is boosted by running the sample pump 560*a* in reverse at a higher speed. This pushes the sample 120 away from the sample pump 560*a*, out of the staging tube 562*a*, through the switching valve 552, and into the sample interrogation tube 554. The sample pump 560*a* continues to boost the sample 120 until the sample 120 reaches the flow cell 108. Step 512 (described above) is initiated on the second side 550*b* at the same time that step 520 is initiated on the first side 550*a*.

Next, step 522 is performed on the first side 550*a*. During step 522, the sample pump 560*a* is run in reverse at a flow rate suitable for interrogation of the sample 120. Step 522 continues until the flow rate of the sample 120 has stabilized after the boosting operation of step 520.

Next, step 524 is performed on the first side 550*a*. During step 524, the sample 120 is interrogated by the sample interrogation and detection system 104. While the sample 120 is being interrogated, the sample pump 560a continues to run in reverse at a flow rate suitable for interrogation of the sample 120.

Next, step 526 is performed on the first side 550a. During step 526, the staging tube 562a, the switching valve 552, and the sample interrogation tube 554 are flushed. The sample pump 560a is run in reverse at a higher speed such that sheath fluid flows through the staging tube 562a, the switching valve 552, and sample interrogation tube 554 and into the flow cell 108. Additionally, in some embodiments, the sample pump 560a is stopped after all sample 120 has been dispensed from the sample pump 560a and the flush valve 566a is opened to allow sheath fluid to flow through the staging tube 562a, the switching valve 552, and sample interrogation tube 554 and into the flow cell 108. This can further reduce carryover of particles between samples. This step 526 flushes any remaining particles of sample 120 out of the staging tube 562a, the switching valve 552, the sample interrogation tube 554, and the flow cell 108 in preparation for the interrogation of a subsequent sample.

Next, after waiting (if necessary) for step 518 to complete on the second side 550b, step 528 is performed again. During step 528, switching valve 552 is switched back to the first state 556. After the switching valve 552 has completed switching from the second state 558 to first state 556, the second or other even numbered half-cycle is complete and the full cycle is also complete. The sample transfer system 110 is ready to begin a new full cycle.

Figure 31:
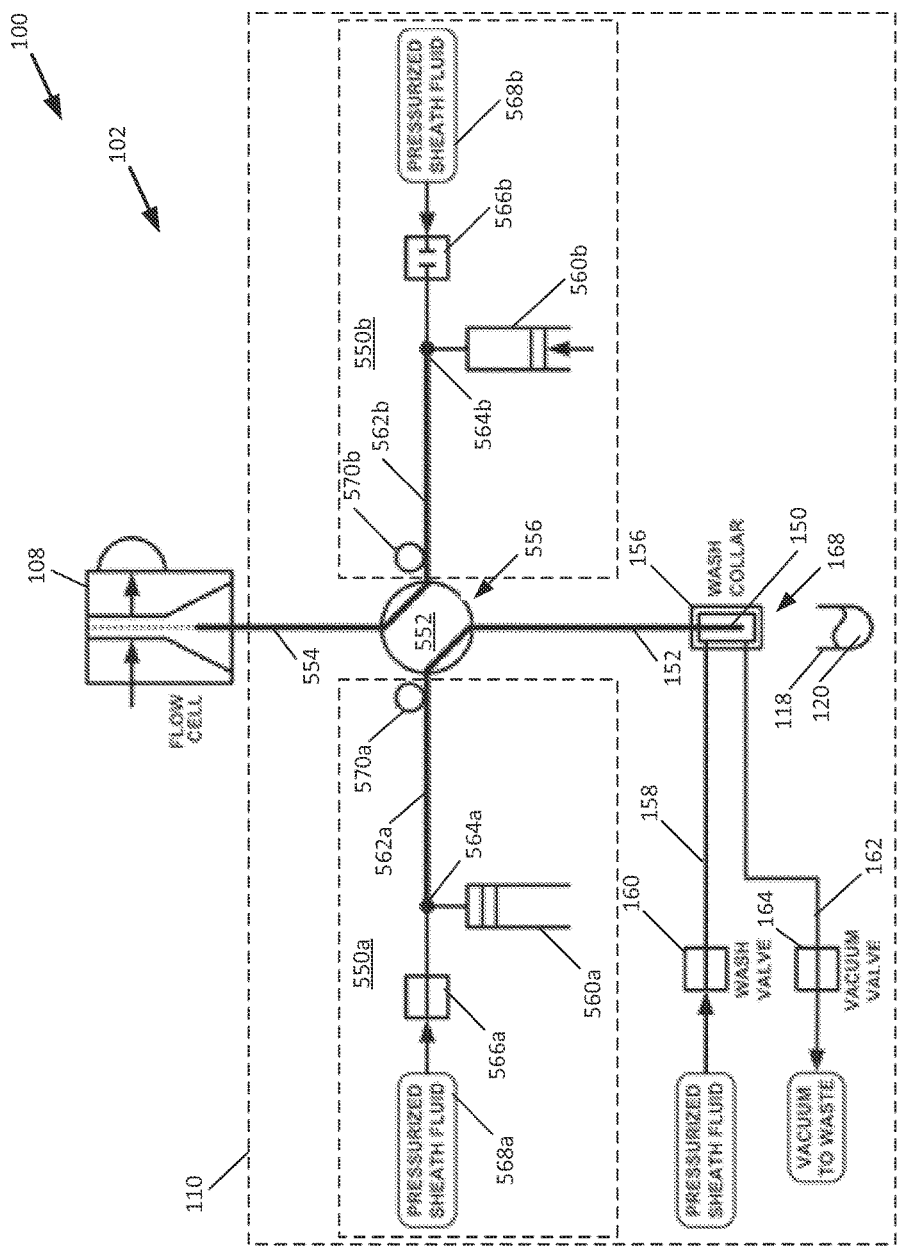
FIG. 31 is a schematic block diagram illustrating additional aspects of an exemplary fluidics system of the flow cytometer, including an example of the sample transfer system.

FIG. 31 is a schematic block diagram illustrating additional aspects of an exemplary fluidics system 102 of the flow cytometer 100, including an example of the sample transfer system 110. FIG. 31 illustrates the sample transfer system 110 in a configuration to wash the sample probe 150, while the sample 120 is being boosted on the second side 550b.

As shown in FIG. 1, the example fluidics system 102 includes the flow cell 108, the sample transfer system 110, the sheath fluid transfer system 112, and the output collection system 114. In the example shown in FIG. 31, the sample transfer system 110 includes a sample probe 150, a sample fluid path 152, a first side 550a, a second side 550b, a switching valve 552, and a sample interrogation tube 554. The sample transfer system 110 also includes a wash collar 156, a wash fluid path 158, a wash valve 160, a vacuum path 162, and a vacuum valve 164 (which are described in detail with respect to FIG. 3).

The sample probe 150 is provided in some embodiments to extend into the sample source 118 to receive the sample 120 from the sample source 118. An example of the sample probe 150 is an aspiration needle. The sample probe 150 includes one or more apertures therein through which the sample 120 can be received from the sample source 118.

Figure 32:
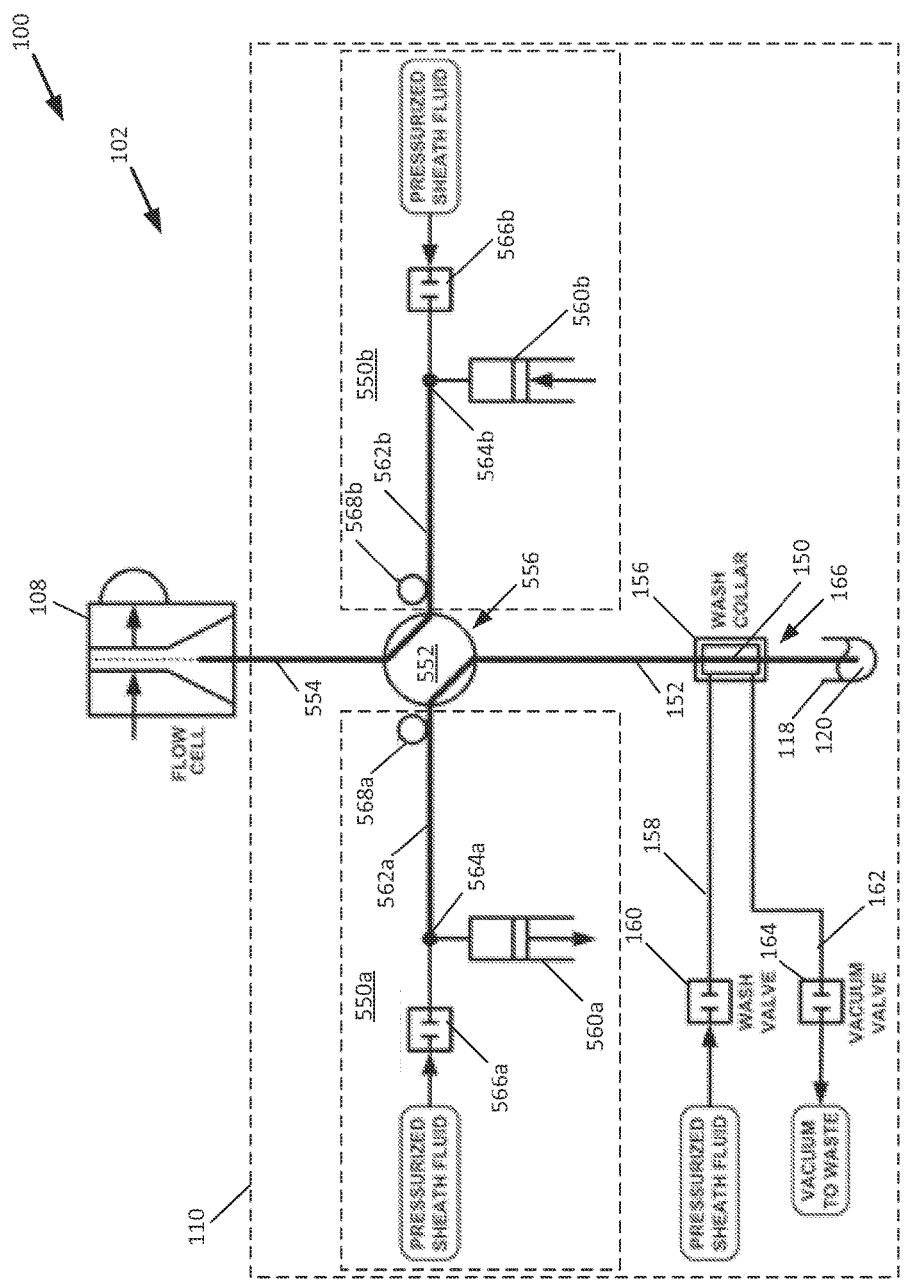
FIG. 32 is another schematic block diagram illustrating the example sample transfer system of FIG. 31.
Figure 33:
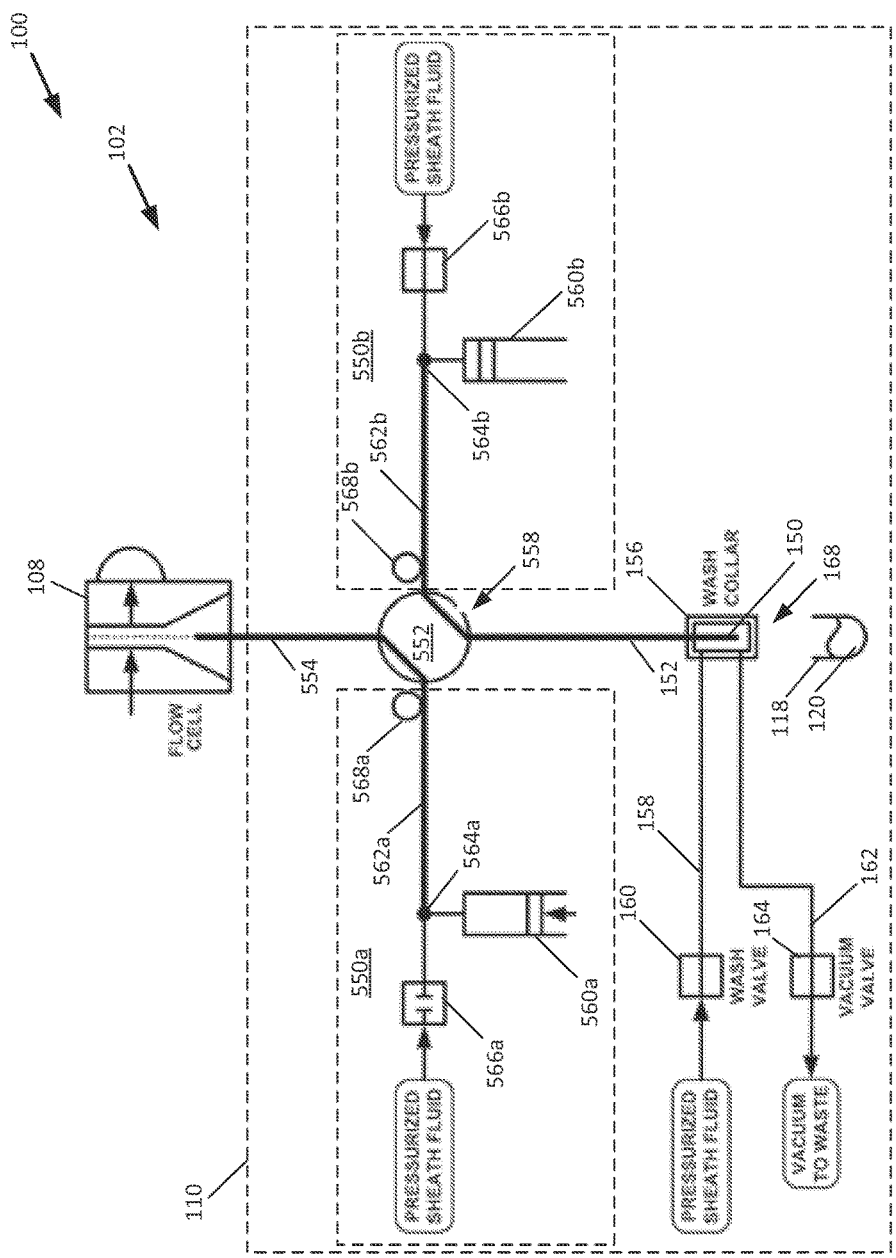
FIG. 33 is another schematic block diagram illustrating the example sample transfer system of FIG. 31.

In some embodiments, the sample probe 150 reciprocates between a lowered position 166 (shown in FIGS. 32 and 34) and a raised position 168 (shown in FIGS. 31 and 33). In the lowered position 166, the tip of the sample probe 150 is submerged in the sample 120. In the raised position 168, the sample probe 150 is retracted into the wash collar 156, where it can be cleaned during step 512. In some embodiments, the instrument electronics 106 control the selective reciprocation of the sample probe 150 between the lowered position 166 and the raised position 168.

The sample fluid path 152 is a path for conveying the sample 120 through the sample transfer system. An example of the sample fluid path 152 is a silicone tube. In some embodiments, the sample fluid path 152 is formed from multiple silicone tubes. In addition, in some embodiments, the sample fluid path 152 is formed from pressurized tubing (e.g., tubing pressurized to 4 psi). Other embodiments of the sample fluid path 152 are possible as well. The sample fluid path 152 is connected to the sample probe 150 and the switching valve 552.

The first side 550a and the second side 550b are fluidic systems and are configured to alternate between aspirating a sample 120 from the sample source 118 and conveying the sample 120 to the flow cell 108. The first side 550a includes a sample pump 560a, a staging tube 562a, a tee fitting 564a, a flush valve 566a, a fluid-driving source 568a, and a bubble detector 570a. The second side 550b is identical to the first side 550a, and, accordingly, includes a sample pump 560b, a staging tube 562b, a tee fitting 564b, a flush valve 566b, a fluid-driving source 568b, and a bubble detector 570b.

The sample pumps 560a-b are devices and are configured to move fluid through the sample transfer system 110. In some embodiments, the sample pumps 560a-b are configured to create a vacuum to aspirate the sample 120 from the sample source 118. The sample pumps 560a-b are also configured to operate in reverse to create a positive pressure that pushes the sample 120 into the flow cell 108. An example of the sample pumps 560a-b is a syringe pump. There are many other embodiments of sample pumps 560a-b as well. Another non-limiting example of the sample pumps 560a-b is a peristaltic pump.

In some embodiments, a syringe pump consists of a barrel in which a piston reciprocates. The piston seals to the barrel, and only one open port is provided above the piston. When the piston is withdrawn relative to the open port, the resulting suction draws fluid into the syringe pump through the open port. This is referred to as aspiration. Conversely, when the piston is driven toward the open port, the resulting positive pressure displaces fluid out of the syringe pump through the port. This is referred to as dispensing. When used in conjunction with an incompressible fluid, the fluid volume aspirated or dispensed is proportional to the piston displacement.

The staging tubes 562a-b are paths for conveying fluid through the sample transfer system 110. An example of the staging tubes 562a-b is a silicone tube. In some embodiments, the staging tubes 562a-b are formed from multiple silicone tubes. In addition, in some embodiments, the staging tubes 562a-b are formed from pressurized tubing (e.g., tubing pressurized to 4 psi). Other embodiments of the staging tubes 562a-b are possible as well. The staging tubes 562a-b are connected to switching valve 552 and the tee fittings 564a-b.

The tee fittings 564a-b are three-way connectors and connect the sample pumps 560a-b, the staging tubes 562a-b, and the flush valves 566a-b. In some embodiments, the tee fittings 564a-b are formed from silicone. Other embodiments of the tee fittings 564a-b are possible as well.

The flush valves 566a-b are devices that regulate the flow of sheath fluid into the tee fittings 564a-b. One side of the flush valves 566a-b is connected to the fluid-driving sources 568a-b, which contain sheath fluid. The other side is connected to the tee fittings 564a-b. The flush valves 566a-b may be actuated between an open position, which allows sheath fluid into the tee fittings 564a-b, and a closed position, which stops sheath fluid from flowing into the tee fittings 564a-b. In some embodiments, the flush valves 566a-b are controlled by the instrument electronics 106.

The fluid-driving sources 568a-b are devices that contain sheath fluid and push the sheath fluid towards the flush valves 566a-b, such that when the flush valves 566a-b are in an open position the sheath fluid flows into the staging tubes 562a-b. Some non-limiting examples of the fluid-driving sources 568a-b include pressurized tanks, gravity-fed tanks, and various pumps attached to a reservoir.

The bubble detectors 570a-b are devices that are configured to detect whether the staging tubes 562a-b contain air or fluid. In some embodiments, the bubble detectors 570a-b include a light beam emitter and a light beam detector that are configured to interrogate the interiors of the staging tubes 562a-b. In other embodiments, the bubble detectors 570a-b include an ultrasonic emitter and an ultrasonic detector that are configured to interrogate the interiors of the staging tubes 562a-b. Other embodiments of bubble detectors 570a-b are possible as well. The bubble detectors 570a-b are disposed along the staging tubes 562a-b near the switching valve 552.

In some embodiments, the bubble detectors 570a-b are configured to detect the presence or absence of expected air bubbles in the staging tubes 562a-b. In other embodiments, the bubble detectors 570a-b are configured to detect the presence of unexpected air bubbles in the staging tubes 562a-b. In some embodiments, when an unexpected air bubble is detected, the bubble detectors 570a-b determine that the present sample is an error. In some embodiments, the bubble detectors 570a-b convey this information to the instrument electronics 106. Some embodiments do not include the bubble detectors 570a-b.

The switching valve 552 is a device with four fluid ports and two internal flow paths and is configured to switch between a first state 556 and a second state 558. The switching valve 552 is connected to the sample fluid path 152, the sample interrogation tube 554, and the staging tubes 562a-b. In the first state 556, the switching valve 552 is configured to connect the first side 550a to the sample probe 150 via sample fluid path 152 and the second side 550b to the sample interrogation tube 554. In the second state 558, the switching valve 552 is configured to connect the first side 550a to the sample interrogation tube 554 and the second side 550b to the sample probe 150 via sample fluid path 152. In some embodiments, the switching valve 552 is a rotary valve in which the four ports are located on the perimeter of the switching valve 552 at ninety degree intervals and the two internal flow paths are configured to connect adjacent pairs of ports. This rotary valve switches states through the rotation by ninety degrees of an internal component containing the two internal flow paths. This changes which pairs of ports are connected by the internal flow paths. Other embodiments of switching valve 552 are possible as well.

The sample interrogation tube 554 is a path for transferring the sample 120 from the switching valve 552 to the flow cell 108. An example of the sample interrogation tube 554 is a silicone tube. In some embodiments, the sample interrogation tube 554 is formed from multiple silicone tubes. In addition, in some embodiments, the sample interrogation tube 554 is formed from pressurized tubing (e.g., tubing pressurized to 4 psi). Other embodiments of the sample interrogation tube 554 are possible as well. The sample interrogation tube 554 is connected to the flow cell 108 and the switching valve 552.

In the embodiment shown in FIG. 31, the sample transfer system 110 is configured to perform step 512 on the first side 550a and step 520 on the second side 550b. The sample probe 150 is in the raised position 168. The switching valve 552 is in the first state 556.

FIG. 32 is another schematic block diagram illustrating the example sample transfer system 110 of FIG. 31. In the embodiment shown in FIG. 32, the sample transfer system 110 is configured to perform step 516 on the first side 550a and step 524 on the second side 550b. The sample probe 150 is in the lowered position 166. The switching valve 552 is in the first state 556.

FIG. 33 is another schematic block diagram illustrating the example sample transfer system 110 of FIG. 31. In the embodiment shown in FIG. 33, the sample transfer system 110 is configured to perform step 520 on the first side 550a and step 512 on the second side 550b. The sample probe 150 is in the raised position 168. The switching valve 552 is in the second state 558.

Figure 34:
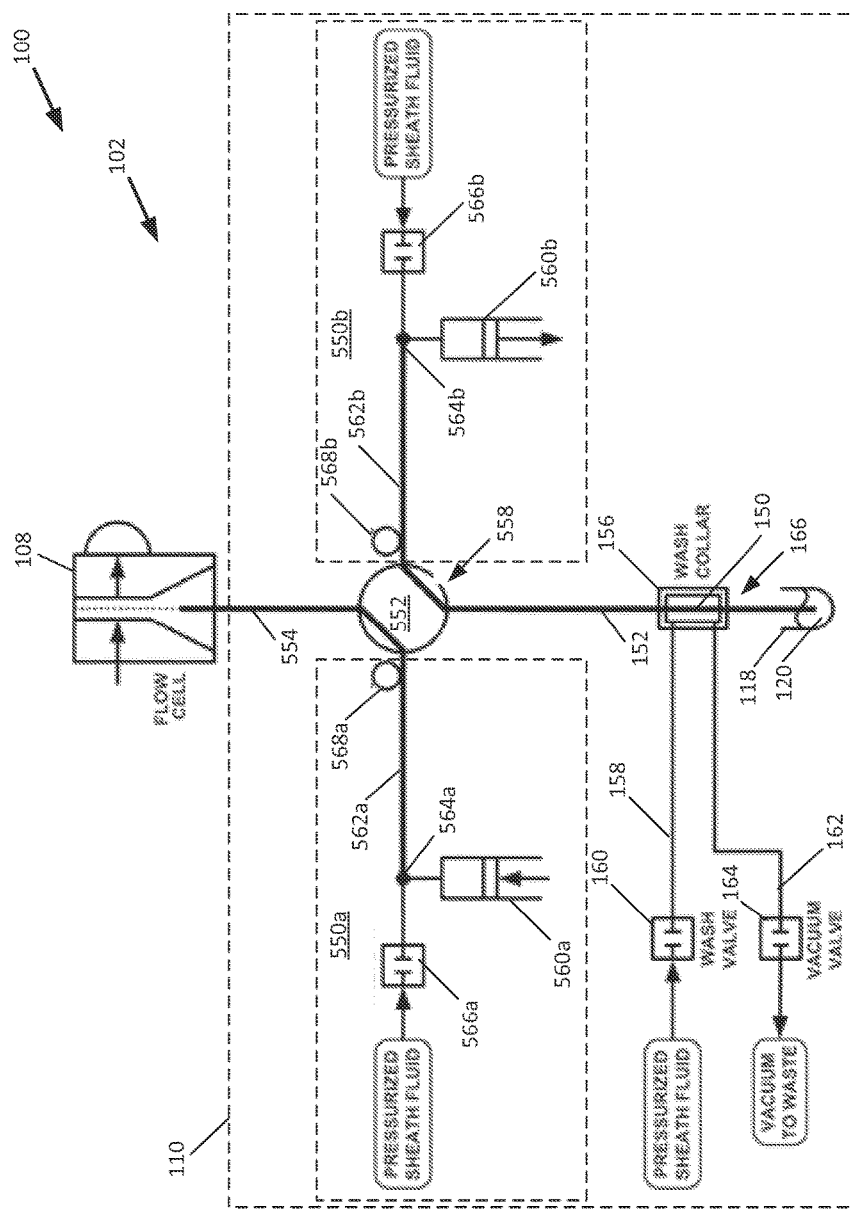
FIG. 34 is another schematic block diagram illustrating the example sample transfer system of FIG. 31.

FIG. 34 is another schematic block diagram illustrating the example sample transfer system 110 of FIG. 31. In the embodiment shown in FIG. 34, the sample transfer system 110 is configured to perform step 524 on the first side 550a and step 516 on the second side 550b. The sample probe 150 is in the lowered position 166. The switching valve 552 is in the second state 558.

Figure 35:
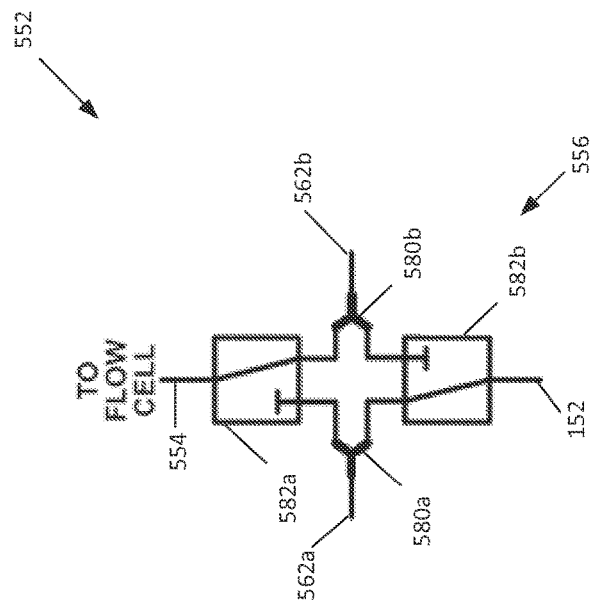
FIG. 35 is schematic block diagram illustrating an alternate embodiment of a switching valve of the sample transfer system of FIG. 31.

FIG. 35 is schematic block diagram illustrating an alternate embodiment of the switching valve 552 of the sample transfer system 110 of FIG. 31. In FIG. 35, the switching valve 552 is shown in the first state 556.

The switching valve 552 includes a first fitting 580a, a second fitting 580b, a first three-way valve 582a, and a second three-way valve 582b. The first fitting 580a and a second fitting 580b are connectors that are configured to connect three fluid paths. In some embodiments, the first fitting 580a and the second fitting 580b are wye fittings. In other embodiments, the first fitting 580a and the second fitting 580b are tee fittings. Yet other embodiments of the first fitting 580a and the second fitting 580b are possible as well. The three-way valves 582a-b are fluid valves and each have a single common port and two selectable ports. The three-way valves 582a-b are configured to connect the common port to one or the other of the selectable ports. Flow is permitted between the common port and the selected port, and flow is occluded for the non-selected port.

The first fitting 580a is connected to the staging tube 562a of the first side 550a, a selectable port of the first three-way valve 582a, and a selectable port of the second three-way valve 582b. The second fitting 580b is connected to the staging tube 562b of the second side 550b, a selectable port of the first three-way valve 582a, and a selectable port of the second three-way valve 582b.

The common port of the first three-way valve 582a is connected to the sample interrogation tube 554. The selectable ports of the first three-way valve 582a are connected to the first fitting 580a and the second fitting 580b.

The common port of the second three-way valve 582b is connected to the sample fluid path 152. The selectable ports of the second three-way valve 582b are connected to the first fitting 580a and the second fitting 580b.

In the first state 556, the first three-way valve 582a connects the staging tube 562b to the sample interrogation tube 554 and the second three-way valve 582b connects the staging tube 562a to the sample fluid path 152.

Figure 36:
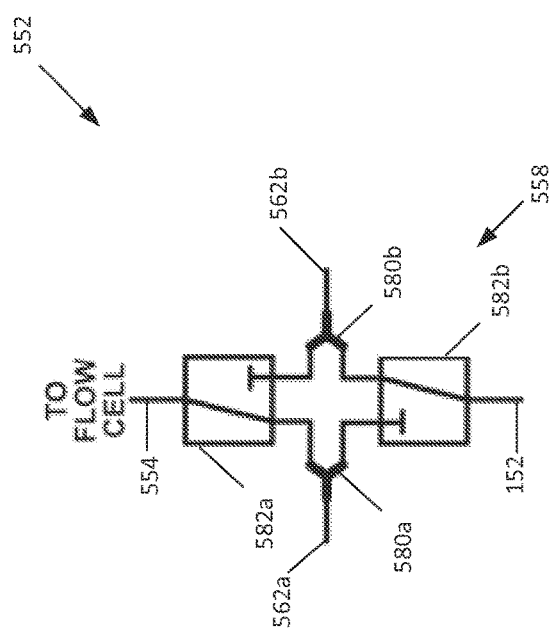
FIG. 36 is another schematic block diagram illustrating the switching valve shown in FIG. 35.

FIG. 36 is another schematic block diagram illustrating the switching valve 552 shown in FIG. 35. In FIG. 36, the switching valve 552 is shown in the second state 558.

In the second state 558, the first three-way valve 582a connects the staging tube 562a to the sample interrogation tube 554 and the second three-way valve 582b connects the staging tube 562b to the sample fluid path 152.

Figure 37:
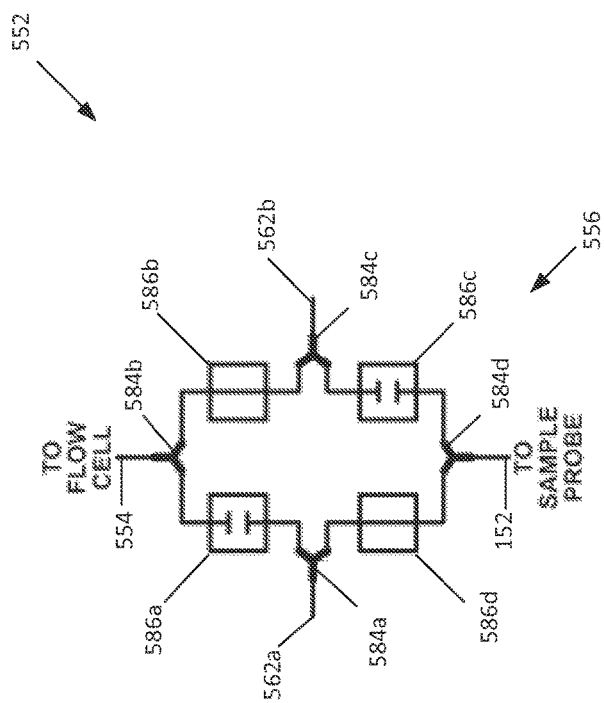
FIG. 37 is schematic block diagram illustrating an alternate embodiment of the switching valve of the sample transfer system of FIG. 31.

FIG. 37 is schematic block diagram illustrating an alternate embodiment of the switching valve 552 of the sample transfer system 110 of FIG. 31. In FIG. 37, the switching valve 552 is shown in the first state 556.

The switching valve 552 includes fittings 584a-d and valves 586a-d. The fittings 584a-d are connectors that are configured to connect three fluid paths. In some embodiments, the fittings 584a-d are wye fittings. In other embodiments, the fittings 584a-d are tee fittings. Yet other embodiments of the fittings 584a-d are possible as well. The valves 586a-d are two-way valves that can be actuated between an open state in which fluid path is open and a second state in which the fluid path is occluded. In some embodiments, the valves 586a-d are pinch valves. Other embodiments of the valves 586a-d are possible as well.

The fitting 584a connects to staging tube 562a on the first side 550a, valve 586a, and valve 586d. The fitting 584b connects to the sample interrogation tube 554, valve 586a, and valve 586b. The fitting 584c connects to staging tube 562b on the second side 550b, valve 586b, and valve 586c. The fitting 584d connects to sample fluid path 152, valve 586c, and valve 586d.

In the first state 556, the valve 586a is closed, occluding the fluid path between the staging tube 562a and the sample interrogation tube 554; the valve 586b is open, opening the fluid path between the staging tube 562b and the sample interrogation tube 554; the valve 586c is closed, occluding the fluid path between the sample fluid path 152 and the staging tube 562b; and the valve 586d is open, opening the fluid path between the sample fluid path 152 and the staging tube 562a.

Figure 38:
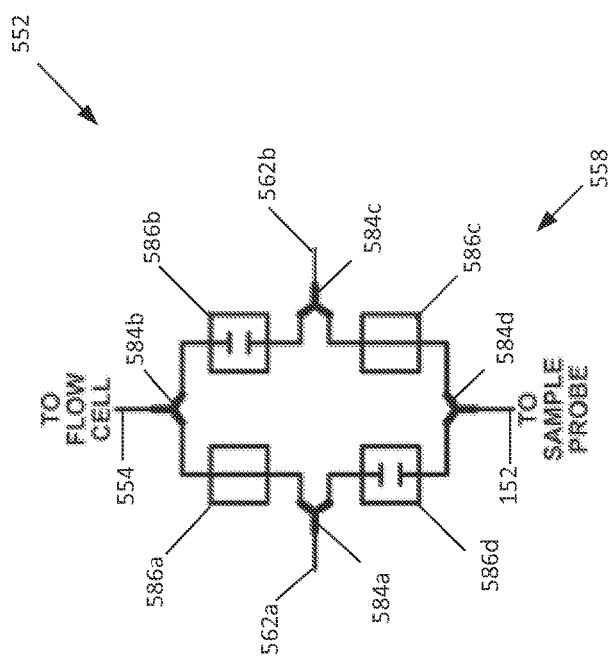
FIG. 38 is another schematic block diagram illustrating the switching valve shown in FIG. 37.

FIG. 38 is another schematic block diagram illustrating the switching valve 552 shown in FIG. 37. In FIG. 38, the switching valve 552 is shown in the second state 558.

In the second state 558, valve 586a is open, opening the fluid path between staging tube 562a and sample interrogation tube 554; valve 586b is closed, occluding the fluid path between staging tube 562b and sample interrogation tube 554; valve 586c is open, opening the fluid path between sample fluid path 152 and staging tube 562b; and valve 586d is closed, occluding the fluid path between sample fluid path 152 and staging tube 562a.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A flow cytometer comprising:
a flow cell for passing particles in a sample;
a sample probe to aspirate the sample;
a switching valve connected to the flow cell, the sample probe, a first tube section, and a second tube section, the switching valve having a first and a second selectable position, wherein the switching valve forms a fluid connection between the sample probe and the first tube section and between the flow cell and the second tube section when the switching valve is in the first position, and wherein the switching valve forms a fluid connection between the sample probe and the second tube section and between the flow cell and the first tube section when the switching valve is in the second position; and
a first pressure source connected to the first tube section, a second pressure source connected to the second tube section, and a third pressure source in fluid communication with a system fluid source, the system fluid source configured to provide system fluid,
wherein the first pressure source is configured to cause a first sample to flow from the sample probe to the first tube section, the second pressure source is configured to cause a second sample to flow from the second tube section to the flow cell when the switching valve is in the first position, and the third pressure source is configured to cause the system fluid to flow from the system fluid source, through the first tube section, and to the sample probe when the switching valve is in the first position.

2. The flow cytometer of claim 1, wherein the switching valve comprises a rotary valve.

3. The flow cytometer of claim 1, wherein the first pressure source is further configured to cause the first sample to flow from the first tube section to the flow cell when the switching valve is in the second position.

4. The flow cytometer of claim 3, wherein the second pressure source is further configured to cause a third sample to flow from the sample probe to the second tube section when the switching valve is in the second position.

5. The flow cytometer of claim 1, further comprising a flush valve disposed between the system fluid source and the first tube section to control the flow of system fluid from the first tube section to the sample probe.

6. The flow cytometer of claim 5, wherein the flush valve is configured to prevent the flow of system fluid from the first tube section to the sample probe when the first pressure source causes sample to flow from the sample probe to the first tube section.

7. The flow cytometer of claim 1, wherein the third pressure source is further configured to cause the system fluid to flow from the system fluid source, through the second tube section, and to the sample probe when the switching valve is in the second position.

8. The flow cytometer of claim 7, further comprising a flush valve disposed between the system fluid source and the second tube section to control the flow of system fluid from the second tube section to the sample probe.

9. The flow cytometer of claim 8, wherein the flush valve is configured to prevent the flow of system fluid from the second tube section to the sample probe when the second pressure source causes the sample to flow from the sample probe to the second tube section.

10. The flow cytometer of claim 8, further comprising a flush valve disposed between the system fluid source and the first tube section to control the flow of system fluid from the first tube section to the sample probe.

11. The flow cytometer of claim 1, further comprising a washing member in fluid communication with the system fluid source, the washing member being configured to wash an exterior surface of the sample probe.

12. The flow cytometer of claim 11, wherein the washing member is a wash collar.

13. The flow cytometer of claim 11, wherein the third pressure source is further configured to cause the system fluid to wash the exterior surface of the sample probe while the system fluid flows from the first tube section to the sample probe.

14. The flow cytometer of claim 1, wherein the first pressure source is a syringe.

15. The flow cytometer of claim 1, wherein the second pressure source is a syringe.

16. The flow cytometer of claim 1, wherein the switching valve is a single valve having four ports.

17. A flow cytometer comprising:
a flow cell for passing particles in a sample;
a sample probe to aspirate the sample;

a switching valve connected to the flow cell, the sample probe, a first tube section, and a second tube section, the switching valve having a first and a second selectable position, wherein the switching valve comprises a pair of three-way valves and forms a fluid connection between the sample probe and the first tube section and between the flow cell and the second tube section when the switching valve is in the first position, and wherein the switching valve forms a fluid connection between the sample probe and the second tube section and between the flow cell and the first tube section when the switching valve is in the second position; and a first pressure source connected to the first tube section, and a second pressure source connected to the second tube section, wherein the first pressure source is configured to cause a first sample to flow from the sample probe to the first tube section and the second pressure source is configured to cause a second sample to flow from the second tube section to the flow cell when the switching valve is in the first position.

18. The flow cytometer of claim 17, wherein each of the pair of three-way valves has three ports.

19. A flow cytometer comprising:

a flow cell for passing particles in a sample;

a sample probe to aspirate the sample;

a switching valve connected to the flow cell, the sample probe, a first tube section, and a second tube section, the switching valve having a first and a second selectable position, wherein the switching valve forms a fluid connection between the sample probe and the first tube section and between the flow cell and the second tube section when the switching valve is in the first position, and wherein the switching valve comprises four two-way valves, each two-way valve having two ports, and forms a fluid connection between the sample probe and the second tube section and between the flow cell and the first tube section when the switching valve is in the second position; and a first pressure source connected to the first tube section, and a second pressure source connected to the second tube section, wherein the first pressure source is configured to cause a first sample to flow from the sample probe to the first tube section and the second pressure source is configured to cause a second sample to flow from the second tube section to the flow cell when the switching valve is in the first position.

* * * * *